US007569345B2

(12) United States Patent
Cobleigh et al.

(10) Patent No.: US 7,569,345 B2
(45) Date of Patent: Aug. 4, 2009

(54) GENE EXPRESSION MARKERS FOR BREAST CANCER PROGNOSIS

(75) Inventors: Melody A. Cobleigh, Riverside, IL (US); Steve Shak, Hillsborough, CA (US); Joffre B. Baker, Montara, CA (US); Maureen T. Cronin, Los Altos, CA (US)

(73) Assignees: Genomic Health, Inc., Redwood City, CA (US); Rush-Presbyterian-St. Lukes Medical Center, Chicago, IL (US)

( * ) Notice: Subject to any disclaimer, the term of this patent is extended or adjusted under 35 U.S.C. 154(b) by 463 days.

(21) Appl. No.: 10/758,307

(22) Filed: Jan. 14, 2004

(65) Prior Publication Data

US 2004/0209290 A1 Oct. 21, 2004

Related U.S. Application Data

(60) Provisional application No. 60/440,861, filed on Jan. 15, 2003.

(51) Int. Cl.
*C12Q 1/68* (2006.01)
(52) U.S. Cl. ........................................................ 435/6
(58) Field of Classification Search .................. None
See application file for complete search history.

(56) References Cited

U.S. PATENT DOCUMENTS

| | | | | |
|---|---|---|---|---|
| 4,699,877 A | 10/1987 | Cline et al. | ................ | 435/6 |
| 4,968,603 A | 11/1990 | Slamon et al. | .............. | 435/6 |
| 5,015,568 A | 5/1991 | Tsujimoto et al. | ............. | 435/5 |
| 5,202,429 A | 4/1993 | Tsujimoto et al. | .......... | 536/23.5 |
| 5,459,251 A | 10/1995 | Tsujimoto et al. | .......... | 536/23.5 |
| RE35,491 E | 4/1997 | Cline et al. | ................ | 435/6 |
| 5,670,325 A | 9/1997 | Lapidus et al. | .............. | 435/6 |
| 5,741,650 A | 4/1998 | Lapidus et al. | .............. | 435/6 |
| 5,830,665 A | 11/1998 | Shuber et al. | ............... | 435/6 |
| 5,830,753 A | 11/1998 | Coulie et al. | ............... | 435/325 |
| 5,858,678 A | 1/1999 | Chinnadurai | ................ | 435/7.1 |
| 5,861,278 A | 1/1999 | Wong et al. | ................ | 435/69.1 |
| 5,928,870 A | 7/1999 | Lapidus et al. | .............. | 435/6 |
| 5,952,178 A | 9/1999 | Lapidus et al. | .............. | 435/6 |
| 5,952,179 A | 9/1999 | Chinnadurai | ................ | 435/6 |
| 5,962,312 A | 10/1999 | Plowman et al. | .......... | 435/320.1 |
| 5,985,553 A | 11/1999 | King et al. | ................ | 435/6 |
| 6,001,583 A | 12/1999 | Margolis | ................ | 435/7.23 |
| 6,020,137 A | 2/2000 | Lapidus et al. | .............. | 435/6 |
| 6,100,029 A | 8/2000 | Lapidus et al. | .............. | 435/6 |
| 6,143,529 A | 11/2000 | Lapidus et al. | .............. | 435/91.2 |
| 6,146,828 A | 11/2000 | Lapidus et al. | .............. | 435/6 |
| 6,171,798 B1 | 1/2001 | Levine et al. | ................ | 435/6 |
| 6,203,993 B1 | 3/2001 | Shuber et al. | ............... | 435/6 |
| 6,207,401 B1 | 3/2001 | Plowman et al. | ............ | 435/15 |
| 6,207,452 B1 | 3/2001 | Govindaswamy | .......... | 435/330 |
| 6,214,558 B1 | 4/2001 | Shuber et al. | ............... | 435/6 |
| 6,245,523 B1 | 6/2001 | Altieri | ................ | 435/69.1 |
| 6,248,535 B1 | 6/2001 | Danenberg et al. | .......... | 435/6 |
| 6,271,002 B1 | 8/2001 | Linsley et al. | ............. | 435/91.1 |
| 6,322,986 B1 | 11/2001 | Ross | ................ | 435/6 |
| 6,414,134 B1 | 7/2002 | Reed | ................ | 536/24.5 |
| 6,582,919 B2 | 6/2003 | Danenberg | ................ | 435/6 |
| 6,602,670 B2 | 8/2003 | Danenberg | ................ | 435/6 |
| 6,618,679 B2 | 9/2003 | Loehrlein et al. | ............ | 702/20 |
| 6,620,606 B2 | 9/2003 | Bandman et al. | .......... | 435/219 |
| 6,696,558 B2 | 2/2004 | Reed et al. | ................ | 536/23.5 |
| 6,716,575 B2 | 4/2004 | Plowman et al. | .......... | 435/6 |
| 6,750,013 B2 | 6/2004 | Gish et al. | ................ | 435/6 |
| 6,800,737 B2 | 10/2004 | Altieri | ................ | 530/386 |
| 6,943,150 B1 | 9/2005 | Altieri | ................ | 514/21 |
| 2001/0051344 A1* | 12/2001 | Shalon et al. | ............... | 435/6 |
| 2002/0004491 A1 | 1/2002 | Xu et al. | ................ | 514/44 |
| 2002/0009736 A1 | 1/2002 | Wang | ................ | 435/6 |
| 2002/0039764 A1 | 4/2002 | Rosen | ................ | 435/69.1 |
| 2002/0160395 A1 | 10/2002 | Altieri et al. | .............. | 435/6 |
| 2003/0073112 A1 | 4/2003 | Zhang et al. | .............. | 435/6 |
| 2003/0104499 A1 | 6/2003 | Pressman et al. | ............ | 435/7.23 |
| 2003/0143539 A1* | 7/2003 | Bertucci et al. | .............. | 435/6 |
| 2003/0165952 A1 | 9/2003 | Linnarsson et al. | ............ | 435/6 |
| 2003/0180791 A1 | 9/2003 | Chinnadurai | ................ | 435/6 |
| 2003/0198970 A1 | 10/2003 | Roberts | ................ | 435/6 |
| 2003/0198972 A1 | 10/2003 | Erlander et al. | .............. | 435/6 |
| 2003/0219771 A1 | 11/2003 | Bevilacqua et al. | .......... | 435/6 |
| 2003/0229455 A1 | 12/2003 | Bevilacqua et al. | .......... | 702/20 |
| 2004/0009489 A1 | 1/2004 | Golub et al. | ................ | 435/6 |
| 2004/0126775 A1 | 7/2004 | Altieri et al. | .............. | 435/6 |
| 2004/0133352 A1 | 7/2004 | Bevilacqua et al. | .......... | 702/19 |

FOREIGN PATENT DOCUMENTS

| | | |
|---|---|---|
| EP | 0 108 564 B1 | 5/1988 |
| EP | 1 365 034 | 11/2003 |
| WO | WO 99/02714 | 1/1999 |
| WO | WO9944062 A1 * | 9/1999 |
| WO | WO 00/50595 | 8/2000 |

(Continued)

OTHER PUBLICATIONS

Kroese et al (Genetics in Medicine, vol. 6, pp. 475-480, 2004).*

(Continued)

*Primary Examiner*—Kenneth R. Horlick
*Assistant Examiner*—Christopher M. Babic
(74) *Attorney, Agent, or Firm*—Carol L. Francis; Bozicevic, Field & Francis, LLP

(57) ABSTRACT

The present invention provides gene sets the expression of which is important in the diagnosis and/or prognosis of breast cancer.

20 Claims, No Drawings

FOREIGN PATENT DOCUMENTS

| WO | WO 00/55173 | 9/2000 |
|---|---|---|
| WO | WO 00/55180 | 9/2000 |
| WO | WO 02/103320 | 12/2000 |
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 01/75160 A1 | 10/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/10436 | 2/2002 |
| WO | WO 02/46467 | 6/2002 |
| WO | WO 02/46467 A2 | 6/2002 |
| WO | WO 02/017852 | 7/2002 |
| WO | WO 02/055988 | 7/2002 |
| WO | WO 02/059271 A2 | 8/2002 |
| WO | WO 02/059377 | 8/2002 |
| WO | WO 02/068579 | 9/2002 |
| WO | WO 03/011897 | 2/2003 |
| WO | WO 03/078662 A1 | 9/2003 |
| WO | WO 03/083096 | 10/2003 |

OTHER PUBLICATIONS

Lucentini (The Scientist, vol. 18, p. 20, 2004).*
Murphy et al. (Pathology, 2005, vol. 37(4), pp. 271-277).*
Korfee et al. (Current Pharmacogenomics, 2005. vol. 3, pp. 201-216).*
Search result of MYBL2.*
NCBI sequence of NM_002466 and description.*
Ahmad, Athar, et al., "Stromelysin 3: An Independent Prognostic Factor for Relapse: Free Survival in Node-Positive Breast Cancer and Demonstration Novel Breast Carcinoma Cell Expression", American Journal of Clinical Pathology, vol. 152, No. 3, pp. 721-728, Mar. 3, 1998.
Borresen-Dale, A. L. et al, "Genetic Profiling of Breast Cancer: From Molecular Portraits to Clinical Utility", The International Journal of Biological Markers, vol. 18, No. 1, pp. 54-56, Sep. 20, 2002.
Chenard, Marie-Pierre, et al., "High Levels of Stromelysin-3 Correlate with Poor Prognosis in Patients with Breast Carcinoma", The Journal of Molecular Diagnostics, vol. 69, No. 6, pp. 448-451, 1996.
Engel, Georg, et al., "Correlation Between Stromelysin-3 mRNA Level and Outcome of Human Breast Cancer", vol. 58, No. 6, pp. 830-835, 1994.
Forozan, Farahnaz, et al., "Comparative Genomic Hybridization Analysis of 38 Breast Cancer Cell Lines: A Basis for Interpreting Complementary DNA Microarray Data", Cancer Research, vol. 60, No. 16, pp. 4519-4525, Aug. 15, 2000.
Guérlin, Martine, et al. "Structure and Expression of cerbB2 and EGF Receptor Genes in Inflammatory and Non-Inflammatory Breast Cancer", International Journal Cancer, vol. 43, pp. 201-208, 1989.
Leek, Russell, et al., "Association of Macrophage Infiltration with Angiogenesis and Prognosis in Invasive Breast Carcinoma", Cancer Research, vol. 56, pp. 4625-4629, Oct. 15, 1996.
Murray, P. A., et al., "The Prognostic Significance of Transforming Growth Factors in Human Breast Cancer", British Journal of Cancer, vol. 67, No. 6, pp. 1408-1412, 1993.
Raschellá, Giuseppe, et al., "Expression of B-mhy in Neuroblastoma Tumors is a Poor Prognostic Factor Independent from MYCN Amplification", Cancer Research, vol. 59, pp. 3365-3368, Jul. 15, 1999.
Samuels-Lev, Yardena, et al., "ASPP Proteins Specifically Stimulate the Apoptotic Function of p53", Molecular Cell, vol. 8, pp. 781-794, Oct. 2001.
Schorr, Kristel, et al. "Bcl-2 Gene Family and Related Proteins in Mammary Gland Involution and Breast Cancer", Journal of Mammary Gland and Neoplasia, vol. 4, No. 2, pp. 153-164, Apr. 1999.

Sens, Mary Ann et al., "Metallothionein Isoform 3 Overexpression is Associated with Breast Cancers having a Poor Prognosis", American Journal of Pathology, vol. 159, No. 1, Jul. 2001.
Sgroi, Dennis C., et al., "In Vivo Gene Expression Profile Analysis of Human Breast Cancer Progression", Cancer Research, vol. 59, No. 22, pp. 5656-5661, Nov. 15, 1999.
Ueno, Takayuki et al., "Significance of Macrophage Chemoattractant Protein -1 in Macrophage Recruitment, Angiogenesis and Survival in Human Breast Cancer". Clinical Cancer Research, vol. 6, pp. 3282-3289, Aug. 2000.
van't Veer, Laura, et al. "Gene Expression Profiling Predicts Clinical Outcome of Breast Cancer", Nature, vol. 415, No. 6871, Jan. 31, 2002.
Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795, Nov. 20, 2001.
Golub et al., "Molecular Classification of Cancer: Class Discovery and Class Prediction by Gene Expression Monitoring", Science, vol. 286, pp. 531-537, Oct. 15, 1999.
Martin et al., "Linking Gene Expression Patterns to Therapeutic Groups in Breast Cancer", Cancer Research, vol. 60, pp. 2232-2238, Apr. 15, 2000.
Perou et al., "Molecular portraits of human breast tumors", Nature, vol. 406, pp. 747-752 (2000).
Ramaswamy et al., "Multiclass cancer diagnosis using tumor gene expression signatures", Proceedings of the National Academy of Sciences of USA, vol. 98, No. 26, pp. 15149-15154, Dec. 18, 2001.
Sorlie et al., "Gene Expression patterns of breast carcinomas distinguish tumor subclass with clinical implications", Proceedings of the National Academy of Sciences of USA, vol. 98, No. 19, pp. 10869-10874, Sep. 11, 2001.
West et al., "Predicting the clinical status of human breast cancer by using expression profiles", Proceedings of the National Academy of Sciences of USA, vol. 98, No. 20, pp. 11462-11467, Sep. 25, 2001.
Yan et al., "Dissecting Complex Epigenetic Alterations in Breast Cancer Using CpG Island Microarrays", Cancer Research, vol. 61, pp. 8375-7380, Dec. 1, 2001.
Yeang et al., "Molecular Classification of Multiple Tumor Types", Bioinformatics, vol. 17, Suppl: 1, pp. S316-S322 (2001).
Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.
Ding, Chunming, et al.; *A high-throughput gene expression analysis technique using competitive PCR and matrix-assisted laser desorption ionization time-of-flight MS,* PNAS, vol. 100:6; Mar. 18, 2003; pp. 3059-3064.
Cambridge Healthtech Institute Conference Agenda; "Enabling Molecular Profiling With Cellular Resolution: Microgenomics Using Homogeneous Cell Samples"; Dec. 2002; 5 pgs.
Yang, Li, et al.; *BADGE BeadsArray for the Detection of Gene Expression, a High-Throughput Diagnostic Bioassay;* Genome Research; vol. 11; 2001; pp. 1888-1898.
Bertucci, F., et al. Gene expression profiling of primary breast carcinomas using arrays of candidate genes. Human Molecular Genetics. 2000, vol. 9, No. 20, pp. 2981-1991.
Chenard, M., et al. High levels of stromelysin-3 correlate with poor prognosis in patients with breast carcinoma. International Journal of Cancer. 1996, vol. 69, pp. 448-451.
Engel, G., et al. Correlation between stromelysin-3 mRNA and outcome of human breast cancer. International Journal of Cancer. 1994, vol. 58, pp. 830-835.
Kononen, J., et al. Tissue microarrays for high-throughput molecular profiling of tumor specimens. Nature Medicine. 1998, vol. 4, No. 7, pp. 844-847.
Van De Vijver, M., et al. A gene-expression signature as a predictor of survival in breast cancer. The New England Journal of Medicine. 2002, vol. 347, No. 25, pp. 1999-2009.
Van't Veer, L., et al. Gene expression profiling predicts clinical outcome of breast cancer. Nature. 2002, vol. 415, pp. 530-536.

* cited by examiner

SEQUENCE LISTING

<160> NUMBER OF SEQ ID NOS: 440

<210> SEQ ID NO 1
<211> LENGTH: 81
<212> TYPE: DNA
<213> ORGANISM: Artificial Sequence
<220> FEATURE:
<223> OTHER INFORMATION: Amplicon

<400> SEQUENCE: 1
gcggcgagtt tccgatttaa agctgagctg cgaggaaaat ggcggcggga ggatcaaaat    60
acttgctgga tggtggactc a                                              81

<210> SEQ ID NO 2
<211> LENGTH: 71
<212> TYPE: DNA
<213> ORGANISM: Artificial Sequence
<220> FEATURE:
<223> OTHER INFORMATION: Amplicon

<400> SEQUENCE: 2
cgcttctatg gcgctgagat tgtgtcagcc ctggactacc tgcactcgga gaagaacgtg    60
gtgtaccggg a                                                         71

<210> SEQ ID NO 3
<211> LENGTH: 71
<212> TYPE: DNA
<213> ORGANISM: Artificial Sequence
<220> FEATURE:
<223> OTHER INFORMATION: Amplicon

<400> SEQUENCE: 3
tcctgccacc cttcaaacct caggtcacgt ccgaggtcga cacaaggtac ttcgatgatg    60
aatttaccgc c                                                         71

<210> SEQ ID NO 4
<211> LENGTH: 69
<212> TYPE: DNA
<213> ORGANISM: Artificial Sequence
<220> FEATURE:
<223> OTHER INFORMATION: Amplicon

<400> SEQUENCE: 4
ggacagcagg aatgtgtttc tccatacagg tcacggggag ccaatggttc agaaacaaat    60
cgagtgggt                                                            69

<210> SEQ ID NO 5
<211> LENGTH: 82
<212> TYPE: DNA
<213> ORGANISM: Artificial Sequence
<220> FEATURE:
<223> OTHER INFORMATION: Amplicon

<400> SEQUENCE: 5
tgtgagtgaa atgccttcta gtagtgaacc gtcctcggga gccgactatg actactcaga        60
agagtatgat aacgaaccac aa                                                 82

<210> SEQ ID NO 6
<211> LENGTH: 66
<212> TYPE: DNA
<213> ORGANISM: Artificial Sequence
<220> FEATURE:
<223> OTHER INFORMATION: amplicon

<400> SEQUENCE: 6
cagcagatgt ggatcagcaa gcaggagtat gacgagtccg gcccctccat cgtccaccgc        60
aaatgc                                                                   66

<210> SEQ ID NO 7
<211> LENGTH: 80
<212> TYPE: DNA
<213> ORGANISM: Artificial Sequence
<220> FEATURE:
<223> OTHER INFORMATION: Amplicon

<400> SEQUENCE: 7
ggctcttgtg cgtactgtcc ttcgggctgg tgacagggaa gacatcactg agcctgccat        60
ctgtgctctt cgtcatctga                                                    80

<210> SEQ ID NO 8
<211> LENGTH: 73
<212> TYPE: DNA
<213> ORGANISM: Artificial Sequence
<220> FEATURE:
<223> OTHER INFORMATION: Amplicon

<400> SEQUENCE: 8
gggtcaggtg cctcgagatc gggcttgggc ccagagcatg ttccagatcc cagagtttga        60
gccgagtgag cag                                                           73

<210> SEQ ID NO 9
<211> LENGTH: 81
<212> TYPE: DNA
<213> ORGANISM: Artificial Sequence
<220> FEATURE:
<223> OTHER INFORMATION: Amplicon

<400> SEQUENCE: 9
cgttgtcagc acttggaata caagatggtt gccgggtcat gttaattggg aaaaagaaca        60
gtccacagga agaggttgaa c                                                  81

<210> SEQ ID NO 10
<211> LENGTH: 83
<212> TYPE: DNA
<213> ORGANISM: Artificial Sequence
<220> FEATURE:
<223> OTHER INFORMATION: Amplicon

<400> SEQUENCE: 10
cctggagggt cctgtacaat ctcatcatgg gactcctgcc cttacccagg ggccacagag        60
cccccgagat ggagcccaat tag                                                83

<210> SEQ ID NO 11
<211> LENGTH: 73

<212> TYPE: DNA
<213> ORGANISM: Artificial Sequence
<220> FEATURE:
<223> OTHER INFORMATION: Amplicon

<400> SEQUENCE: 11
cagatggacc tagtacccac tgagatttcc acgccgaagg acagcgatgg gaaaaatgcc    60
cttaaatcat agg    73

<210> SEQ ID NO 12
<211> LENGTH: 72
<212> TYPE: DNA
<213> ORGANISM: Artificial Sequence
<220> FEATURE:
<223> OTHER INFORMATION: Amplicon

<400> SEQUENCE: 12
atcctagccc tggtttttgg cctccttttt gctgtcacca gcgtcgcgtt ccttgtgcag    60
atgagaaggc ag    72

<210> SEQ ID NO 13
<211> LENGTH: 84
<212> TYPE: DNA
<213> ORGANISM: Artificial Sequence
<220> FEATURE:
<223> OTHER INFORMATION: Amplicon

<400> SEQUENCE: 13
ttcaggttgt tgcaggagac catgtacatg actgtctcca ttattgatcg gttcatgcag    60
aataattgtg tgcccaagaa gatg    84

<210> SEQ ID NO 14
<211> LENGTH: 69
<212> TYPE: DNA
<213> ORGANISM: Artificial Sequence
<220> FEATURE:
<223> OTHER INFORMATION: Amplicon

<400> SEQUENCE: 14
gcatgttcgt ggcctctaag atgaaggaga ccatcccccct gacggccgag aagctgtgca    60
tctacaccg    69

<210> SEQ ID NO 15
<211> LENGTH: 71
<212> TYPE: DNA
<213> ORGANISM: Artificial Sequence
<220> FEATURE:
<223> OTHER INFORMATION: Amplicon

<400> SEQUENCE: 15
aaagaagatg atgaccgggt ttacccaaac tcaacgtgca agcctcggat tattgcacca    60
tccagaggct c    71

<210> SEQ ID NO 16
<211> LENGTH: 82
<212> TYPE: DNA
<213> ORGANISM: Artificial Sequence
<220> FEATURE:
<223> OTHER INFORMATION: Amplicon

<400> SEQUENCE: 16
atgctgtggc tccttcctaa ctggggcttt cttgacatgt aggttgcttg gtaataacct    60

```
ttttgtatat cacaatttgg gt                                          82

<210> SEQ ID NO 17
<211> LENGTH: 65
<212> TYPE: DNA
<213> ORGANISM: Artificial Sequence
<220> FEATURE:
<223> OTHER INFORMATION: Amplicon

<400> SEQUENCE: 17
agatgaagtg gaaggcgctt ttcaccgcgg ccatcctgca ggcacagttg ccgattacag    60
aggca                                                              65

<210> SEQ ID NO 18
<211> LENGTH: 74
<212> TYPE: DNA
<213> ORGANISM: Artificial Sequence
<220> FEATURE:
<223> OTHER INFORMATION: Amplicon

<400> SEQUENCE: 18
tggttcccag ccctgtgtcc acctccaagc ccagattcag attcgagtca tgtacacaac    60
ccagggtgga ggag                                                    74

<210> SEQ ID NO 19
<211> LENGTH: 64
<212> TYPE: DNA
<213> ORGANISM: Artificial Sequence
<220> FEATURE:
<223> OTHER INFORMATION: Amplicon

<400> SEQUENCE: 19
gggcgtggaa cagtttatct cagacatctg ccccaagaag gacgtactcg aaaccttcac    60
cgtg                                                               64

<210> SEQ ID NO 20
<211> LENGTH: 81
<212> TYPE: DNA
<213> ORGANISM: Artificial Sequence
<220> FEATURE:
<223> OTHER INFORMATION: Amplicon

<400> SEQUENCE: 20
tgagtgtccc ccggtatctt ccccgccctg ccaatcccga tgaaattgga aattttattg    60
atgaaaatct gaaagcggct g                                            81

<210> SEQ ID NO 21
<211> LENGTH: 77
<212> TYPE: DNA
<213> ORGANISM: Artificial Sequence
<220> FEATURE:
<223> OTHER INFORMATION: Amplicon

<400> SEQUENCE: 21
tgacaatcag cacacctgca ttccgcctc ggaagagggc ctgagctgca tgaataagga     60
tcacggctgt agtcaca                                                 77

<210> SEQ ID NO 22
<211> LENGTH: 82
<212> TYPE: DNA
<213> ORGANISM: Artificial Sequence
<220> FEATURE:
<223> OTHER INFORMATION: Amplicon
```

```
<400> SEQUENCE: 22
gataaattgg tacaagggat cagcttttcc cagcccacat gtcctgatca tatgcttttg      60
aatagtcagt tacttggcac cc                                              82

<210> SEQ ID NO 23
<211> LENGTH: 72
<212> TYPE: DNA
<213> ORGANISM: Artificial Sequence
<220> FEATURE:
<223> OTHER INFORMATION: Amplicon

<400> SEQUENCE: 23
tgcctgtggt gggaagctca gtaactggga accaaaggat gatgctatgt cagaacaccg      60
gaggcatttt cc                                                          72

<210> SEQ ID NO 24
<211> LENGTH: 86
<212> TYPE: DNA
<213> ORGANISM: Artificial Sequence
<220> FEATURE:
<223> OTHER INFORMATION: Amplicon

<400> SEQUENCE: 24
ggatatttcc gtggctctta ttcaaactct ccatcaaatc ctgtaaactc cagagcaaat      60
caagattttt ctgccttgat gagaag                                           86

<210> SEQ ID NO 25
<211> LENGTH: 86
<212> TYPE: DNA
<213> ORGANISM: Artificial Sequence
<220> FEATURE:
<223> OTHER INFORMATION: Amplicon

<400> SEQUENCE: 25
gacatttcca gtcctgcagt caatgcctct ctgccccacc ctttgttcag tgtggctggt      60
gccacgacaa atgtgtgcga tcggag                                           86

<210> SEQ ID NO 26
<211> LENGTH: 75
<212> TYPE: DNA
<213> ORGANISM: Artificial Sequence
<220> FEATURE:
<223> OTHER INFORMATION: Amplicon

<400> SEQUENCE: 26
ggcatcctgg cccaaagttt cccaaatcca ggcggctaga ggcccactgc ttcccaacta      60
ccagctgagg gggtc                                                       75

<210> SEQ ID NO 27
<211> LENGTH: 79
<212> TYPE: DNA
<213> ORGANISM: Artificial Sequence
<220> FEATURE:
<223> OTHER INFORMATION: Amplicon

<400> SEQUENCE: 27
tctgcagagt tggaagcact ctatggtgac atcgatgctg tggagctgta tcctgcccTT      60
ctggtagaaa agcctcggc                                                   79

<210> SEQ ID NO 28
```

```
<211> LENGTH: 74
<212> TYPE: DNA
<213> ORGANISM: Artificial Sequence
<220> FEATURE:
<223> OTHER INFORMATION: Amplicon

<400> SEQUENCE: 28
gggaggctta tctcactgag tgagcagaat ctggtagact gctctgggcc tcaaggcaat      60
gaaggctgca atgg                                                       74

<210> SEQ ID NO 29
<211> LENGTH: 67
<212> TYPE: DNA
<213> ORGANISM: Artificial Sequence
<220> FEATURE:
<223> OTHER INFORMATION: Amplicon

<400> SEQUENCE: 29
tgtctcactg agcgagcaga atctggtgga ctgttcgcgt cctcaaggca atcagggctg      60
caatggt                                                               67

<210> SEQ ID NO 30
<211> LENGTH: 77
<212> TYPE: DNA
<213> ORGANISM: Artificial Sequence
<220> FEATURE:
<223> OTHER INFORMATION: Amplicon

<400> SEQUENCE: 30
cgctgacatc atgaatgttc ctcgaccggc tggaggcgag tttggatatg acaaagacac      60
atcgttgctg aaagaga                                                    77

<210> SEQ ID NO 31
<211> LENGTH: 73
<212> TYPE: DNA
<213> ORGANISM: Artificial Sequence
<220> FEATURE:
<223> OTHER INFORMATION: Amplicon

<400> SEQUENCE: 31
cacaatggcg gctctgaaga gttggctgtc gcgcagcgta acttcattct tcaggtacag      60
acagtgtttg tgt                                                        73

<210> SEQ ID NO 32
<211> LENGTH: 84
<212> TYPE: DNA
<213> ORGANISM: Artificial Sequence
<220> FEATURE:
<223> OTHER INFORMATION: Amplicon

<400> SEQUENCE: 32
ctctgagaca gtgcttcgat gactttgcag acttggtgcc ctttgactcc tgggagccgc      60
tcatgaggaa gttgggcctc atgg                                            84

<210> SEQ ID NO 33
<211> LENGTH: 62
<212> TYPE: DNA
<213> ORGANISM: Artificial Sequence
<220> FEATURE:
<223> OTHER INFORMATION: Amplicon

<400> SEQUENCE: 33
tgtcgatgga cttccagaac cacctgggca gctgccaaaa gtgtgatcca agctgtccca      60
```

```
at                                                               62

<210> SEQ ID NO 34
<211> LENGTH: 82
<212> TYPE: DNA
<213> ORGANISM: Artificial Sequence
<220> FEATURE:
<223> OTHER INFORMATION: Amplicon

<400> SEQUENCE: 34
gatctaagat ggcgactgtc gaaccggaaa ccacccctac tcctaatccc ccgactacag    60
aagaggagaa aacggaatct aa                                              82

<210> SEQ ID NO 35
<211> LENGTH: 68
<212> TYPE: DNA
<213> ORGANISM: Artificial Sequence
<220> FEATURE:
<223> OTHER INFORMATION: Amplicon

<400> SEQUENCE: 35
ggcagtgtca ctgagtcctt gaaatcctcc cctgccccgc gggtctctgg attgggacgc    60
acagtgca                                                              68

<210> SEQ ID NO 36
<211> LENGTH: 75
<212> TYPE: DNA
<213> ORGANISM: Artificial Sequence
<220> FEATURE:
<223> OTHER INFORMATION: Amplicon

<400> SEQUENCE: 36
gggccctcca gaacaatgat gggctttatg atcctgactg cgatgagagc gggctcttta    60
aggccaagca gtgca                                                      75

<210> SEQ ID NO 37
<211> LENGTH: 76
<212> TYPE: DNA
<213> ORGANISM: Artificial Sequence
<220> FEATURE:
<223> OTHER INFORMATION: Amplicon

<400> SEQUENCE: 37
accgtaggct ctgctctgaa tgactctcct gtgggtctgg ctgcctatat tctagagaag    60
ttttccacct ggacca                                                     76

<210> SEQ ID NO 38
<211> LENGTH: 81
<212> TYPE: DNA
<213> ORGANISM: Artificial Sequence
<220> FEATURE:
<223> OTHER INFORMATION: Amplicon

<400> SEQUENCE: 38
cggttatgtc atgccagata cacacctcaa aggtactccc tcctcccggg aaggcaccct    60
ttcttcagtg ggtctcagtt c                                               81

<210> SEQ ID NO 39
<211> LENGTH: 68
<212> TYPE: DNA
<213> ORGANISM: Artificial Sequence
<220> FEATURE:
```

```
<223> OTHER INFORMATION: Amplicon

<400> SEQUENCE: 39
cgtggtgccc ctctatgacc tgctgctgga gatgctggac gcccaccgcc tacatgcgcc      60
cactagcc                                                               68

<210> SEQ ID NO 40
<211> LENGTH: 90
<212> TYPE: DNA
<213> ORGANISM: Artificial Sequence
<220> FEATURE:
<223> OTHER INFORMATION: Amplicon

<400> SEQUENCE: 40
ggctattcct cattttctct acaaagtggc ctcagtgaac atgaagaagg tagcctcctg      60
gaggagaatt tcggtgacag tctacaatcc                                       90

<210> SEQ ID NO 41
<211> LENGTH: 68
<212> TYPE: DNA
<213> ORGANISM: Artificial Sequence
<220> FEATURE:
<223> OTHER INFORMATION: Amplicon

<400> SEQUENCE: 41
cggtagtcaa gtccggatca agggcaagga gacggaattc tacctgtgca tgaaccgcaa      60
aggcaagc                                                               68

<210> SEQ ID NO 42
<211> LENGTH: 74
<212> TYPE: DNA
<213> ORGANISM: Artificial Sequence
<220> FEATURE:
<223> OTHER INFORMATION: Amplicon

<400> SEQUENCE: 42
cacgggacat tcaccacatc gactactata aaaagacaac caacggccga ctgcctgtga      60
agtggatggc accc                                                        74

<210> SEQ ID NO 43
<211> LENGTH: 67
<212> TYPE: DNA
<213> ORGANISM: Artificial Sequence
<220> FEATURE:
<223> OTHER INFORMATION: Amplicon

<400> SEQUENCE: 43
ccagtggagc gcttccatga cctgcgtcct gatgaagtgg ccgatttgtt tcagacgacc      60
cagagag                                                                67

<210> SEQ ID NO 44
<211> LENGTH: 75
<212> TYPE: DNA
<213> ORGANISM: Artificial Sequence
<220> FEATURE:
<223> OTHER INFORMATION: Amplicon

<400> SEQUENCE: 44
ttggtacctg tgggttagca tcaagttctc cccagggtag aattcaatca gagctccagt      60
ttgcatttgg atgtg                                                       75
```

<210> SEQ ID NO 45
<211> LENGTH: 68
<212> TYPE: DNA
<213> ORGANISM: Artificial Sequence
<220> FEATURE:
<223> OTHER INFORMATION: Amplicon

<400> SEQUENCE: 45
tcagcagcaa gggcatcatg gaggaggatg aggcctgcgg gcgccagtac acgctcaaga    60
aaaccacc                                                              68

<210> SEQ ID NO 46
<211> LENGTH: 74
<212> TYPE: DNA
<213> ORGANISM: Artificial Sequence
<220> FEATURE:
<223> OTHER INFORMATION: Amplicon

<400> SEQUENCE: 46
attccaccca tggcaaattc catggcaccg tcaaggctga gaacgggaag cttgtcatca    60
atggaaatcc catc                                                       74

<210> SEQ ID NO 47
<211> LENGTH: 75
<212> TYPE: DNA
<213> ORGANISM: Artificial Sequence
<220> FEATURE:
<223> OTHER INFORMATION: Amplicon

<400> SEQUENCE: 47
caaaggagct cactgtggtg tctgtgttcc aaccactgaa tctggacccc atctgtgaat    60
aagccattct gactc                                                      75

<210> SEQ ID NO 48
<211> LENGTH: 67
<212> TYPE: DNA
<213> ORGANISM: Artificial Sequence
<220> FEATURE:
<223> OTHER INFORMATION: Amplicon

<400> SEQUENCE: 48
ccatctgcat ccatcttgtt tgggctcccc acccttgaga agtgcctcag ataatalccct    60 ggtggcc                                                               67

<210> SEQ ID NO 49
<211> LENGTH: 73
<212> TYPE: DNA
<213> ORGANISM: Artificial Sequence
<220> FEATURE:
<223> OTHER INFORMATION: Amplicon

<400> SEQUENCE: 49
cgaaaagatg ctgaacagtg acaaatccaa ctgaccagaa gggaggagga agctcactgg    60
tggctgttcc tga                                                        73

<210> SEQ ID NO 50
<211> LENGTH: 86
<212> TYPE: DNA
<213> ORGANISM: Artificial Sequence
<220> FEATURE:
<223> OTHER INFORMATION: Amplicon

<400> SEQUENCE: 50
aagctatgag gaaaagaagt acacgatggg ggacgctcct gattatgaca gaagccagtg    60
gctgaatgaa aaattcaagc tgggcc    86

<210> SEQ ID NO 51
<211> LENGTH: 73
<212> TYPE: DNA
<213> ORGANISM: Artificial Sequence
<220> FEATURE:
<223> OTHER INFORMATION: Amplicon

<400> SEQUENCE: 51
cccactcagt agccaagtca caatgtttgg aaaacagccc gtttacttga gcaagactga    60
taccacctgc gtg    73

<210> SEQ ID NO 52
<211> LENGTH: 70
<212> TYPE: DNA
<213> ORGANISM: Artificial Sequence
<220> FEATURE:
<223> OTHER INFORMATION: Amplicon

<400> SEQUENCE: 52
cggtgtgaga agtgcagcaa gccctgtgcc cgagtgtgct atggtctggg catggagcac    60
ttgcgagagg    70

<210> SEQ ID NO 53
<211> LENGTH: 82
<212> TYPE: DNA
<213> ORGANISM: Artificial Sequence
<220> FEATURE:
<223> OTHER INFORMATION: Amplicon

<400> SEQUENCE: 53
tgaacataaa gtctgcaaca tggaaggtat tgcactgcac aggccacatt cacgtatatg    60
ataccaacag taaccaacct ca    82

<210> SEQ ID NO 54
<211> LENGTH: 73
<212> TYPE: DNA
<213> ORGANISM: Artificial Sequence
<220> FEATURE:
<223> OTHER INFORMATION: Amplicon

<400> SEQUENCE: 54
tccaggatgt taggaactgt gaagatggaa gggcatgaaa ccagcgactg gaacagctac    60
tacgcagaca cgc    73

<210> SEQ ID NO 55
<211> LENGTH: 70
<212> TYPE: DNA
<213> ORGANISM: Artificial Sequence
<220> FEATURE:
<223> OTHER INFORMATION: Amplicon

<400> SEQUENCE: 55
agaaccgcaa ggtgagcaag gtggagattc tccagcacgt catcgactac atcagggacc    60
ttcagttgga    70

<210> SEQ ID NO 56
<211> LENGTH: 76
<212> TYPE: DNA
<213> ORGANISM: Artificial Sequence

```
<220> FEATURE:
<223> OTHER INFORMATION: Amplicon

<400> SEQUENCE: 56
tccggagctg tgatctaagg aggctggaga tgtattgcgc acccctcaag cctgccaagt      60
cagctcgctc tgtccg                                                      76

<210> SEQ ID NO 57
<211> LENGTH: 83
<212> TYPE: DNA
<213> ORGANISM: Artificial Sequence
<220> FEATURE:
<223> OTHER INFORMATION: Amplicon

<400> SEQUENCE: 57
gcatggtagc cgaagatttc acagtcaaaa tcggagattt ggtatgacg cgagatatct       60 atgagacaga ctattaccgg aaa                                              83

<210> SEQ ID NO 58
<211> LENGTH: 73
<212> TYPE: DNA
<213> ORGANISM: Artificial Sequence
<220> FEATURE:
<223> OTHER INFORMATION: Amplicon

<400> SEQUENCE: 58
gtggacagca ccatgaacat gttgggcggg ggaggcagtg ctggccggaa gcccctcaag      60
tcgggtatga agg                                                         73

<210> SEQ ID NO 59
<211> LENGTH: 72
<212> TYPE: DNA
<213> ORGANISM: Artificial Sequence
<220> FEATURE:
<223> OTHER INFORMATION: Amplicon

<400> SEQUENCE: 59
cctgaacctt ccaaagatgg ctgaaaaaga tggatgcttc caatctggat tcaatgagga      60
gacttgcctg gt                                                          72

<210> SEQ ID NO 60
<211> LENGTH: 74
<212> TYPE: DNA
<213> ORGANISM: Artificial Sequence
<220> FEATURE:
<223> OTHER INFORMATION: Amplicon

<400> SEQUENCE: 60
ccacagctca ccttctgtca ggtgtccatc ccagctccag ccagctccca gagaggaaga      60
gactggcact gagg                                                        74

<210> SEQ ID NO 61
<211> LENGTH: 80
<212> TYPE: DNA
<213> ORGANISM: Artificial Sequence
<220> FEATURE:
<223> OTHER INFORMATION: Amplicon

<400> SEQUENCE: 61
cggactttgg gtgcgacttg acgagcggtg gttcgacaag tggccttgcg ggccggatcg      60
tcccagtgga agagttgtaa                                                  80
```

<210> SEQ ID NO 62
<211> LENGTH: 78
<212> TYPE: DNA
<213> ORGANISM: Artificial Sequence
<220> FEATURE:
<223> OTHER INFORMATION: Amplicon

<400> SEQUENCE: 62
gcccagaggc tccatcgtcc atcctcttcc tccccagtcg gctgaactct cccttgtct        60 gcactgttca aacctctg                                                     78

<210> SEQ ID NO 63
<211> LENGTH: 83
<212> TYPE: DNA
<213> ORGANISM: Artificial Sequence
<220> FEATURE:
<223> OTHER INFORMATION: Amplicon

<400> SEQUENCE: 63
ggcctgctga gatcaaagac tacagtccct acttcaagac cattgaggac ctgaggaaca       60
agattctcac agccacagtg gac                                              83

<210> SEQ ID NO 64
<211> LENGTH: 73
<212> TYPE: DNA
<213> ORGANISM: Artificial Sequence
<220> FEATURE:
<223> OTHER INFORMATION: Amplicon

<400> SEQUENCE: 64
cgaggattgg ttcttcagca agacaggga actgaaccgc gaggtggcca ccaacagtga       60
gctggtgcag agt                                                        73

<210> SEQ ID NO 65
<211> LENGTH: 68
<212> TYPE: DNA
<213> ORGANISM: Artificial Sequence
<220> FEATURE:
<223> OTHER INFORMATION: Amplicon

<400> SEQUENCE: 65
agagatcgag gctctcaagg aggagctgct cttcatgaag aagaaccacg aagaggaagt       60
aaaaggcc                                                              68

<210> SEQ ID NO 66
<211> LENGTH: 77
<212> TYPE: DNA
<213> ORGANISM: Artificial Sequence
<220> FEATURE:
<223> OTHER INFORMATION: Amplicon

<400> SEQUENCE: 66
tgagcggcag aatcaggagt accagcggct catggacatc aagtcgcggc tggagcagga      60
gattgccacc taccgca                                                    77

<210> SEQ ID NO 67
<211> LENGTH: 69
<212> TYPE: DNA
<213> ORGANISM: Artificial Sequence
<220> FEATURE:
<223> OTHER INFORMATION: Amplicon

<400> SEQUENCE: 67

```
tcagtggaga aggagttgga ccagtcaaca tctctgttgt cacaagcagt gtttcctctg      60
gatatggca                                                             69

<210> SEQ ID NO 68
<211> LENGTH: 86
<212> TYPE: DNA
<213> ORGANISM: Artificial Sequence
<220> FEATURE:
<223> OTHER INFORMATION: Amplicon

<400> SEQUENCE: 68
ggatgaagct tacatgaaca aggtagagct ggagtctcgc ctggaagggc tgaccgacga      60
gatcaacttc ctcaggcagc tatatg                                          86

<210> SEQ ID NO 69
<211> LENGTH: 83
<212> TYPE: DNA
<213> ORGANISM: Artificial Sequence
<220> FEATURE:
<223> OTHER INFORMATION: Amplicon

<400> SEQUENCE: 69
ggaaagacca cctgaaaaac cacctccaga cccacgaccc caacaaaatg gcctttgggt      60
gtgaggagtg tgggaagaag tac                                             83

<210> SEQ ID NO 70
<211> LENGTH: 77
<212> TYPE: DNA
<213> ORGANISM: Artificial Sequence
<220> FEATURE:
<223> OTHER INFORMATION: Amplicon

<400> SEQUENCE: 70
cagatggcca ctttgagaac attttagctg acaacagtgt gaacgaccag accaaaatcc      60
ttgtggttaa tgctgcc                                                    77

<210> SEQ ID NO 71
<211> LENGTH: 75
<212> TYPE: DNA
<213> ORGANISM: Artificial Sequence
<220> FEATURE:
<223> OTHER INFORMATION: Amplicon

<400> SEQUENCE: 71 gactttgcc cgctaccttt cattccggcg tgacaacaat gagctgttgc tcttcatact       60
gaagcagtta gtggc                                                      75

<210> SEQ ID NO 72
<211> LENGTH: 75
<212> TYPE: DNA
<213> ORGANISM: Artificial Sequence
<220> FEATURE:
<223> OTHER INFORMATION: Amplicon

<400> SEQUENCE: 72
ggagaacaat ccccttgaga cagaatatgg cctttctgtc tacaaggatc accagaccat      60
caccatccag gagat                                                      75

<210> SEQ ID NO 73
<211> LENGTH: 82
<212> TYPE: DNA
```

```
<213> ORGANISM: Artificial Sequence
<220> FEATURE:
<223> OTHER INFORMATION: Amplicon

<400> SEQUENCE: 73
tgatggtcct atgtgtcaca ttcatcacag gtttcatacc aacacaggct tcagcacttc    60
ctttggtgtg tttcctgtcc ca                                            82

<210> SEQ ID NO 74
<211> LENGTH: 68
<212> TYPE: DNA
<213> ORGANISM: Artificial Sequence
<220> FEATURE:
<223> OTHER INFORMATION: Amplicon

<400> SEQUENCE: 74
ctacagggac gccatcgaat ccggatcttg atgctggtgt aagtgaacat tcaggtgatt    60
ggttggat                                                            68

<210> SEQ ID NO 75
<211> LENGTH: 67
<212> TYPE: DNA
<213> ORGANISM: Artificial Sequence
<220> FEATURE:
<223> OTHER INFORMATION: Amplicon

<400> SEQUENCE: 75
gagaaccaat ctcaccgaca ggcagctggc agaggaatac ctgtaccgct atggttacac    60
tcgggtg                                                             67

<210> SEQ ID NO 76
<211> LENGTH: 77
<212> TYPE: DNA
<213> ORGANISM: Artificial Sequence
<220> FEATURE:
<223> OTHER INFORMATION: Amplicon

<400> SEQUENCE: 76
ccgccctcac ctgaagagaa acgcgctcct tggcggacac tgggggagga gaggaagaag    60
cgcggctaac ttattcc                                                  77

<210> SEQ ID NO 77
<211> LENGTH: 74
<212> TYPE: DNA
<213> ORGANISM: Artificial Sequence
<220> FEATURE:
<223> OTHER INFORMATION: Amplicon

<400> SEQUENCE: 77
gccgagatcg ccaagatgtt gccagggagg acagacaatg ctgtgaagaa tcactggaac    60
tctaccatca aaag                                                     74

<210> SEQ ID NO 78
<211> LENGTH: 72
<212> TYPE: DNA
<213> ORGANISM: Artificial Sequence
<220> FEATURE:
<223> OTHER INFORMATION: Amplicon

<400> SEQUENCE: 78
ccctcgtgct gatgctactg aggagccagc gtctagggca gcagccgctt cctagaagac    60
caggtcatga tg                                                       72
```

<210> SEQ ID NO 79
<211> LENGTH: 66
<212> TYPE: DNA
<213> ORGANISM: Artificial Sequence
<220> FEATURE:
<223> OTHER INFORMATION: Amplicon

<400> SEQUENCE: 79
cggtggacca cgaagagtta acccgggact tggagaagca ctgcagagac atggaagagg   60
cgagcc                                                              66

<210> SEQ ID NO 80
<211> LENGTH: 68
<212> TYPE: DNA
<213> ORGANISM: Artificial Sequence
<220> FEATURE:
<223> OTHER INFORMATION: Amplicon

<400> SEQUENCE: 80
ctttgaaccc ttgcttgcaa taggtgtgcg tcagaagcac ccaggacttc catttgcttt   60
gtcccggg                                                            68

<210> SEQ ID NO 81
<211> LENGTH: 81
<212> TYPE: DNA
<213> ORGANISM: Artificial Sequence
<220> FEATURE:
<223> OTHER INFORMATION: Amplicon

<400> SEQUENCE: 81
ccgcaacgtg gttttctcac cctatggggt ggcctcggtg ttggccatgc tccagctgac   60
aacaggagga gaaacccagc a                                             81

<210> SEQ ID NO 82
<211> LENGTH: 66
<212> TYPE: DNA
<213> ORGANISM: Artificial Sequence
<220> FEATURE:
<223> OTHER INFORMATION: Amplicon

<400> SEQUENCE: 82
ccagctctcc ttccagctac agatcaatgt ccctgtccga gtgctggagc taagtgagag   60
ccaccc                                                              66

<210> SEQ ID NO 83
<211> LENGTH: 83
<212> TYPE: DNA
<213> ORGANISM: Artificial Sequence
<220> FEATURE:
<223> OTHER INFORMATION: Amplicon

<400> SEQUENCE: 83
ataccaatca ccgcacaaac ccaggctatt tgttaagtcc agtcacagcg caaagaaaca   60
tatgcggaga aaatgctagt gtg                                           83

<210> SEQ ID NO 84
<211> LENGTH: 62
<212> TYPE: DNA
<213> ORGANISM: Artificial Sequence
<220> FEATURE:
<223> OTHER INFORMATION: Amplicon

```
<400> SEQUENCE: 84
gccatccgca aaggctttct cgcttgtcac cttgccatgt ggaagaaact ggcggaatgg      60
cc                                                                    62

<210> SEQ ID NO 85
<211> LENGTH: 85
<212> TYPE: DNA
<213> ORGANISM: Artificial Sequence
<220> FEATURE:
<223> OTHER INFORMATION: Amplicon

<400> SEQUENCE: 85
gcatcaggct gtcattatgg tgtccttacc tgtgggagct gtaaggtctt ctttaagagg      60
gcaatggaag ggcagcacaa ctact                                           85

<210> SEQ ID NO 86
<211> LENGTH: 66
<212> TYPE: DNA
<213> ORGANISM: Artificial Sequence
<220> FEATURE:
<223> OTHER INFORMATION: Amplicon

<400> SEQUENCE: 86
tctccatatc tgccttgcag agtctcctgc agcacctcat cgggctgagc aatctgaccc      60
acgtgc                                                                66

<210> SEQ ID NO 87
<211> LENGTH: 86
<212> TYPE: DNA
<213> ORGANISM: Artificial Sequence
<220> FEATURE:
<223> OTHER INFORMATION: Amplicon

<400> SEQUENCE: 87
gccctcccag tgtgcaaata agggctgctg tttcgacgac accgttcgtg gggtcccctg      60
gtgcttctat cctaatacca tcgacg                                          86

<210> SEQ ID NO 88
<211> LENGTH: 78
<212> TYPE: DNA
<213> ORGANISM: Artificial Sequence
<220> FEATURE:
<223> OTHER INFORMATION: Amplicon

<400> SEQUENCE: 88
gaacttcttg agcaggagca tacccagggc ttcataatca ccttctgttc agcactagat      60
gatattcttg ggggtgga                                                   78

<210> SEQ ID NO 89
<211> LENGTH: 77
<212> TYPE: DNA
<213> ORGANISM: Artificial Sequence
<220> FEATURE:
<223> OTHER INFORMATION: Amplicon

<400> SEQUENCE: 89
cgaagccctt acaagtttcc tagttcaccc ttacggattc ctggagggaa catctatatt      60
tcacccctga agagtcc                                                    77

<210> SEQ ID NO 90
<211> LENGTH: 74
```

<212> TYPE: DNA
<213> ORGANISM: Artificial Sequence
<220> FEATURE:
<223> OTHER INFORMATION: Amplicon

<400> SEQUENCE: 90
ccagacgagc gattagaagc ggcagcttgt gaggtgaatg atttggggga agaggaggag    60
gaggaagagg agga                                                      74

<210> SEQ ID NO 91
<211> LENGTH: 69
<212> TYPE: DNA
<213> ORGANISM: Artificial Sequence
<220> FEATURE:
<223> OTHER INFORMATION: Amplicon

<400> SEQUENCE: 91
catcttccag gaggaccact ctctgtggca ccctggacta cctgcccct gaaatgattg     60 aaggtcgga                                                            69

<210> SEQ ID NO 92
<211> LENGTH: 90
<212> TYPE: DNA
<213> ORGANISM: Artificial Sequence
<220> FEATURE:
<223> OTHER INFORMATION: Amplicon

<400> SEQUENCE: 92
cctggaggct gcaacatacc tcaatcctgt cccaggccgg atcctcctga agccctttc    60 gcagcactgc tatcctccaa agccattgta                                     90

<210> SEQ ID NO 93
<211> LENGTH: 80
<212> TYPE: DNA
<213> ORGANISM: Artificial Sequence
<220> FEATURE:
<223> OTHER INFORMATION: Amplicon

<400> SEQUENCE: 93
tgttttgatt cccgggctta ccaggtgaga agtgagggag gaagaaggca gtgtcccttt    60
tgctagagct gacagctttg                                                80

<210> SEQ ID NO 94
<211> LENGTH: 65
<212> TYPE: DNA
<213> ORGANISM: Artificial Sequence
<220> FEATURE:
<223> OTHER INFORMATION: Amplicon

<400> SEQUENCE: 94
gcccgaaacg ccgaatataa tcccaagcgg tttgctgcgg taatcatgag gataagagag    60
ccacg                                                                65

<210> SEQ ID NO 95
<211> LENGTH: 83
<212> TYPE: DNA
<213> ORGANISM: Artificial Sequence
<220> FEATURE:
<223> OTHER INFORMATION: Amplicon

<400> SEQUENCE: 95
ggtgtgccac agaccttcct acttggcctg taatcacctg tgcagccttt tgtgggcctt    60
caaaactctg tcaagaactc cgt                                                   83

<210> SEQ ID NO 96
<211> LENGTH: 75
<212> TYPE: DNA
<213> ORGANISM: Artificial Sequence
<220> FEATURE:
<223> OTHER INFORMATION: Amplicon

<400> SEQUENCE: 96
tccctgcggt cccagatagc ctgaatcctg cccggagtgg aactgaagcc tgcacagtgt      60
ccaccctgtt cccac                                                        75

<210> SEQ ID NO 97
<211> LENGTH: 72
<212> TYPE: DNA
<213> ORGANISM: Artificial Sequence
<220> FEATURE:
<223> OTHER INFORMATION: Amplicon

<400> SEQUENCE: 97
aatccaaggg ggagagtgat gacttccata tggactttga ctcagctgtg gctcctcggg      60
caaaatctgt ac                                                           72

<210> SEQ ID NO 98
<211> LENGTH: 66
<212> TYPE: DNA
<213> ORGANISM: Artificial Sequence
<220> FEATURE:
<223> OTHER INFORMATION: Amplicon

<400> SEQUENCE: 98
tgtggacatc ttccctcag acttccctac tgagccacct tctctgccac gaaccggtcg        60
ggctag                                                                  66

<210> SEQ ID NO 99
<211> LENGTH: 82
<212> TYPE: DNA
<213> ORGANISM: Artificial Sequence
<220> FEATURE:
<223> OTHER INFORMATION: Amplicon

<400> SEQUENCE: 99
ctatatgcag ccagagatgt gacagccacc gtggacagcc tgccactcat cacagcctcc      60
attctcagta agaaactcgt gg                                                82

<210> SEQ ID NO 100
<211> LENGTH: 81
<212> TYPE: DNA
<213> ORGANISM: Artificial Sequence
<220> FEATURE:
<223> OTHER INFORMATION: Amplicon

<400> SEQUENCE: 100
gggccaaata ttcagaagct tttatatcag aggaccacca tagcggccat ggagaccatc      60
tctgtcccat catacccatc c                                                 81

<210> SEQ ID NO 101
<211> LENGTH: 73
<212> TYPE: DNA
<213> ORGANISM: Artificial Sequence
<220> FEATURE:
<223> OTHER INFORMATION: Amplicon

<400> SEQUENCE: 101
cttcacagtg ctcctgcagt ctctctgtgt ggctgtaact tacgtgtact ttaccaacga    60
gctgaagcag atg                                                       73

<210> SEQ ID NO 102
<211> LENGTH: 65
<212> TYPE: DNA
<213> ORGANISM: Artificial Sequence
<220> FEATURE:
<223> OTHER INFORMATION: Amplicon

<400> SEQUENCE: 102
gcctcggtgt gcctttcaac atcgccagct acgccctgct cacgtacatg attgcgcaca    60
tcacg                                                                65

<210> SEQ ID NO 103
<211> LENGTH: 70
<212> TYPE: DNA
<213> ORGANISM: Artificial Sequence
<220> FEATURE:
<223> OTHER INFORMATION: Amplicon

<400> SEQUENCE: 103
gtggatgtgc cctgaaggac aagccaggcg tctacacgag agtctcacac ttcttaccct    60
ggatccgcag                                                           70

<210> SEQ ID NO 104
<211> LENGTH: 67
<212> TYPE: DNA
<213> ORGANISM: Artificial Sequence
<220> FEATURE:
<223> OTHER INFORMATION: Amplicon

<400> SEQUENCE: 104
gccctggatt tcagaaagag ccaagtctgg atctgggacc ctttccttcc ttccctggct    60
tgtaact                                                              67

<210> SEQ ID NO 105
<211> LENGTH: 71
<212> TYPE: DNA
<213> ORGANISM: Artificial Sequence
<220> FEATURE:
<223> OTHER INFORMATION: Amplicon

<400> SEQUENCE: 105
ctgctgtctt gggtgcattg gagccttgcc ttgctgctct acctccacca tgccaagtgg    60
tcccaggctg c                                                         71

<210> SEQ ID NO 106
<211> LENGTH: 71
<212> TYPE: DNA
<213> ORGANISM: Artificial Sequence
<220> FEATURE:
<223> OTHER INFORMATION: Amplicon

<400> SEQUENCE: 106
tgacgatggc ctggagtgtg tgcccactgg gcagcaccaa gtccggatgc agatcctcat    60
gatccggtac c                                                         71

<210> SEQ ID NO 107

```
<211> LENGTH: 75
<212> TYPE: DNA
<213> ORGANISM: Artificial Sequence
<220> FEATURE:
<223> OTHER INFORMATION: Amplicon

<400> SEQUENCE: 107
agaggcatcc atgaacttca cacttgcggg ctgcatcagc acacgctcct atcaacccaa      60
gtactgtgga gtttg                                                      75

<210> SEQ ID NO 108
<211> LENGTH: 77
<212> TYPE: DNA
<213> ORGANISM: Artificial Sequence
<220> FEATURE:
<223> OTHER INFORMATION: Amplicon

<400> SEQUENCE: 108
gcagttggaa gacacaggaa agtatcccca aattgcagat ttatcaacgg cttttatctt      60
gaaaatagtg ccacgca                                                    77

<210> SEQ ID NO 109
<211> LENGTH: 76
<212> TYPE: DNA
<213> ORGANISM: Artificial Sequence
<220> FEATURE:
<223> OTHER INFORMATION: Amplicon

<400> SEQUENCE: 109
agactgtgga gtttgatgtt gttgaaggag aaaagggtgc ggaggcagca aatgttacag      60
gtcctggtgg tgttcc                                                     76

<210> SEQ ID NO 110
<211> LENGTH: 70
<212> TYPE: DNA
<213> ORGANISM: Artificial Sequence
<220> FEATURE:
<223> OTHER INFORMATION: Amplicon

<400> SEQUENCE: 110
acccagtagc aaggagaagc ccactcactg ctccgagtgc ggcaaagctt tcagaaccta      60
ccaccagctg                                                            70

<210> SEQ ID NO 111
<211> LENGTH: 19
<212> TYPE: DNA
<213> ORGANISM: Artificial Sequence
<220> FEATURE:
<223> OTHER INFORMATION: forward primer

<400> SEQUENCE: 111
gcggcgagtt tccgattta                                                  19

<210> SEQ ID NO 112
<211> LENGTH: 21
<212> TYPE: DNA
<213> ORGANISM: Artificial Sequence
<220> FEATURE:
<223> OTHER INFORMATION: reverse primer

<400> SEQUENCE: 112
tgagtccacc atccagcaag t                                               21
```

```
<210> SEQ ID NO 113
<211> LENGTH: 21
<212> TYPE: DNA
<213> ORGANISM: Artificial Sequence
<220> FEATURE:
<223> OTHER INFORMATION: probe

<400> SEQUENCE: 113
atggcggcgg gaggatcaaa a                                              21

<210> SEQ ID NO 114
<211> LENGTH: 20
<212> TYPE: DNA
<213> ORGANISM: Artificial Sequence
<220> FEATURE:
<223> OTHER INFORMATION: forward primer

<400> SEQUENCE: 114
cgcttctatg gcgctgagat                                                20

<210> SEQ ID NO 115
<211> LENGTH: 20
<212> TYPE: DNA
<213> ORGANISM: Artificial Sequence
<220> FEATURE:
<223> OTHER INFORMATION: reverse primer

<400> SEQUENCE: 115
tcccggtaca ccacgttctt                                                20

<210> SEQ ID NO 116
<211> LENGTH: 24
<212> TYPE: DNA
<213> ORGANISM: Artificial Sequence
<220> FEATURE:
<223> OTHER INFORMATION: probe

<400> SEQUENCE: 116
cagccctgga ctacctgcac tcgg                                           24

<210> SEQ ID NO 117
<211> LENGTH: 19
<212> TYPE: DNA
<213> ORGANISM: Artificial Sequence
<220> FEATURE:
<223> OTHER INFORMATION: forward primer

<400> SEQUENCE: 117
tcctgccacc cttcaaacc                                                 19

<210> SEQ ID NO 118
<211> LENGTH: 21
<212> TYPE: DNA
<213> ORGANISM: Artificial Sequence
<220> FEATURE:
<223> OTHER INFORMATION: reverse primer

<400> SEQUENCE: 118
ggcggtaaat tcatcatcga a                                              21

<210> SEQ ID NO 119
<211> LENGTH: 24
<212> TYPE: DNA
<213> ORGANISM: Artificial Sequence
<220> FEATURE:
<223> OTHER INFORMATION: probe
```

<400> SEQUENCE: 119
caggtcacgt ccgaggtcga caca                                            24

<210> SEQ ID NO 120
<211> LENGTH: 20
<212> TYPE: DNA
<213> ORGANISM: Artificial Sequence
<220> FEATURE:
<223> OTHER INFORMATION: forward primer

<400> SEQUENCE: 120
ggacagcagg aatgtgtttc                                                 20

<210> SEQ ID NO 121
<211> LENGTH: 20
<212> TYPE: DNA
<213> ORGANISM: Artificial Sequence
<220> FEATURE:
<223> OTHER INFORMATION: reverse primer

<400> SEQUENCE: 121
acccactcga tttgtttctg                                                 20

<210> SEQ ID NO 122
<211> LENGTH: 22
<212> TYPE: DNA
<213> ORGANISM: Artificial Sequence
<220> FEATURE:
<223> OTHER INFORMATION: probe

<400> SEQUENCE: 122
cattggctcc ccgtgacctg ta                                              22

<210> SEQ ID NO 123
<211> LENGTH: 27
<212> TYPE: DNA
<213> ORGANISM: Artificial Sequence
<220> FEATURE:
<223> OTHER INFORMATION: forward primer

<400> SEQUENCE: 123
tgtgagtgaa atgccttcta gtagtga                                         27

<210> SEQ ID NO 124
<211> LENGTH: 23
<212> TYPE: DNA
<213> ORGANISM: Artificial Sequence
<220> FEATURE:
<223> OTHER INFORMATION: probe

<400> SEQUENCE: 124
ccgtcctcgg gagccgacta tga                                             23

<210> SEQ ID NO 125
<211> LENGTH: 27
<212> TYPE: DNA
<213> ORGANISM: Artificial Sequence
<220> FEATURE:
<223> OTHER INFORMATION: reverse primer

<400> SEQUENCE: 125
ttgtggttcg ttatcatact cttctga                                         27

<210> SEQ ID NO 126
<211> LENGTH: 21

```
<212> TYPE: DNA
<213> ORGANISM: Artificial Sequence
<220> FEATURE:
<223> OTHER INFORMATION: forward primer

<400> SEQUENCE: 126
cagcagatgt ggatcagcaa g                                              21

<210> SEQ ID NO 127
<211> LENGTH: 18
<212> TYPE: DNA
<213> ORGANISM: Artificial Sequence
<220> FEATURE:
<223> OTHER INFORMATION: reverse primer

<400> SEQUENCE: 127
gcatttgcgg tggacgat                                                  18

<210> SEQ ID NO 128
<211> LENGTH: 23
<212> TYPE: DNA
<213> ORGANISM: Artificial Sequence
<220> FEATURE:
<223> OTHER INFORMATION: probe

<400> SEQUENCE: 128
aggagtatga cgagtccggc ccc                                            23

<210> SEQ ID NO 129
<211> LENGTH: 22
<212> TYPE: DNA
<213> ORGANISM: Artificial Sequence
<220> FEATURE:
<223> OTHER INFORMATION: forward primer

<400> SEQUENCE: 129
ggctcttgtg cgtactgtcc tt                                             22

<210> SEQ ID NO 130
<211> LENGTH: 23
<212> TYPE: DNA
<213> ORGANISM: Artificial Sequence
<220> FEATURE:
<223> OTHER INFORMATION: reverse primer

<400> SEQUENCE: 130
tcagatgacg aagagcacag atg                                            23

<210> SEQ ID NO 131
<211> LENGTH: 29
<212> TYPE: DNA
<213> ORGANISM: Artificial Sequence
<220> FEATURE:
<223> OTHER INFORMATION: probe

<400> SEQUENCE: 131
aggctcagtg atgtcttccc tgtcaccag                                      29

<210> SEQ ID NO 132
<211> LENGTH: 19
<212> TYPE: DNA
<213> ORGANISM: Artificial Sequence
<220> FEATURE:
<223> OTHER INFORMATION: forward primer

<400> SEQUENCE: 132
```

```
gggtcaggtg cctcgagat                                                  19
```

<210> SEQ ID NO 133
<211> LENGTH: 21
<212> TYPE: DNA
<213> ORGANISM: Artificial Sequence
<220> FEATURE:
<223> OTHER INFORMATION: reverse primer
<400> SEQUENCE: 133

```
ctgctcactc ggctcaaact c                                               21
```

<210> SEQ ID NO 134
<211> LENGTH: 24
<212> TYPE: DNA
<213> ORGANISM: Artificial Sequence
<220> FEATURE:
<223> OTHER INFORMATION: probe
<400> SEQUENCE: 134

```
tgggcccaga gcatgttcca gatc                                            24
```

<210> SEQ ID NO 135
<211> LENGTH: 23
<212> TYPE: DNA
<213> ORGANISM: Artificial Sequence
<220> FEATURE:
<223> OTHER INFORMATION: forward primer
<400> SEQUENCE: 135

```
cgttgtcagc acttggaata caa                                             23
```

<210> SEQ ID NO 136
<211> LENGTH: 24
<212> TYPE: DNA
<213> ORGANISM: Artificial Sequence
<220> FEATURE:
<223> OTHER INFORMATION: reverse primer
<400> SEQUENCE: 136

```
gttcaacctc ttcctgtgga ctgt                                            24
```

<210> SEQ ID NO 137
<211> LENGTH: 26
<212> TYPE: DNA
<213> ORGANISM: Artificial Sequence
<220> FEATURE:
<223> OTHER INFORMATION: probe
<400> SEQUENCE: 137

```
cccaattaac atgacccggc aaccat                                          26
```

<210> SEQ ID NO 138
<211> LENGTH: 20
<212> TYPE: DNA
<213> ORGANISM: Artificial Sequence
<220> FEATURE:
<223> OTHER INFORMATION: forward primer
<400> SEQUENCE: 138

```
cctggagggt cctgtacaat                                                 20
```

<210> SEQ ID NO 139
<211> LENGTH: 19
<212> TYPE: DNA
<213> ORGANISM: Artificial Sequence

```
<220> FEATURE:
<223> OTHER INFORMATION: reverse primer

<400> SEQUENCE: 139
ctaattgggc tccatctcg                                               19

<210> SEQ ID NO 140
<211> LENGTH: 24
<212> TYPE: DNA
<213> ORGANISM: Artificial Sequence
<220> FEATURE:
<223> OTHER INFORMATION: probe

<400> SEQUENCE: 140
catcatggga ctcctgccct tacc                                         24

<210> SEQ ID NO 141
<211> LENGTH: 25
<212> TYPE: DNA
<213> ORGANISM: Artificial Sequence
<220> FEATURE:
<223> OTHER INFORMATION: forward primer

<400> SEQUENCE: 141
cagatggacc tagtacccac tgaga                                        25

<210> SEQ ID NO 142
<211> LENGTH: 22
<212> TYPE: DNA
<213> ORGANISM: Artificial Sequence
<220> FEATURE:
<223> OTHER INFORMATION: probe

<400> SEQUENCE: 142
ttccacgccg aaggacagcg at                                           22

<210> SEQ ID NO 143
<211> LENGTH: 24
<212> TYPE: DNA
<213> ORGANISM: Artificial Sequence
<220> FEATURE:
<223> OTHER INFORMATION: reverse primer

<400> SEQUENCE: 143
cctatgattt aagggcattt ttcc                                         24

<210> SEQ ID NO 144
<211> LENGTH: 20
<212> TYPE: DNA
<213> ORGANISM: Artificial Sequence
<220> FEATURE:
<223> OTHER INFORMATION: forward primer

<400> SEQUENCE: 144
atcctagccc tggtttttgg                                              20

<210> SEQ ID NO 145
<211> LENGTH: 20
<212> TYPE: DNA
<213> ORGANISM: Artificial sequence
<220> FEATURE:
<223> OTHER INFORMATION: reverse primer

<400> SEQUENCE: 145
ctgccttctc atctgcacaa                                              20
```

```
<210> SEQ ID NO 146
<211> LENGTH: 20
<212> TYPE: DNA
<213> ORGANISM: Artificial Sequence
<220> FEATURE:
<223> OTHER INFORMATION: probe

<400> SEQUENCE: 146
tttgctgtca ccagcgtcgc                                              20

<210> SEQ ID NO 147
<211> LENGTH: 20
<212> TYPE: DNA
<213> ORGANISM: Artificial Sequence
<220> FEATURE:
<223> OTHER INFORMATION: forward primer

<400> SEQUENCE: 147
ttcaggttgt tgcaggagac                                              20

<210> SEQ ID NO 148
<211> LENGTH: 20
<212> TYPE: DNA
<213> ORGANISM: Artificial Sequence
<220> FEATURE:
<223> OTHER INFORMATION: reverse primer

<400> SEQUENCE: 148
catcttcttg ggcacacaat                                              20

<210> SEQ ID NO 149
<211> LENGTH: 27
<212> TYPE: DNA
<213> ORGANISM: Artificial Sequence
<220> FEATURE:
<223> OTHER INFORMATION: probe

<400> SEQUENCE: 149
tgtctccatt attgatcggt tcatgca                                      27

<210> SEQ ID NO 150
<211> LENGTH: 21
<212> TYPE: DNA
<213> ORGANISM: Artificial Sequence
<220> FEATURE:
<223> OTHER INFORMATION: forward primer

<400> SEQUENCE: 150
gcatgttcgt ggcctctaag a                                            21

<210> SEQ ID NO 151
<211> LENGTH: 22
<212> TYPE: DNA
<213> ORGANISM: Artificial Sequence
<220> FEATURE:
<223> OTHER INFORMATION: reverse primer

<400> SEQUENCE: 151
cggtgtagat gcacagcttc tc                                           22

<210> SEQ ID NO 152
<211> LENGTH: 23
<212> TYPE: DNA
<213> ORGANISM: Artificial Sequence
<220> FEATURE:
<223> OTHER INFORMATION: probe
```

```
<400> SEQUENCE: 152
aaggagacca tccccctgac ggc                                              23

<210> SEQ ID NO 153
<211> LENGTH: 24
<212> TYPE: DNA
<213> ORGANISM: Artificial Sequence
<220> FEATURE:
<223> OTHER INFORMATION: forward primer

<400> SEQUENCE: 153
aaagaagatg atgaccgggt ttac                                             24

<210> SEQ ID NO 154
<211> LENGTH: 20
<212> TYPE: DNA
<213> ORGANISM: Artificial Sequence
<220> FEATURE:
<223> OTHER INFORMATION: reverse primer

<400> SEQUENCE: 154
gagcctctgg atggtgcaat                                                  20

<210> SEQ ID NO 155
<211> LENGTH: 24
<212> TYPE: DNA
<213> ORGANISM: Artificial Sequence
<220> FEATURE:
<223> OTHER INFORMATION: probe

<400> SEQUENCE: 155
caaactcaac gtgcaagcct cgga                                             24

<210> SEQ ID NO 156
<211> LENGTH: 22
<212> TYPE: DNA
<213> ORGANISM: Artificial Sequence
<220> FEATURE:
<223> OTHER INFORMATION: forward primer

<400> SEQUENCE: 156
atgctgtggc tccttcctaa ct                                               22

<210> SEQ ID NO 157
<211> LENGTH: 27
<212> TYPE: DNA
<213> ORGANISM: Artificial Sequence
<220> FEATURE:
<223> OTHER INFORMATION: reverse primer

<400> SEQUENCE: 157
acccaaattg tgatatacaa aaaggtt                                          27

<210> SEQ ID NO 158
<211> LENGTH: 30
<212> TYPE: DNA
<213> ORGANISM: Artificial Sequence
<220> FEATURE:
<223> OTHER INFORMATION: probe

<400> SEQUENCE: 158
taccaagcaa cctacatgtc aagaaagccc                                       30

<210> SEQ ID NO 159
```

```
<211> LENGTH: 20
<212> TYPE: DNA
<213> ORGANISM: Artificial Sequence
<220> FEATURE:
<223> OTHER INFORMATION: forward primer

<400> SEQUENCE: 159
agatgaagtg gaaggcgctt                                                    20

<210> SEQ ID NO 160
<211> LENGTH: 18
<212> TYPE: DNA
<213> ORGANISM: Artificial Sequence
<220> FEATURE:
<223> OTHER INFORMATION: probe

<400> SEQUENCE: 160
caccgcggcc atcctgca                                                      18

<210> SEQ ID NO 161
<211> LENGTH: 21
<212> TYPE: DNA
<213> ORGANISM: Artificial Sequence
<220> FEATURE:
<223> OTHER INFORMATION: reverse primer

<400> SEQUENCE: 161
tgcctctgta atcggcaact g                                                  21

<210> SEQ ID NO 162
<211> LENGTH: 18
<212> TYPE: DNA
<213> ORGANISM: Artificial Sequence
<220> FEATURE:
<223> OTHER INFORMATION: forward primer

<400> SEQUENCE: 162
tggttcccag ccctgtgt                                                      18

<210> SEQ ID NO 163
<211> LENGTH: 28
<212> TYPE: DNA
<213> ORGANISM: Artificial Sequence
<220> FEATURE:
<223> OTHER INFORMATION: probe

<400> SEQUENCE: 163
ctccaagccc agattcagat tcgagtca                                           28

<210> SEQ ID NO 164
<211> LENGTH: 19
<212> TYPE: DNA
<213> ORGANISM: Artificial Sequence
<220> FEATURE:
<223> OTHER INFORMATION: reverse primer

<400> SEQUENCE: 164
ctcctccacc ctgggttgt                                                     19

<210> SEQ ID NO 165
<211> LENGTH: 20
<212> TYPE: DNA
<213> ORGANISM: Artificial Sequence
<220> FEATURE:
<223> OTHER INFORMATION: forward primer

<400> SEQUENCE: 165
```

```
gggcgtggaa cagtttatct                                         20

<210> SEQ ID NO 166
<211> LENGTH: 19
<212> TYPE: DNA
<213> ORGANISM: Artificial Sequence
<220> FEATURE:
<223> OTHER INFORMATION: reverse primer

<400> SEQUENCE: 166
cacggtgaag gtttcgagt                                          19

<210> SEQ ID NO 167
<211> LENGTH: 24
<212> TYPE: DNA
<213> ORGANISM: Artificial Sequence
<220> FEATURE:
<223> OTHER INFORMATION: probe

<400> SEQUENCE: 167
agacatctgc cccaagaagg acgt                                    24

<210> SEQ ID NO 168
<211> LENGTH: 21
<212> TYPE: DNA
<213> ORGANISM: Artificial Sequence
<220> FEATURE:
<223> OTHER INFORMATION: forward primer

<400> SEQUENCE: 168
tgagtgtccc ccggtatctt c                                       21

<210> SEQ ID NO 169
<211> LENGTH: 21
<212> TYPE: DNA
<213> ORGANISM: Artificial Sequence
<220> FEATURE:
<223> OTHER INFORMATION: reverse primer

<400> SEQUENCE: 169
cagccgcttt cagattttca t                                       21

<210> SEQ ID NO 170
<211> LENGTH: 27
<212> TYPE: DNA
<213> ORGANISM: Artificial Sequence
<220> FEATURE:
<223> OTHER INFORMATION: probe

<400> SEQUENCE: 170
tgccaatccc gatgaaattg gaaattt                                 27

<210> SEQ ID NO 171
<211> LENGTH: 21
<212> TYPE: DNA
<213> ORGANISM: Artificial Sequence
<220> FEATURE:
<223> OTHER INFORMATION: forward primer

<400> SEQUENCE: 171
tgacaatcag cacacctgca t                                       21

<210> SEQ ID NO 172
<211> LENGTH: 23
<212> TYPE: DNA
```

```
<213> ORGANISM: Artificial Sequence
<220> FEATURE:
<223> OTHER INFORMATION: reverse primer

<400> SEQUENCE: 172
tgtgactaca gccgtgatcc tta                                     23

<210> SEQ ID NO 173
<211> LENGTH: 20
<212> TYPE: DNA
<213> ORGANISM: Artificial Sequence
<220> FEATURE:
<223> OTHER INFORMATION: probe

<400> SEQUENCE: 173
caggccctct tccgagcggt                                         20

<210> SEQ ID NO 174
<211> LENGTH: 26
<212> TYPE: DNA
<213> ORGANISM: Artificial Sequence
<220> FEATURE:
<223> OTHER INFORMATION: forward primer

<400> SEQUENCE: 174
gataaattgg tacaagggat cagctt                                  26

<210> SEQ ID NO 175
<211> LENGTH: 24
<212> TYPE: DNA
<213> ORGANISM: Artificial Sequence
<220> FEATURE:
<223> OTHER INFORMATION: reverse primer

<400> SEQUENCE: 175
gggtgccaag taactgacta ttca                                    24

<210> SEQ ID NO 176
<211> LENGTH: 26
<212> TYPE: DNA
<213> ORGANISM: Artificial Sequence
<220> FEATURE:
<223> OTHER INFORMATION: probe

<400> SEQUENCE: 176
ccagcccaca tgtcctgatc atatgc                                  26

<210> SEQ ID NO 177
<211> LENGTH: 18
<212> TYPE: DNA
<213> ORGANISM: Artificial Sequence
<220> FEATURE:
<223> OTHER INFORMATION: forward primer

<400> SEQUENCE: 177
tgcctgtggt gggaagct                                           18

<210> SEQ ID NO 178
<211> LENGTH: 19
<212> TYPE: DNA
<213> ORGANISM: Artificial Sequence
<220> FEATURE:
<223> OTHER INFORMATION: reverse primer

<400> SEQUENCE: 178
ggaaaatgcc tccggtgtt                                          19
```

```
<210> SEQ ID NO 179
<211> LENGTH: 30
<212> TYPE: DNA
<213> ORGANISM: Artificial Sequence
<220> FEATURE:
<223> OTHER INFORMATION: probe

<400> SEQUENCE: 179
tgacatagca tcatcctttg gttcccagtt                                              30

<210> SEQ ID NO 180
<211> LENGTH: 24
<212> TYPE: DNA
<213> ORGANISM: Artificial Sequence
<220> FEATURE:
<223> OTHER INFORMATION: forward primer

<400> SEQUENCE: 180
ggatatttcc gtggctctta ttca                                                    24

<210> SEQ ID NO 181
<211> LENGTH: 30
<212> TYPE: DNA
<213> ORGANISM: Artificial Sequence
<220> FEATURE:
<223> OTHER INFORMATION: probe

<400> SEQUENCE: 181
tctccatcaa atcctgtaaa ctccagagca                                              30

<210> SEQ ID NO 182
<211> LENGTH: 25
<212> TYPE: DNA
<213> ORGANISM: Artificial Sequence
<220> FEATURE:
<223> OTHER INFORMATION: reverse primer

<400> SEQUENCE: 182
cttctcatca aggcagaaaa atctt                                                   25

<210> SEQ ID NO 183
<211> LENGTH: 22
<212> TYPE: DNA
<213> ORGANISM: Artificial Sequence
<220> FEATURE:
<223> OTHER INFORMATION: forward primer

<400> SEQUENCE: 183
gacatttcca gtcctgcagt ca                                                      22

<210> SEQ ID NO 184
<211> LENGTH: 23
<212> TYPE: DNA
<213> ORGANISM: Artificial Sequence
<220> FEATURE:
<223> OTHER INFORMATION: probe

<400> SEQUENCE: 184
tgcctctctg ccccaccctt tgt                                                     23

<210> SEQ ID NO 185
<211> LENGTH: 20
<212> TYPE: DNA
<213> ORGANISM: Artificial Sequence
<220> FEATURE:
```

```
<223> OTHER INFORMATION: reverse primer

<400> SEQUENCE: 185
ctccgatcgc acacatttgt                                              20

<210> SEQ ID NO 186
<211> LENGTH: 18
<212> TYPE: DNA
<213> ORGANISM: Artificial Sequence
<220> FEATURE:
<223> OTHER INFORMATION: forward primer

<400> SEQUENCE: 186
ggcatcctgg cccaaagt                                                18

<210> SEQ ID NO 187
<211> LENGTH: 21
<212> TYPE: DNA
<213> ORGANISM: Artificial Sequence
<220> FEATURE:
<223> OTHER INFORMATION: reverse primer

<400> SEQUENCE: 187
gaccccctca gctggtagtt g                                            21

<210> SEQ ID NO 188
<211> LENGTH: 23
<212> TYPE: DNA
<213> ORGANISM: Artificial Sequence
<220> FEATURE:
<223> OTHER INFORMATION: probe

<400> SEQUENCE: 188
cccaaatcca ggcggctaga ggc                                          23

<210> SEQ ID NO 189
<211> LENGTH: 23
<212> TYPE: DNA
<213> ORGANISM: Artificial Sequence
<220> FEATURE:
<223> OTHER INFORMATION: forward primer

<400> SEQUENCE: 189
tctgcagagt tggaagcact cta                                          23

<210> SEQ ID NO 190
<211> LENGTH: 28
<212> TYPE: DNA
<213> ORGANISM: Artificial Sequence
<220> FEATURE:
<223> OTHER INFORMATION: probe

<400> SEQUENCE: 190
caggatacag ctccacagca tcgatgtc                                     28

<210> SEQ ID NO 191
<211> LENGTH: 21
<212> TYPE: DNA
<213> ORGANISM: Artificial Sequence
<220> FEATURE:
<223> OTHER INFORMATION: reverse primer

<400> SEQUENCE: 191
gccgaggctt ttctaccaga a                                            21
```

```
<210> SEQ ID NO 192
<211> LENGTH: 23
<212> TYPE: DNA
<213> ORGANISM: Artificial Sequence
<220> FEATURE:
<223> OTHER INFORMATION: forward primer

<400> SEQUENCE: 192
gggaggctta tctcactgag tga                                          23

<210> SEQ ID NO 193
<211> LENGTH: 19
<212> TYPE: DNA
<213> ORGANISM: Artificial Sequence
<220> FEATURE:
<223> OTHER INFORMATION: reverse primer

<400> SEQUENCE: 193
ccattgcagc cttcattgc                                               19

<210> SEQ ID NO 194
<211> LENGTH: 29
<212> TYPE: DNA
<213> ORGANISM: Artificial Sequence
<220> FEATURE:
<223> OTHER INFORMATION: probe

<400> SEQUENCE: 194
ttgaggccca gagcagtcta ccagattct                                    29

<210> SEQ ID NO 195
<211> LENGTH: 21
<212> TYPE: DNA
<213> ORGANISM: Artificial Sequence
<220> FEATURE:
<223> OTHER INFORMATION: forward primer

<400> SEQUENCE: 195
tgtctcactg agcgagcaga a                                            21

<210> SEQ ID NO 196
<211> LENGTH: 19
<212> TYPE: DNA
<213> ORGANISM: Artificial Sequence
<220> FEATURE:
<223> OTHER INFORMATION: reverse primer

<400> SEQUENCE: 196
accattgcag ccctgattg                                               19

<210> SEQ ID NO 197
<211> LENGTH: 24
<212> TYPE: DNA
<213> ORGANISM: Artificial Sequence
<220> FEATURE:
<223> OTHER INFORMATION: probe

<400> SEQUENCE: 197
cttgaggacg cgaacagtcc acca                                         24

<210> SEQ ID NO 198
<211> LENGTH: 22
<212> TYPE: DNA
<213> ORGANISM: Artificial Sequence
<220> FEATURE:
<223> OTHER INFORMATION: forward primer
```

```
<400> SEQUENCE: 198
cgctgacatc atgaatgttc ct                                              22

<210> SEQ ID NO 199
<211> LENGTH: 24
<212> TYPE: DNA
<213> ORGANISM: Artificial Sequence
<220> FEATURE:
<223> OTHER INFORMATION: reverse primer

<400> SEQUENCE: 199
tctctttcag caacgatgtg tctt                                            24

<210> SEQ ID NO 200
<211> LENGTH: 25
<212> TYPE: DNA
<213> ORGANISM: Artificial Sequence
<220> FEATURE:
<223> OTHER INFORMATION: probe

<400> SEQUENCE: 200
tcatatccaa actcgcctcc agccg                                           25

<210> SEQ ID NO 201
<211> LENGTH: 19
<212> TYPE: DNA
<213> ORGANISM: Artificial Sequence
<220> FEATURE:
<223> OTHER INFORMATION: forward primer

<400> SEQUENCE: 201
cacaatggcg gctctgaag                                                  19

<210> SEQ ID NO 202
<211> LENGTH: 26
<212> TYPE: DNA
<213> ORGANISM: Artificial Sequence
<220> FEATURE:
<223> OTHER INFORMATION: reverse primer

<400> SEQUENCE: 202
acacaaacac tgtctgtacc tgaaga                                          26

<210> SEQ ID NO 203
<211> LENGTH: 23
<212> TYPE: DNA
<213> ORGANISM: Artificial Sequence
<220> FEATURE:
<223> OTHER INFORMATION: probe

<400> SEQUENCE: 203
aagttacgct gcgcgacagc caa                                             23

<210> SEQ ID NO 204
<211> LENGTH: 24
<212> TYPE: DNA
<213> ORGANISM: Artificial Sequence
<220> FEATURE:
<223> OTHER INFORMATION: forward primer

<400> SEQUENCE: 204
ctctgagaca gtgcttcgat gact                                            24

<210> SEQ ID NO 205
<211> LENGTH: 19
```

```
<212> TYPE: DNA
<213> ORGANISM: Artificial Sequence
<220> FEATURE:
<223> OTHER INFORMATION: reverse primer

<400> SEQUENCE: 205
ccatgaggcc caacttcct                                              19

<210> SEQ ID NO 206
<211> LENGTH: 23
<212> TYPE: DNA
<213> ORGANISM: Artificial Sequence
<220> FEATURE:
<223> OTHER INFORMATION: probe

<400> SEQUENCE: 206
cagacttggt gccctttgac tcc                                         23

<210> SEQ ID NO 207
<211> LENGTH: 20
<212> TYPE: DNA
<213> ORGANISM: Artificial Sequence
<220> FEATURE:
<223> OTHER INFORMATION: forward primer

<400> SEQUENCE: 207
tgtcgatgga cttccagaac                                             20

<210> SEQ ID NO 208
<211> LENGTH: 18
<212> TYPE: DNA
<213> ORGANISM: Artificial Sequence
<220> FEATURE:
<223> OTHER INFORMATION: probe

<400> SEQUENCE: 208
cacctgggca gctgccaa                                               18

<210> SEQ ID NO 209
<211> LENGTH: 19
<212> TYPE: DNA
<213> ORGANISM: Artificial Sequence
<220> FEATURE:
<223> OTHER INFORMATION: reverse primer

<400> SEQUENCE: 209
attgggacag cttggatca                                              19

<210> SEQ ID NO 210
<211> LENGTH: 23
<212> TYPE: DNA
<213> ORGANISM: Artificial Sequence
<220> FEATURE:
<223> OTHER INFORMATION: forward primer

<400> SEQUENCE: 210
gatctaagat ggcgactgtc gaa                                         23

<210> SEQ ID NO 211
<211> LENGTH: 25
<212> TYPE: DNA
<213> ORGANISM: Artificial Sequence
<220> FEATURE:
<223> OTHER INFORMATION: reverse primer

<400> SEQUENCE: 211
```
ttagattccg ttttctcctc ttctg                                    25

<210> SEQ ID NO 212
<211> LENGTH: 27
<212> TYPE: DNA
<213> ORGANISM: Artificial Sequence
<220> FEATURE:
<223> OTHER INFORMATION: probe

<400> SEQUENCE: 212
accaccccta ctcctaatcc cccgact                                  27

<210> SEQ ID NO 213
<211> LENGTH: 22
<212> TYPE: DNA
<213> ORGANISM: Artificial Sequence
<220> FEATURE:
<223> OTHER INFORMATION: forward primer

<400> SEQUENCE: 213
ggcagtgtca ctgagtcctt ga                                       22

<210> SEQ ID NO 214
<211> LENGTH: 18
<212> TYPE: DNA
<213> ORGANISM: Artificial Sequence
<220> FEATURE:
<223> OTHER INFORMATION: reverse primer

<400> SEQUENCE: 214
tgcactgtgc gtcccaat                                            18

<210> SEQ ID NO 215
<211> LENGTH: 18
<212> TYPE: DNA
<213> ORGANISM: Artificial Sequence
<220> FEATURE:
<223> OTHER INFORMATION: probe

<400> SEQUENCE: 215
atcctcccct gccccgcg                                            18

<210> SEQ ID NO 216
<211> LENGTH: 20
<212> TYPE: DNA
<213> ORGANISM: Artificial Sequence
<220> FEATURE:
<223> OTHER INFORMATION: forward primer

<400> SEQUENCE: 216
gggccctcca gaacaatgat                                          20

<210> SEQ ID NO 217
<211> LENGTH: 21
<212> TYPE: DNA
<213> ORGANISM: Artificial Sequence
<220> FEATURE:
<223> OTHER INFORMATION: reverse primer

<400> SEQUENCE: 217
tgcactgctt ggccttaaag a                                        21

<210> SEQ ID NO 218
<211> LENGTH: 25
<212> TYPE: DNA
<213> ORGANISM: Artificial Sequence -continued

```
<220> FEATURE:
<223> OTHER INFORMATION: probe

<400> SEQUENCE: 218
ccgctctcat cgcagtcagg atcat                                    25

<210> SEQ ID NO 219
<211> LENGTH: 20
<212> TYPE: DNA
<213> ORGANISM: Artificial Sequence
<220> FEATURE:
<223> OTHER INFORMATION: forward primer

<400> SEQUENCE: 219
accgtaggct ctgctctgaa                                          20

<210> SEQ ID NO 220
<211> LENGTH: 20
<212> TYPE: DNA
<213> ORGANISM: Artificial Sequence
<220> FEATURE:
<223> OTHER INFORMATION: reverse primer

<400> SEQUENCE: 220
tggtccaggt ggaaaacttc                                          20

<210> SEQ ID NO 221
<211> LENGTH: 20
<212> TYPE: DNA
<213> ORGANISM: Artificial Sequence
<220> FEATURE:
<223> OTHER INFORMATION: probe

<400> SEQUENCE: 221
aggcagccag acccacagga                                          20

<210> SEQ ID NO 222
<211> LENGTH: 23
<212> TYPE: DNA
<213> ORGANISM: Artificial Sequence
<220> FEATURE:
<223> OTHER INFORMATION: forward primer

<400> SEQUENCE: 222
cggttatgtc atgccagata cac                                      23

<210> SEQ ID NO 223
<211> LENGTH: 25
<212> TYPE: DNA
<213> ORGANISM: Artificial Sequence
<220> FEATURE:
<223> OTHER INFORMATION: probe

<400> SEQUENCE: 223
cctcaaaggt actccctcct cccgg                                    25

<210> SEQ ID NO 224
<211> LENGTH: 24
<212> TYPE: DNA
<213> ORGANISM: Artificial Sequence
<220> FEATURE:
<223> OTHER INFORMATION: reverse primer

<400> SEQUENCE: 224
gaactgagac ccactgaaga aagg                                     24
```

<210> SEQ ID NO 225
<211> LENGTH: 19
<212> TYPE: DNA
<213> ORGANISM: Artificial Sequence
<220> FEATURE:
<223> OTHER INFORMATION: forward primer

<400> SEQUENCE: 225
cgtggtgccc ctctatgac                                          19

<210> SEQ ID NO 226
<211> LENGTH: 19
<212> TYPE: DNA
<213> ORGANISM: Artificial Sequence
<220> FEATURE:
<223> OTHER INFORMATION: probe

<400> SEQUENCE: 226
ctggagatgc tggacgccc                                          19

<210> SEQ ID NO 227
<211> LENGTH: 19
<212> TYPE: DNA
<213> ORGANISM: Artificial Sequence
<220> FEATURE:
<223> OTHER INFORMATION: reverse primer

<400> SEQUENCE: 227
ggctagtggg cgcatgtag                                          19

<210> SEQ ID NO 228
<211> LENGTH: 25
<212> TYPE: DNA
<213> ORGANISM: Artificial Sequence
<220> FEATURE:
<223> OTHER INFORMATION: reverse primer

<400> SEQUENCE: 228
ggattgtaga ctgtcaccga aattc                                   25

<210> SEQ ID NO 229
<211> LENGTH: 28
<212> TYPE: DNA
<213> ORGANISM: Artificial Sequence
<220> FEATURE:
<223> OTHER INFORMATION: forward primer

<400> SEQUENCE: 229
ggctattcct cattttctct acaaagtg                                28

<210> SEQ ID NO 230
<211> LENGTH: 30
<212> TYPE: DNA
<213> ORGANISM: Artificial Sequence
<220> FEATURE:
<223> OTHER INFORMATION: probe

<400> SEQUENCE: 230
cctccaggag gctaccttct tcatgttcac                              30

<210> SEQ ID NO 231
<211> LENGTH: 21
<212> TYPE: DNA
<213> ORGANISM: Artificial Sequence
<220> FEATURE:
<223> OTHER INFORMATION: forward primer

```
<400> SEQUENCE: 231
cggtagtcaa gtccggatca a                                          21

<210> SEQ ID NO 232
<211> LENGTH: 18
<212> TYPE: DNA
<213> ORGANISM: Artificial Sequence
<220> FEATURE:
<223> OTHER INFORMATION: reverse primer

<400> SEQUENCE: 232
gcttgccttt gcggttca                                              18

<210> SEQ ID NO 233
<211> LENGTH: 25
<212> TYPE: DNA
<213> ORGANISM: Artificial Sequence
<220> FEATURE:
<223> OTHER INFORMATION: probe

<400> SEQUENCE: 233
caaggagacg gaattctacc tgtgc                                      25

<210> SEQ ID NO 234
<211> LENGTH: 20
<212> TYPE: DNA
<213> ORGANISM: Artificial Sequence
<220> FEATURE:
<223> OTHER INFORMATION: forward primer

<400> SEQUENCE: 234
cacgggacat tcaccacatc                                            20

<210> SEQ ID NO 235
<211> LENGTH: 19
<212> TYPE: DNA
<213> ORGANISM: Artificial Sequence
<220> FEATURE:
<223> OTHER INFORMATION: reverse primer

<400> SEQUENCE: 235
gggtgccatc cacttcaca                                             19

<210> SEQ ID NO 236
<211> LENGTH: 27
<212> TYPE: DNA
<213> ORGANISM: Artificial Sequence
<220> FEATURE:
<223> OTHER INFORMATION: probe

<400> SEQUENCE: 236
ataaaaagac aaccaacggc cgactgc                                    27

<210> SEQ ID NO 237
<211> LENGTH: 18
<212> TYPE: DNA
<213> ORGANISM: Artificial Sequence
<220> FEATURE:
<223> OTHER INFORMATION: forward primer

<400> SEQUENCE: 237
ccagtggagc gcttccat                                              18

<210> SEQ ID NO 238
```

```
<211> LENGTH: 22
<212> TYPE: DNA
<213> ORGANISM: Artificial Sequence
<220> FEATURE:
<223> OTHER INFORMATION: reverse primer

<400> SEQUENCE: 238
ctctctgggt cgtctgaaac aa                                           22

<210> SEQ ID NO 239
<211> LENGTH: 23
<212> TYPE: DNA
<213> ORGANISM: Artificial Sequence
<220> FEATURE:
<223> OTHER INFORMATION: probe

<400> SEQUENCE: 239
tcggccactt catcaggacg cag                                          23

<210> SEQ ID NO 240
<211> LENGTH: 20
<212> TYPE: DNA
<213> ORGANISM: Artificial Sequence
<220> FEATURE:
<223> OTHER INFORMATION: forward primer

<400> SEQUENCE: 240
ttggtacctg tgggttagca                                              20

<210> SEQ ID NO 241
<211> LENGTH: 20
<212> TYPE: DNA
<213> ORGANISM: Artificial Sequence
<220> FEATURE:
<223> OTHER INFORMATION: reverse primer

<400> SEQUENCE: 241
cacatccaaa tgcaaactgg                                              20

<210> SEQ ID NO 242
<211> LENGTH: 26
<212> TYPE: DNA
<213> ORGANISM: Artificial Sequence
<220> FEATURE:
<223> OTHER INFORMATION: probe

<400> SEQUENCE: 242
tccccagggt agaattcaat cagagc                                       26

<210> SEQ ID NO 243
<211> LENGTH: 19
<212> TYPE: DNA
<213> ORGANISM: Artificial Sequence
<220> FEATURE:
<223> OTHER INFORMATION: forward primer

<400> SEQUENCE: 243
tcagcagcaa gggcatcat                                               19

<210> SEQ ID NO 244
<211> LENGTH: 23
<212> TYPE: DNA
<213> ORGANISM: Artificial Sequence
<220> FEATURE:
<223> OTHER INFORMATION: reverse primer

<400> SEQUENCE: 244
```

```
ggtggttttc ttgagcgtgt act                                          23

<210> SEQ ID NO 245
<211> LENGTH: 19
<212> TYPE: DNA
<213> ORGANISM: Artificial Sequence
<220> FEATURE:
<223> OTHER INFORMATION: probe

<400> SEQUENCE: 245
cgcccgcagg cctcatcct                                               19

<210> SEQ ID NO 246
<211> LENGTH: 20
<212> TYPE: DNA
<213> ORGANISM: Artificial Sequence
<220> FEATURE:
<223> OTHER INFORMATION: forward primer

<400> SEQUENCE: 246
attccaccca tggcaaattc                                              20

<210> SEQ ID NO 247
<211> LENGTH: 22
<212> TYPE: DNA
<213> ORGANISM: Artificial Sequence
<220> FEATURE:
<223> OTHER INFORMATION: reverse primer

<400> SEQUENCE: 247
gatgggattt ccattgatga ca                                           22

<210> SEQ ID NO 248
<211> LENGTH: 22
<212> TYPE: DNA
<213> ORGANISM: Artificial Sequence
<220> FEATURE:
<223> OTHER INFORMATION: probe

<400> SEQUENCE: 248
ccgttctcag ccttgacggt gc                                           22

<210> SEQ ID NO 249
<211> LENGTH: 23
<212> TYPE: DNA
<213> ORGANISM: Artificial Sequence
<220> FEATURE:
<223> OTHER INFORMATION: forward primer

<400> SEQUENCE: 249
caaaggagct cactgtggtg tct                                          23

<210> SEQ ID NO 250
<211> LENGTH: 24
<212> TYPE: DNA
<213> ORGANISM: Artificial Sequence
<220> FEATURE:
<223> OTHER INFORMATION: probe

<400> SEQUENCE: 250
tgttccaacc actgaatctg gacc                                         24

<210> SEQ ID NO 251
<211> LENGTH: 26
<212> TYPE: DNA
```

```
<213> ORGANISM: Artificial Sequence
<220> FEATURE:
<223> OTHER INFORMATION: reverse primer

<400> SEQUENCE: 251
gagtcagaat ggcttattca cagatg                                          26

<210> SEQ ID NO 252
<211> LENGTH: 20
<212> TYPE: DNA
<213> ORGANISM: Artificial Sequence
<220> FEATURE:
<223> OTHER INFORMATION: forward primer

<400> SEQUENCE: 252
ccatctgcat ccatcttgtt                                                 20

<210> SEQ ID NO 253
<211> LENGTH: 23
<212> TYPE: DNA
<213> ORGANISM: Artificial Sequence
<220> FEATURE:
<223> OTHER INFORMATION: probe

<400> SEQUENCE: 253
ctccccaccc ttgagaagtg cct                                             23

<210> SEQ ID NO 254
<211> LENGTH: 20
<212> TYPE: DNA
<213> ORGANISM: Artificial Sequence
<220> FEATURE:
<223> OTHER INFORMATION: reverse primer

<400> SEQUENCE: 254
ggccaccagg gtattatctg                                                 20

<210> SEQ ID NO 255
<211> LENGTH: 23
<212> TYPE: DNA
<213> ORGANISM: Artificial Sequence
<220> FEATURE:
<223> OTHER INFORMATION: forward primer

<400> SEQUENCE: 255
cgaaaagatg ctgaacagtg aca                                             23

<210> SEQ ID NO 256
<211> LENGTH: 20
<212> TYPE: DNA
<213> ORGANISM: Artificial Sequence
<220> FEATURE:
<223> OTHER INFORMATION: reverse primer

<400> SEQUENCE: 256
tcaggaacag ccaccagtga                                                 20

<210> SEQ ID NO 257
<211> LENGTH: 28
<212> TYPE: DNA
<213> ORGANISM: Artificial Sequence
<220> FEATURE:
<223> OTHER INFORMATION: probe

<400> SEQUENCE: 257
cttcctcctc ccttctggtc agttggat                                        28
```

```
<210> SEQ ID NO 258
<211> LENGTH: 20
<212> TYPE: DNA
<213> ORGANISM: Artificial Sequence
<220> FEATURE:
<223> OTHER INFORMATION: reverse primer

<400> SEQUENCE: 258
ggcccagctt gaatttttca                                              20

<210> SEQ ID NO 259
<211> LENGTH: 27
<212> TYPE: DNA
<213> ORGANISM: Artificial Sequence
<220> FEATURE:
<223> OTHER INFORMATION: forward primer

<400> SEQUENCE: 259
aagctatgag gaaagaagt acacgat                                       27

<210> SEQ ID NO 260
<211> LENGTH: 30
<212> TYPE: DNA
<213> ORGANISM: Artificial Sequence
<220> FEATURE:
<223> OTHER INFORMATION: probe

<400> SEQUENCE: 260
tcagccactg gcttctgtca taatcaggag                                   30

<210> SEQ ID NO 261
<211> LENGTH: 20
<212> TYPE: DNA
<213> ORGANISM: Artificial Sequence
<220> FEATURE:
<223> OTHER INFORMATION: forward primer

<400> SEQUENCE: 261
cccactcagt agccaagtca                                              20

<210> SEQ ID NO 262
<211> LENGTH: 27
<212> TYPE: DNA
<213> ORGANISM: Artificial Sequence
<220> FEATURE:
<223> OTHER INFORMATION: probe

<400> SEQUENCE: 262
tcaagtaaac gggctgtttt ccaaaca                                      27

<210> SEQ ID NO 263
<211> LENGTH: 20
<212> TYPE: DNA
<213> ORGANISM: Artificial Sequence
<220> FEATURE:
<223> OTHER INFORMATION: reverse primer

<400> SEQUENCE: 263
cacgcaggtg gtatcagtct                                              20

<210> SEQ ID NO 264
<211> LENGTH: 20
<212> TYPE: DNA
<213> ORGANISM: Artificial Sequence
<220> FEATURE:
```

```
<223> OTHER INFORMATION: forward primer

<400> SEQUENCE: 264
cggtgtgaga agtgcagcaa                                              20

<210> SEQ ID NO 265
<211> LENGTH: 24
<212> TYPE: DNA
<213> ORGANISM: Artificial Sequence
<220> FEATURE:
<223> OTHER INFORMATION: probe

<400> SEQUENCE: 265
ccagaccata gcacactcgg gcac                                         24

<210> SEQ ID NO 266
<211> LENGTH: 19
<212> TYPE: DNA
<213> ORGANISM: Artificial Sequence
<220> FEATURE:
<223> OTHER INFORMATION: reverse primer

<400> SEQUENCE: 266
cctctcgcaa gtgctccat                                               19

<210> SEQ ID NO 267
<211> LENGTH: 24
<212> TYPE: DNA
<213> ORGANISM: Artificial Sequence
<220> FEATURE:
<223> OTHER INFORMATION: forward primer

<400> SEQUENCE: 267
tgaacataaa gtctgcaaca tgga                                         24

<210> SEQ ID NO 268
<211> LENGTH: 28
<212> TYPE: DNA
<213> ORGANISM: Artificial Sequence
<220> FEATURE:
<223> OTHER INFORMATION: reverse primer

<400> SEQUENCE: 268
tgaggttggt tactgttggt atcatata                                     28

<210> SEQ ID NO 269
<211> LENGTH: 24
<212> TYPE: DNA
<213> ORGANISM: Artificial Sequence
<220> FEATURE:
<223> OTHER INFORMATION: probe

<400> SEQUENCE: 269
ttgcactgca caggccacat tcac                                         24

<210> SEQ ID NO 270
<211> LENGTH: 24
<212> TYPE: DNA
<213> ORGANISM: Artificial Sequence
<220> FEATURE:
<223> OTHER INFORMATION: forward primer

<400> SEQUENCE: 270
tccaggatgt taggaactgt gaag                                         24
```

```
<210> SEQ ID NO 271
<211> LENGTH: 22
<212> TYPE: DNA
<213> ORGANISM: Artificial Sequence
<220> FEATURE:
<223> OTHER INFORMATION: reverse primer

<400> SEQUENCE: 271
gcgtgtctgc gtagtagctg tt                                          22

<210> SEQ ID NO 272
<211> LENGTH: 24
<212> TYPE: DNA
<213> ORGANISM: Artificial Sequence
<220> FEATURE:
<223> OTHER INFORMATION: probe

<400> SEQUENCE: 272
agtcgctggt ttcatgccct tcca                                        24

<210> SEQ ID NO 273
<211> LENGTH: 19
<212> TYPE: DNA
<213> ORGANISM: Artificial Sequence
<220> FEATURE:
<223> OTHER INFORMATION: forward primer

<400> SEQUENCE: 273
agaaccgcaa ggtgagcaa                                              19

<210> SEQ ID NO 274
<211> LENGTH: 21
<212> TYPE: DNA
<213> ORGANISM: Artificial Sequence
<220> FEATURE:
<223> OTHER INFORMATION: reverse primer

<400> SEQUENCE: 274
tccaactgaa ggtccctgat g                                           21

<210> SEQ ID NO 275
<211> LENGTH: 26
<212> TYPE: DNA
<213> ORGANISM: Artificial Sequence
<220> FEATURE:
<223> OTHER INFORMATION: probe

<400> SEQUENCE: 275
tggagattct ccagcacgtc atcgac                                      26

<210> SEQ ID NO 276
<211> LENGTH: 21
<212> TYPE: DNA
<213> ORGANISM: Artificial Sequence
<220> FEATURE:
<223> OTHER INFORMATION: forward primer

<400> SEQUENCE: 276
tccggagctg tgatctaagg a                                           21

<210> SEQ ID NO 277
<211> LENGTH: 24
<212> TYPE: DNA
<213> ORGANISM: Artificial Sequence
<220> FEATURE:
<223> OTHER INFORMATION: probe
```

<400> SEQUENCE: 277
tgtattgcgc acccctcaag cctg                                        24

<210> SEQ ID NO 278
<211> LENGTH: 20
<212> TYPE: DNA
<213> ORGANISM: Artificial Sequence
<220> FEATURE:
<223> OTHER INFORMATION: reverse primer

<400> SEQUENCE: 278
cggacagagc gagctgactt                                             20

<210> SEQ ID NO 279
<211> LENGTH: 21
<212> TYPE: DNA
<213> ORGANISM: Artificial Sequence
<220> FEATURE:
<223> OTHER INFORMATION: forward primer

<400> SEQUENCE: 279
gcatggtagc cgaagatttc a                                           21

<210> SEQ ID NO 280
<211> LENGTH: 30
<212> TYPE: DNA
<213> ORGANISM: Artificial Sequence
<220> FEATURE:
<223> OTHER INFORMATION: reverse primer

<400> SEQUENCE: 280
tttccggtaa tagtctgtct catagatatc                                  30

<210> SEQ ID NO 281
<211> LENGTH: 28
<212> TYPE: DNA
<213> ORGANISM: Artificial Sequence
<220> FEATURE:
<223> OTHER INFORMATION: probe

<400> SEQUENCE: 281
cgcgtcatac caaaatctcc gattttga                                    28

<210> SEQ ID NO 282
<211> LENGTH: 19
<212> TYPE: DNA
<213> ORGANISM: Artificial Sequence
<220> FEATURE:
<223> OTHER INFORMATION: forward primer

<400> SEQUENCE: 282
gtggacagca ccatgaaca                                              19

<210> SEQ ID NO 283
<211> LENGTH: 20
<212> TYPE: DNA
<213> ORGANISM: Artificial Sequence
<220> FEATURE:
<223> OTHER INFORMATION: reverse primer

<400> SEQUENCE: 283
ccttcatacc cgacttgagg                                             20

<210> SEQ ID NO 284
<211> LENGTH: 20

```
<212> TYPE: DNA
<213> ORGANISM: Artificial Sequence
<220> FEATURE:
<223> OTHER INFORMATION: probe

<400> SEQUENCE: 284
cttccggcca gcactgcctc                                               20

<210> SEQ ID NO 285
<211> LENGTH: 20
<212> TYPE: DNA
<213> ORGANISM: Artificial Sequence
<220> FEATURE:
<223> OTHER INFORMATION: forward primer

<400> SEQUENCE: 285
cctgaacctt ccaaagatgg                                               20

<210> SEQ ID NO 286
<211> LENGTH: 20
<212> TYPE: DNA
<213> ORGANISM: Artificial Sequence
<220> FEATURE:
<223> OTHER INFORMATION: reverse primer

<400> SEQUENCE: 286
accaggcaag tctcctcatt                                               20

<210> SEQ ID NO 287
<211> LENGTH: 27
<212> TYPE: DNA
<213> ORGANISM: Artificial Sequence
<220> FEATURE:
<223> OTHER INFORMATION: probe

<400> SEQUENCE: 287
ccagattgga agcatccatc tttttca                                       27

<210> SEQ ID NO 288
<211> LENGTH: 20
<212> TYPE: DNA
<213> ORGANISM: Artificial Sequence
<220> FEATURE:
<223> OTHER INFORMATION: forward primer

<400> SEQUENCE: 288
ccacagctca ccttctgtca                                               20

<210> SEQ ID NO 289
<211> LENGTH: 20
<212> TYPE: DNA
<213> ORGANISM: Artificial Sequence
<220> FEATURE:
<223> OTHER INFORMATION: reverse primer

<400> SEQUENCE: 289
cctcagtgcc agtctcttcc                                               20

<210> SEQ ID NO 290
<211> LENGTH: 20
<212> TYPE: DNA
<213> ORGANISM: Artificial Sequence
<220> FEATURE:
<223> OTHER INFORMATION: probe

<400> SEQUENCE: 290
```

```
tccatcccag ctccagccag                                                        20
```

<210> SEQ ID NO 291
<211> LENGTH: 23
<212> TYPE: DNA
<213> ORGANISM: Artificial Sequence
<220> FEATURE:
<223> OTHER INFORMATION: probe

<400> SEQUENCE: 291

```
ccacttgtcg aaccaccgct cgt                                                    23
```

<210> SEQ ID NO 292
<211> LENGTH: 19
<212> TYPE: DNA
<213> ORGANISM: Artificial Sequence
<220> FEATURE:
<223> OTHER INFORMATION: forward primer

<400> SEQUENCE: 292

```
cggactttgg gtgcgactt                                                         19
```

<210> SEQ ID NO 293
<211> LENGTH: 24
<212> TYPE: DNA
<213> ORGANISM: Artificial Sequence
<220> FEATURE:
<223> OTHER INFORMATION: reverse primer

<400> SEQUENCE: 293

```
ttacaactct tccactggga cgat                                                   24
```

<210> SEQ ID NO 294
<211> LENGTH: 18
<212> TYPE: DNA
<213> ORGANISM: Artificial Sequence
<220> FEATURE:
<223> OTHER INFORMATION: forward primer

<400> SEQUENCE: 294

```
gcccagaggc tccatcgt                                                          18
```

<210> SEQ ID NO 295
<211> LENGTH: 23
<212> TYPE: DNA
<213> ORGANISM: Artificial Sequence
<220> FEATURE:
<223> OTHER INFORMATION: reverse primer

<400> SEQUENCE: 295

```
cagaggtttg aacagtgcag aca                                                    23
```

<210> SEQ ID NO 296
<211> LENGTH: 23
<212> TYPE: DNA
<213> ORGANISM: Artificial Sequence
<220> FEATURE:
<223> OTHER INFORMATION: probe

<400> SEQUENCE: 296

```
cctcttcctc cccagtcggc tga                                                    23
```

<210> SEQ ID NO 297
<211> LENGTH: 20
<212> TYPE: DNA
<213> ORGANISM: Artificial Sequence

```
<220> FEATURE:
<223> OTHER INFORMATION: forward primer

<400> SEQUENCE: 297
ggcctgctga gatcaaagac                                               20

<210> SEQ ID NO 298
<211> LENGTH: 20
<212> TYPE: DNA
<213> ORGANISM: Artificial Sequence
<220> FEATURE:
<223> OTHER INFORMATION: reverse primer

<400> SEQUENCE: 298
gtccactgtg gctgtgagaa                                               20

<210> SEQ ID NO 299
<211> LENGTH: 26
<212> TYPE: DNA
<213> ORGANISM: Artificial Sequence
<220> FEATURE:
<223> OTHER INFORMATION: probe

<400> SEQUENCE: 299
tgttcctcag gtcctcaatg gtcttg                                        26

<210> SEQ ID NO 300
<211> LENGTH: 21
<212> TYPE: DNA
<213> ORGANISM: Artificial Sequence
<220> FEATURE:
<223> OTHER INFORMATION: forward primer

<400> SEQUENCE: 300
cgaggattgg ttcttcagca a                                             21

<210> SEQ ID NO 301
<211> LENGTH: 22
<212> TYPE: DNA
<213> ORGANISM: Artificial Sequence
<220> FEATURE:
<223> OTHER INFORMATION: reverse primer

<400> SEQUENCE: 301
actctgcacc agctcactgt tg                                            22

<210> SEQ ID NO 302
<211> LENGTH: 24
<212> TYPE: DNA
<213> ORGANISM: Artificial Sequence
<220> FEATURE:
<223> OTHER INFORMATION: probe

<400> SEQUENCE: 302
cacctcgcgg ttcagttcct ctgt                                          24

<210> SEQ ID NO 303
<211> LENGTH: 20
<212> TYPE: DNA
<213> ORGANISM: Artificial Sequence
<220> FEATURE:
<223> OTHER INFORMATION: forward primer

<400> SEQUENCE: 303
agagatcgag gctctcaagg                                               20
```

<210> SEQ ID NO 304
<211> LENGTH: 20
<212> TYPE: DNA
<213> ORGANISM: Artificial Sequence
<220> FEATURE:
<223> OTHER INFORMATION: reverse primer

<400> SEQUENCE: 304
ggccttttac ttcctcttcg                                               20

<210> SEQ ID NO 305
<211> LENGTH: 27
<212> TYPE: DNA
<213> ORGANISM: Artificial Sequence
<220> FEATURE:
<223> OTHER INFORMATION: probe

<400> SEQUENCE: 305
tggttcttct tcatgaagag cagctcc                                       27

<210> SEQ ID NO 306
<211> LENGTH: 21
<212> TYPE: DNA
<213> ORGANISM: Artificial Sequence
<220> FEATURE:
<223> OTHER INFORMATION: forward primer

<400> SEQUENCE: 306
tgagcggcag aatcaggagt a                                             21

<210> SEQ ID NO 307
<211> LENGTH: 19
<212> TYPE: DNA
<213> ORGANISM: Artificial Sequence
<220> FEATURE:
<223> OTHER INFORMATION: reverse primer

<400> SEQUENCE: 307
tgcggtaggt ggcaatctc                                                19

<210> SEQ ID NO 308
<211> LENGTH: 24
<212> TYPE: DNA
<213> ORGANISM: Artificial Sequence
<220> FEATURE:
<223> OTHER INFORMATION: probe

<400> SEQUENCE: 308
ctcatggaca tcaagtcgcg gctg                                          24

<210> SEQ ID NO 309
<211> LENGTH: 20
<212> TYPE: DNA
<213> ORGANISM: Artificial Sequence
<220> FEATURE:
<223> OTHER INFORMATION: forward primer

<400> SEQUENCE: 309
tcagtggaga aggagttgga                                               20

<210> SEQ ID NO 310
<211> LENGTH: 28
<212> TYPE: DNA
<213> ORGANISM: Artificial Sequence
<220> FEATURE:
<223> OTHER INFORMATION: probe

<400> SEQUENCE: 310
ccagtcaaca tctctgttgt cacaagca              28

<210> SEQ ID NO 311
<211> LENGTH: 20
<212> TYPE: DNA
<213> ORGANISM: Artificial Sequence
<220> FEATURE:
<223> OTHER INFORMATION: reverse primer

<400> SEQUENCE: 311
tgccatatcc agaggaaaca              20

<210> SEQ ID NO 312
<211> LENGTH: 27
<212> TYPE: DNA
<213> ORGANISM: Artificial Sequence
<220> FEATURE:
<223> OTHER INFORMATION: forward primer

<400> SEQUENCE: 312
ggatgaagct tacatgaaca aggtaga              27

<210> SEQ ID NO 313
<211> LENGTH: 25
<212> TYPE: DNA
<213> ORGANISM: Artificial Sequence
<220> FEATURE:
<223> OTHER INFORMATION: reverse primer

<400> SEQUENCE: 313
catatagctg cctgaggaag ttgat              25

<210> SEQ ID NO 314
<211> LENGTH: 21
<212> TYPE: DNA
<213> ORGANISM: Artificial Sequence
<220> FEATURE:
<223> OTHER INFORMATION: probe

<400> SEQUENCE: 314
cgtcggtcag cccttccagg c              21

<210> SEQ ID NO 315
<211> LENGTH: 22
<212> TYPE: DNA
<213> ORGANISM: Artificial Sequence
<220> FEATURE:
<223> OTHER INFORMATION: forward primer

<400> SEQUENCE: 315
ggaaagacca cctgaaaaac ca              22

<210> SEQ ID NO 316
<211> LENGTH: 24
<212> TYPE: DNA
<213> ORGANISM: Artificial Sequence
<220> FEATURE:
<223> OTHER INFORMATION: reverse primer

<400> SEQUENCE: 316
gtacttcttc ccacactcct caca              24

<210> SEQ ID NO 317

-continued

```
<211> LENGTH: 23
<212> TYPE: DNA
<213> ORGANISM: Artificial Sequence
<220> FEATURE:
<223> OTHER INFORMATION: probe

<400> SEQUENCE: 317
acccacgacc ccaacaaaat ggc                                              23

<210> SEQ ID NO 318
<211> LENGTH: 23
<212> TYPE: DNA
<213> ORGANISM: Artificial Sequence
<220> FEATURE:
<223> OTHER INFORMATION: forward primer

<400> SEQUENCE: 318
cagatggcca ctttgagaac att                                              23

<210> SEQ ID NO 319
<211> LENGTH: 22
<212> TYPE: DNA
<213> ORGANISM: Artificial Sequence
<220> FEATURE:
<223> OTHER INFORMATION: reverse primer

<400> SEQUENCE: 319
ggcagcatta accacaagga tt                                               22

<210> SEQ ID NO 320
<211> LENGTH: 28
<212> TYPE: DNA
<213> ORGANISM: Artificial Sequence
<220> FEATURE:
<223> OTHER INFORMATION: probe

<400> SEQUENCE: 320
agctgacaac agtgtgaacg accagacc                                         28

<210> SEQ ID NO 321
<211> LENGTH: 21
<212> TYPE: DNA
<213> ORGANISM: Artificial Sequence
<220> FEATURE:
<223> OTHER INFORMATION: forward primer

<400> SEQUENCE: 321
gacttttgcc cgctaccttt c                                                21

<210> SEQ ID NO 322
<211> LENGTH: 26
<212> TYPE: DNA
<213> ORGANISM: Artificial Sequence
<220> FEATURE:
<223> OTHER INFORMATION: reverse primer

<400> SEQUENCE: 322
gccactaact gcttcagtat gaagag                                           26

<210> SEQ ID NO 323
<211> LENGTH: 24
<212> TYPE: DNA
<213> ORGANISM: Artificial Sequence
<220> FEATURE:
<223> OTHER INFORMATION: probe

<400> SEQUENCE: 323
```

```
acagctcatt gttgtcacgc cgga                                           24

<210> SEQ ID NO 324
<211> LENGTH: 20
<212> TYPE: DNA
<213> ORGANISM: Artificial Sequence
<220> FEATURE:
<223> OTHER INFORMATION: forward primer

<400> SEQUENCE: 324
ggagaacaat ccccttgaga                                                20

<210> SEQ ID NO 325
<211> LENGTH: 20
<212> TYPE: DNA
<213> ORGANISM: Artificial Sequence
<220> FEATURE:
<223> OTHER INFORMATION: reverse primer

<400> SEQUENCE: 325
atctcctgga tggtgatggt                                                20

<210> SEQ ID NO 326
<211> LENGTH: 27
<212> TYPE: DNA
<213> ORGANISM: Artificial Sequence
<220> FEATURE:
<223> OTHER INFORMATION: probe

<400> SEQUENCE: 326
tggcctttct gtctacaagg atcacca                                        27

<210> SEQ ID NO 327
<211> LENGTH: 24
<212> TYPE: DNA
<213> ORGANISM: Artificial Sequence
<220> FEATURE:
<223> OTHER INFORMATION: forward primer

<400> SEQUENCE: 327
tgatggtcct atgtgtcaca ttca                                           24

<210> SEQ ID NO 328
<211> LENGTH: 20
<212> TYPE: DNA
<213> ORGANISM: Artificial Sequence
<220> FEATURE:
<223> OTHER INFORMATION: reverse primer

<400> SEQUENCE: 328
tgggacagga aacacaccaa                                                20

<210> SEQ ID NO 329
<211> LENGTH: 30
<212> TYPE: DNA
<213> ORGANISM: Artificial Sequence
<220> FEATURE:
<223> OTHER INFORMATION: probe

<400> SEQUENCE: 329
caggtttcat accaacacag gcttcagcac                                     30

<210> SEQ ID NO 330
<211> LENGTH: 19
<212> TYPE: DNA
```

```
<213> ORGANISM: Artificial Sequence
<220> FEATURE:
<223> OTHER INFORMATION: forward primer

<400> SEQUENCE: 330
ctacagggac gccatcgaa                                                  19

<210> SEQ ID NO 331
<211> LENGTH: 23
<212> TYPE: DNA
<213> ORGANISM: Artificial Sequence
<220> FEATURE:
<223> OTHER INFORMATION: reverse primer

<400> SEQUENCE: 331
atccaaccaa tcacctgaat gtt                                             23

<210> SEQ ID NO 332
<211> LENGTH: 23
<212> TYPE: DNA
<213> ORGANISM: Artificial Sequence
<220> FEATURE:
<223> OTHER INFORMATION: probe

<400> SEQUENCE: 332
cttacaccag catcaagatc cgg                                             23

<210> SEQ ID NO 333
<211> LENGTH: 20
<212> TYPE: DNA
<213> ORGANISM: Artificial Sequence
<220> FEATURE:
<223> OTHER INFORMATION: forward primer

<400> SEQUENCE: 333
gagaaccaat ctcaccgaca                                                 20

<210> SEQ ID NO 334
<211> LENGTH: 20
<212> TYPE: DNA
<213> ORGANISM: Artificial Sequence
<220> FEATURE:
<223> OTHER INFORMATION: reverse primer

<400> SEQUENCE: 334
cacccgagtg taaccatagc                                                 20

<210> SEQ ID NO 335
<211> LENGTH: 24
<212> TYPE: DNA
<213> ORGANISM: Artificial Sequence
<220> FEATURE:
<223> OTHER INFORMATION: probe

<400> SEQUENCE: 335
acaggtattc ctctgccagc tgcc                                            24

<210> SEQ ID NO 336
<211> LENGTH: 19
<212> TYPE: DNA
<213> ORGANISM: Artificial Sequence
<220> FEATURE:
<223> OTHER INFORMATION: forward primer

<400> SEQUENCE: 336
ccgccctcac ctgaagaga                                                  19
```

```
<210> SEQ ID NO 337
<211> LENGTH: 22
<212> TYPE: DNA
<213> ORGANISM: Artificial Sequence
<220> FEATURE:
<223> OTHER INFORMATION: reverse primer

<400> SEQUENCE: 337
ggaataagtt agccgcgctt ct                                              22

<210> SEQ ID NO 338
<211> LENGTH: 21
<212> TYPE: DNA
<213> ORGANISM: Artificial Sequence
<220> FEATURE:
<223> OTHER INFORMATION: probe

<400> SEQUENCE: 338
cccagtgtcc gccaaggagc g                                               21

<210> SEQ ID NO 339
<211> LENGTH: 18
<212> TYPE: DNA
<213> ORGANISM: Artificial Sequence
<220> FEATURE:
<223> OTHER INFORMATION: forward primer

<400> SEQUENCE: 339
gccgagatcg ccaagatg                                                   18

<210> SEQ ID NO 340
<211> LENGTH: 27
<212> TYPE: DNA
<213> ORGANISM: Artificial Sequence
<220> FEATURE:
<223> OTHER INFORMATION: reverse primer

<400> SEQUENCE: 340
cttttgatgg tagagttcca gtgattc                                         27

<210> SEQ ID NO 341
<211> LENGTH: 24
<212> TYPE: DNA
<213> ORGANISM: Artificial Sequence
<220> FEATURE:
<223> OTHER INFORMATION: probe

<400> SEQUENCE: 341
cagcattgtc tgtcctccct ggca                                            24

<210> SEQ ID NO 342
<211> LENGTH: 19
<212> TYPE: DNA
<213> ORGANISM: Artificial Sequence
<220> FEATURE:
<223> OTHER INFORMATION: forward primer

<400> SEQUENCE: 342
ccctcgtgct gatgctact                                                  19

<210> SEQ ID NO 343
<211> LENGTH: 22
<212> TYPE: DNA
<213> ORGANISM: Artificial Sequence
<220> FEATURE:
```

```
<223> OTHER INFORMATION: reverse primer

<400> SEQUENCE: 343
catcatgacc tggtcttcta gg                                        22

<210> SEQ ID NO 344
<211> LENGTH: 22
<212> TYPE: DNA
<213> ORGANISM: Artificial Sequence
<220> FEATURE:
<223> OTHER INFORMATION: probe

<400> SEQUENCE: 344
ctgccctaga cgctggctcc tc                                        22

<210> SEQ ID NO 345
<211> LENGTH: 21
<212> TYPE: DNA
<213> ORGANISM: Artificial Sequence
<220> FEATURE:
<223> OTHER INFORMATION: forward primer

<400> SEQUENCE: 345
cggtggacca cgaagagtta a                                         21

<210> SEQ ID NO 346
<211> LENGTH: 23
<212> TYPE: DNA
<213> ORGANISM: Artificial Sequence
<220> FEATURE:
<223> OTHER INFORMATION: probe

<400> SEQUENCE: 346
ccgggacttg gagaagcact gca                                       23

<210> SEQ ID NO 347
<211> LENGTH: 19
<212> TYPE: DNA
<213> ORGANISM: Artificial Sequence
<220> FEATURE:
<223> OTHER INFORMATION: reverse primer

<400> SEQUENCE: 347
ggctcgcctc ttccatgtc                                            19

<210> SEQ ID NO 348
<211> LENGTH: 20
<212> TYPE: DNA
<213> ORGANISM: Artificial Sequence
<220> FEATURE:
<223> OTHER INFORMATION: forward primer

<400> SEQUENCE: 348
ctttgaaccc ttgcttgcaa                                           20

<210> SEQ ID NO 349
<211> LENGTH: 25
<212> TYPE: DNA
<213> ORGANISM: Artificial Sequence
<220> FEATURE:
<223> OTHER INFORMATION: probe

<400> SEQUENCE: 349
aagtcctggg tgcttctgac gcaca                                     25
```

```
<210> SEQ ID NO 350
<211> LENGTH: 18
<212> TYPE: DNA
<213> ORGANISM: Artificial Sequence
<220> FEATURE:
<223> OTHER INFORMATION: reverse primer

<400> SEQUENCE: 350
cccgggacaa agcaaatg                                                    18

<210> SEQ ID NO 351
<211> LENGTH: 19
<212> TYPE: DNA
<213> ORGANISM: Artificial Sequence
<220> FEATURE:
<223> OTHER INFORMATION: forward primer

<400> SEQUENCE: 351
ccgcaacgtg gttttctca                                                   19

<210> SEQ ID NO 352
<211> LENGTH: 22
<212> TYPE: DNA
<213> ORGANISM: Artificial Sequence
<220> FEATURE:
<223> OTHER INFORMATION: probe

<400> SEQUENCE: 352
ctcggtgttg gccatgctcc ag                                               22

<210> SEQ ID NO 353
<211> LENGTH: 21
<212> TYPE: DNA
<213> ORGANISM: Artificial Sequence
<220> FEATURE:
<223> OTHER INFORMATION: reverse primer

<400> SEQUENCE: 353
tgctgggttt ctcctcctgt t                                                21

<210> SEQ ID NO 354
<211> LENGTH: 20
<212> TYPE: DNA
<213> ORGANISM: Artificial Sequence
<220> FEATURE:
<223> OTHER INFORMATION: forward primer

<400> SEQUENCE: 354
ccagctctcc ttccagctac                                                  20

<210> SEQ ID NO 355
<211> LENGTH: 20
<212> TYPE: DNA
<213> ORGANISM: Artificial Sequence
<220> FEATURE:
<223> OTHER INFORMATION: reverse primer

<400> SEQUENCE: 355
gggtggctct cacttagctc                                                  20

<210> SEQ ID NO 356
<211> LENGTH: 24
<212> TYPE: DNA
<213> ORGANISM: Artificial Sequence
<220> FEATURE:
<223> OTHER INFORMATION: probe
```

```
<400> SEQUENCE: 356
atcaatgtcc ctgtccgagt gctg                                          24

<210> SEQ ID NO 357
<211> LENGTH: 23
<212> TYPE: DNA
<213> ORGANISM: Artificial Sequence
<220> FEATURE:
<223> OTHER INFORMATION: reverse primer

<400> SEQUENCE: 357
cacactagca ttttctccgc ata                                           23

<210> SEQ ID NO 358
<211> LENGTH: 21
<212> TYPE: DNA
<213> ORGANISM: Artificial Sequence
<220> FEATURE:
<223> OTHER INFORMATION: forward primer

<400> SEQUENCE: 358
ataccaatca ccgcacaaac c                                             21

<210> SEQ ID NO 359
<211> LENGTH: 30
<212> TYPE: DNA
<213> ORGANISM: Artificial Sequence
<220> FEATURE:
<223> OTHER INFORMATION: probe

<400> SEQUENCE: 359
tgcgctgtga ctggacttaa caaatagcct                                    30

<210> SEQ ID NO 360
<211> LENGTH: 18
<212> TYPE: DNA
<213> ORGANISM: Artificial Sequence
<220> FEATURE:
<223> OTHER INFORMATION: forward primer

<400> SEQUENCE: 360
gccatccgca aaggcttt                                                 18

<210> SEQ ID NO 361
<211> LENGTH: 18
<212> TYPE: DNA
<213> ORGANISM: Artificial Sequence
<220> FEATURE:
<223> OTHER INFORMATION: reverse primer

<400> SEQUENCE: 361
ggccattccg ccagtttc                                                 18

<210> SEQ ID NO 362
<211> LENGTH: 23
<212> TYPE: DNA
<213> ORGANISM: Artificial Sequence
<220> FEATURE:
<223> OTHER INFORMATION: probe

<400> SEQUENCE: 362
tcgcttgtca ccttgccatg tgg                                           23

<210> SEQ ID NO 363
<211> LENGTH: 20
```

```
<212> TYPE: DNA
<213> ORGANISM: Artificial Sequence
<220> FEATURE:
<223> OTHER INFORMATION: forward primer

<400> SEQUENCE: 363
gcatcaggct gtcattatgg                                                    20

<210> SEQ ID NO 364
<211> LENGTH: 20
<212> TYPE: DNA
<213> ORGANISM: Artificial Sequence
<220> FEATURE:
<223> OTHER INFORMATION: reverse primer

<400> SEQUENCE: 364
agtagttgtg ctgcccttcc                                                    20

<210> SEQ ID NO 365
<211> LENGTH: 28
<212> TYPE: DNA
<213> ORGANISM: Artificial Sequence
<220> FEATURE:
<223> OTHER INFORMATION: probe

<400> SEQUENCE: 365
tgtccttacc tgtgggagct gtaaggtc                                           28

<210> SEQ ID NO 366
<211> LENGTH: 23
<212> TYPE: DNA
<213> ORGANISM: Artificial Sequence
<220> FEATURE:
<223> OTHER INFORMATION: forward primer

<400> SEQUENCE: 366
tctccatatc tgccttgcag agt                                                23

<210> SEQ ID NO 367
<211> LENGTH: 19
<212> TYPE: DNA
<213> ORGANISM: Artificial Sequence
<220> FEATURE:
<223> OTHER INFORMATION: reverse primer

<400> SEQUENCE: 367
gcacgtgggt cagattgct                                                     19

<210> SEQ ID NO 368
<211> LENGTH: 22
<212> TYPE: DNA
<213> ORGANISM: Artificial Sequence
<220> FEATURE:
<223> OTHER INFORMATION: probe

<400> SEQUENCE: 368
tcctgcagca cctcatcggg ct                                                 22

<210> SEQ ID NO 369
<211> LENGTH: 19
<212> TYPE: DNA
<213> ORGANISM: Artificial Sequence
<220> FEATURE:
<223> OTHER INFORMATION: forward primer

<400> SEQUENCE: 369
```

-continued

```
gccctcccag tgtgcaaat                                                  19

<210> SEQ ID NO 370
<211> LENGTH: 23
<212> TYPE: DNA
<213> ORGANISM: Artificial Sequence
<220> FEATURE:
<223> OTHER INFORMATION: probe

<400> SEQUENCE: 370
tgctgtttcg acgacaccgt tcg                                             23

<210> SEQ ID NO 371
<211> LENGTH: 25
<212> TYPE: DNA
<213> ORGANISM: Artificial Sequence
<220> FEATURE:
<223> OTHER INFORMATION: reverse primer

<400> SEQUENCE: 371
cgtcgatggt attaggatag aagca                                           25

<210> SEQ ID NO 372
<211> LENGTH: 24
<212> TYPE: DNA
<213> ORGANISM: Artificial Sequence
<220> FEATURE:
<223> OTHER INFORMATION: forward primer

<400> SEQUENCE: 372
gaacttcttg agcaggagca tacc                                            24

<210> SEQ ID NO 373
<211> LENGTH: 25
<212> TYPE: DNA
<213> ORGANISM: Artificial Sequence
<220> FEATURE:
<223> OTHER INFORMATION: reverse primer

<400> SEQUENCE: 373
tccaccccca agaatatcat ctagt                                           25

<210> SEQ ID NO 374
<211> LENGTH: 25
<212> TYPE: DNA
<213> ORGANISM: Artificial Sequence
<220> FEATURE:
<223> OTHER INFORMATION: probe

<400> SEQUENCE: 374
agggcttcat aatcaccttc tgttc                                           25

<210> SEQ ID NO 375
<211> LENGTH: 20
<212> TYPE: DNA
<213> ORGANISM: Artificial Sequence
<220> FEATURE:
<223> OTHER INFORMATION: forward primer

<400> SEQUENCE: 375
cgaagccctt acaagtttcc                                                 20

<210> SEQ ID NO 376
<211> LENGTH: 20
<212> TYPE: DNA
<213> ORGANISM: Artificial Sequence
```

```
<220> FEATURE:
<223> OTHER INFORMATION: reverse primer

<400> SEQUENCE: 376
ggactcttca ggggtgaaat                                                 20

<210> SEQ ID NO 377
<211> LENGTH: 24
<212> TYPE: DNA
<213> ORGANISM: Artificial Sequence
<220> FEATURE:
<223> OTHER INFORMATION: probe

<400> SEQUENCE: 377
cccttacgga ttcctggagg gaac                                            24

<210> SEQ ID NO 378
<211> LENGTH: 20
<212> TYPE: DNA
<213> ORGANISM: Artificial Sequence
<220> FEATURE:
<223> OTHER INFORMATION: forward primer

<400> SEQUENCE: 378
ccagacgagc gattagaagc                                                 20

<210> SEQ ID NO 379
<211> LENGTH: 20
<212> TYPE: DNA
<213> ORGANISM: Artificial Sequence
<220> FEATURE:
<223> OTHER INFORMATION: reverse primer

<400> SEQUENCE: 379
tcctcctctt cctcctcctc                                                 20

<210> SEQ ID NO 380
<211> LENGTH: 23
<212> TYPE: DNA
<213> ORGANISM: Artificial Sequence
<220> FEATURE:
<223> OTHER INFORMATION: probe

<400> SEQUENCE: 380
tgtgaggtga atgatttggg gga                                             23

<210> SEQ ID NO 381
<211> LENGTH: 20
<212> TYPE: DNA
<213> ORGANISM: Artificial Sequence
<220> FEATURE:
<223> OTHER INFORMATION: forward primer

<400> SEQUENCE: 381
catcttccag gaggaccact                                                 20

<210> SEQ ID NO 382
<211> LENGTH: 20
<212> TYPE: DNA
<213> ORGANISM: Artificial Sequence
<220> FEATURE:
<223> OTHER INFORMATION: reverse primer

<400> SEQUENCE: 382
tccgaccttc aatcatttca                                                 20
```

<210> SEQ ID NO 383
<211> LENGTH: 24
<212> TYPE: DNA
<213> ORGANISM: Artificial Sequence
<220> FEATURE:
<223> OTHER INFORMATION: probe

<400> SEQUENCE: 383
ctctgtggca ccctggacta cctg                                              24

<210> SEQ ID NO 384
<211> LENGTH: 20
<212> TYPE: DNA
<213> ORGANISM: Artificial Sequence
<220> FEATURE:
<223> OTHER INFORMATION: forward primer

<400> SEQUENCE: 384
cctggaggct gcaacatacc                                                   20

<210> SEQ ID NO 385
<211> LENGTH: 23
<212> TYPE: DNA
<213> ORGANISM: Artificial Sequence
<220> FEATURE:
<223> OTHER INFORMATION: reverse primer

<400> SEQUENCE: 385
tacaatggct ttggaggata gca                                               23

<210> SEQ ID NO 386
<211> LENGTH: 25
<212> TYPE: DNA
<213> ORGANISM: Artificial Sequence
<220> FEATURE:
<223> OTHER INFORMATION: probe

<400> SEQUENCE: 386
atcctcctga agccctttc gcagc                                              25

<210> SEQ ID NO 387
<211> LENGTH: 20
<212> TYPE: DNA
<213> ORGANISM: Artificial Sequence
<220> FEATURE:
<223> OTHER INFORMATION: forward primer

<400> SEQUENCE: 387
tgttttgatt cccgggctta                                                   20

<210> SEQ ID NO 388
<211> LENGTH: 28
<212> TYPE: DNA
<213> ORGANISM: Artificial Sequence
<220> FEATURE:
<223> OTHER INFORMATION: probe

<400> SEQUENCE: 388
tgccttcttc ctccctcact tctcacct                                          28

<210> SEQ ID NO 389
<211> LENGTH: 24
<212> TYPE: DNA
<213> ORGANISM: Artificial Sequence
<220> FEATURE:
<223> OTHER INFORMATION: reverse primer

```
<400> SEQUENCE: 389
caaagctgtc agctctagca aaag                                                24

<210> SEQ ID NO 390
<211> LENGTH: 19
<212> TYPE: DNA
<213> ORGANISM: Artificial Sequence
<220> FEATURE:
<223> OTHER INFORMATION: forward primer

<400> SEQUENCE: 390
gcccgaaacg ccgaatata                                                      19

<210> SEQ ID NO 391
<211> LENGTH: 21
<212> TYPE: DNA
<213> ORGANISM: Artificial Sequence
<220> FEATURE:
<223> OTHER INFORMATION: probe

<400> SEQUENCE: 391
taccgcagca aaccgcttgg g                                                   21

<210> SEQ ID NO 392
<211> LENGTH: 23
<212> TYPE: DNA
<213> ORGANISM: Artificial Sequence
<220> FEATURE:
<223> OTHER INFORMATION: reverse primer

<400> SEQUENCE: 392
cgtggctctc ttatcctcat gat                                                 23

<210> SEQ ID NO 393
<211> LENGTH: 20
<212> TYPE: DNA
<213> ORGANISM: Artificial Sequence
<220> FEATURE:
<223> OTHER INFORMATION: forward primer

<400> SEQUENCE: 393
ggtgtgccac agaccttcct                                                     20

<210> SEQ ID NO 394
<211> LENGTH: 24
<212> TYPE: DNA
<213> ORGANISM: Artificial Sequence
<220> FEATURE:
<223> OTHER INFORMATION: reverse primer

<400> SEQUENCE: 394
acggagttct tgacagagtt ttga                                                24

<210> SEQ ID NO 395
<211> LENGTH: 27
<212> TYPE: DNA
<213> ORGANISM: Artificial Sequence
<220> FEATURE:
<223> OTHER INFORMATION: probe

<400> SEQUENCE: 395
ttggcctgta atcacctgtg cagcctt                                             27

<210> SEQ ID NO 396
```

```
<211> LENGTH: 19
<212> TYPE: DNA
<213> ORGANISM: Artificial Sequence
<220> FEATURE:
<223> OTHER INFORMATION: forward primer

<400> SEQUENCE: 396
tccctgcggt cccagatag                                            19

<210> SEQ ID NO 397
<211> LENGTH: 20
<212> TYPE: DNA
<213> ORGANISM: Artificial Sequence
<220> FEATURE:
<223> OTHER INFORMATION: reverse primer

<400> SEQUENCE: 397
gtgggaacag ggtggacact                                           20

<210> SEQ ID NO 398
<211> LENGTH: 25
<212> TYPE: DNA
<213> ORGANISM: Artificial Sequence
<220> FEATURE:
<223> OTHER INFORMATION: probe

<400> SEQUENCE: 398
atcctgcccg gagtggaact gaagc                                     25

<210> SEQ ID NO 399
<211> LENGTH: 20
<212> TYPE: DNA
<213> ORGANISM: Artificial Sequence
<220> FEATURE:
<223> OTHER INFORMATION: forward primer

<400> SEQUENCE: 399
aatccaaggg ggagagtgat                                           20

<210> SEQ ID NO 400
<211> LENGTH: 26
<212> TYPE: DNA
<213> ORGANISM: Artificial Sequence
<220> FEATURE:
<223> OTHER INFORMATION: probe

<400> SEQUENCE: 400
catatggact ttgactcagc tgtggc                                    26

<210> SEQ ID NO 401
<211> LENGTH: 20
<212> TYPE: DNA
<213> ORGANISM: Artificial Sequence
<220> FEATURE:
<223> OTHER INFORMATION: reverse primer

<400> SEQUENCE: 401
gtacagattt tgcccgagga                                           20

<210> SEQ ID NO 402
<211> LENGTH: 21
<212> TYPE: DNA
<213> ORGANISM: Artificial Sequence
<220> FEATURE:
<223> OTHER INFORMATION: forward primer

<400> SEQUENCE: 402
```

-continued tgtggacatc ttccctcag a                                          21

<210> SEQ ID NO 403
<211> LENGTH: 24
<212> TYPE: DNA
<213> ORGANISM: Artificial Sequence
<220> FEATURE:
<223> OTHER INFORMATION: probe

<400> SEQUENCE: 403
ttccctactg agccaccttc tctg                                      24

<210> SEQ ID NO 404
<211> LENGTH: 18
<212> TYPE: DNA
<213> ORGANISM: Artificial Sequence
<220> FEATURE:
<223> OTHER INFORMATION: reverse primer

<400> SEQUENCE: 404
ctagcccgac cggttcgt                                             18

<210> SEQ ID NO 405
<211> LENGTH: 24
<212> TYPE: DNA
<213> ORGANISM: Artificial Sequence
<220> FEATURE:
<223> OTHER INFORMATION: forward primer

<400> SEQUENCE: 405
ctatatgcag ccagagatgt gaca                                      24

<210> SEQ ID NO 406
<211> LENGTH: 23
<212> TYPE: DNA
<213> ORGANISM: Artificial Sequence
<220> FEATURE:
<223> OTHER INFORMATION: probe

<400> SEQUENCE: 406
acagcctgcc actcatcaca gcc                                       23

<210> SEQ ID NO 407
<211> LENGTH: 24
<212> TYPE: DNA
<213> ORGANISM: Artificial Sequence
<220> FEATURE:
<223> OTHER INFORMATION: reverse primer

<400> SEQUENCE: 407
ccacgagttt cttactgaga atgg                                      24

<210> SEQ ID NO 408
<211> LENGTH: 19
<212> TYPE: DNA
<213> ORGANISM: Artificial Sequence
<220> FEATURE:
<223> OTHER INFORMATION: forward primer

<400> SEQUENCE: 408
gggccaaata ttcagaagc                                            19

<210> SEQ ID NO 409
<211> LENGTH: 20
<212> TYPE: DNA

```
<213> ORGANISM: Artificial Sequence
<220> FEATURE:
<223> OTHER INFORMATION: reverse primer

<400> SEQUENCE: 409
ggatgggtat gatgggacag                                          20

<210> SEQ ID NO 410
<211> LENGTH: 20
<212> TYPE: DNA
<213> ORGANISM: Artificial Sequence
<220> FEATURE:
<223> OTHER INFORMATION: probe

<400> SEQUENCE: 410
ccaccatagc ggccatggag                                          20

<210> SEQ ID NO 411
<211> LENGTH: 22
<212> TYPE: DNA
<213> ORGANISM: Artificial Sequence
<220> FEATURE:
<223> OTHER INFORMATION: forward primer

<400> SEQUENCE: 411
cttcacagtg ctcctgcagt ct                                       22

<210> SEQ ID NO 412
<211> LENGTH: 21
<212> TYPE: DNA
<213> ORGANISM: Artificial Sequence
<220> FEATURE:
<223> OTHER INFORMATION: reverse primer

<400> SEQUENCE: 412
catctgcttc agctcgttgg t                                        21

<210> SEQ ID NO 413
<211> LENGTH: 26
<212> TYPE: DNA
<213> ORGANISM: Artificial Sequence
<220> FEATURE:
<223> OTHER INFORMATION: probe

<400> SEQUENCE: 413
aagtacacgt aagttacagc cacaca                                   26

<210> SEQ ID NO 414
<211> LENGTH: 18
<212> TYPE: DNA
<213> ORGANISM: Artificial Sequence
<220> FEATURE:
<223> OTHER INFORMATION: forward primer

<400> SEQUENCE: 414
gcctcggtgt gcctttca                                            18

<210> SEQ ID NO 415
<211> LENGTH: 22
<212> TYPE: DNA
<213> ORGANISM: Artificial Sequence
<220> FEATURE:
<223> OTHER INFORMATION: probe

<400> SEQUENCE: 415
catcgccagc tacgccctgc tc                                       22
```

```
<210> SEQ ID NO 416
<211> LENGTH: 19
<212> TYPE: DNA
<213> ORGANISM: Artificial Sequence
<220> FEATURE:
<223> OTHER INFORMATION: reverse primer

<400> SEQUENCE: 416
cgtgatgtgc gcaatcatg                                              19

<210> SEQ ID NO 417
<211> LENGTH: 19
<212> TYPE: DNA
<213> ORGANISM: Artificial Sequence
<220> FEATURE:
<223> OTHER INFORMATION: forward primer

<400> SEQUENCE: 417
gtggatgtgc cctgaagga                                              19

<210> SEQ ID NO 418
<211> LENGTH: 20
<212> TYPE: DNA
<213> ORGANISM: Artificial Sequence
<220> FEATURE:
<223> OTHER INFORMATION: reverse primer

<400> SEQUENCE: 418
ctgcggatcc agggtaagaa                                             20

<210> SEQ ID NO 419
<211> LENGTH: 28
<212> TYPE: DNA
<213> ORGANISM: Artificial Sequence
<220> FEATURE:
<223> OTHER INFORMATION: probe

<400> SEQUENCE: 419
aagccaggcg tctacacgag agtctcac                                    28

<210> SEQ ID NO 420
<211> LENGTH: 20
<212> TYPE: DNA
<213> ORGANISM: Artificial Sequence
<220> FEATURE:
<223> OTHER INFORMATION: forward primer

<400> SEQUENCE: 420
gccctggatt tcagaaagag                                             20

<210> SEQ ID NO 421
<211> LENGTH: 20
<212> TYPE: DNA
<213> ORGANISM: Artificial Sequence
<220> FEATURE:
<223> OTHER INFORMATION: reverse primer

<400> SEQUENCE: 421
agttacaagc cagggaagga                                             20

<210> SEQ ID NO 422
<211> LENGTH: 25
<212> TYPE: DNA
<213> ORGANISM: Artificial Sequence
<220> FEATURE:
```

```
<223> OTHER INFORMATION: probe

<400> SEQUENCE: 422
caagtctgga tctgggaccc tttcc                                          25

<210> SEQ ID NO 423
<211> LENGTH: 20
<212> TYPE: DNA
<213> ORGANISM: Artificial Sequence
<220> FEATURE:
<223> OTHER INFORMATION: forward primer

<400> SEQUENCE: 423
ctgctgtctt gggtgcattg                                                20

<210> SEQ ID NO 424
<211> LENGTH: 18
<212> TYPE: DNA
<213> ORGANISM: Artificial Sequence
<220> FEATURE:
<223> OTHER INFORMATION: reverse primer

<400> SEQUENCE: 424
gcagcctggg accacttg                                                  18

<210> SEQ ID NO 425
<211> LENGTH: 25
<212> TYPE: DNA
<213> ORGANISM: Artificial Sequence
<220> FEATURE:
<223> OTHER INFORMATION: probe

<400> SEQUENCE: 425
ttgccttgct gctctacctc cacca                                          25

<210> SEQ ID NO 426
<211> LENGTH: 19
<212> TYPE: DNA
<213> ORGANISM: Artificial Sequence
<220> FEATURE:
<223> OTHER INFORMATION: forward primer

<400> SEQUENCE: 426
tgacgatggc ctggagtgt                                                 19

<210> SEQ ID NO 427
<211> LENGTH: 22
<212> TYPE: DNA
<213> ORGANISM: Artificial Sequence
<220> FEATURE:
<223> OTHER INFORMATION: reverse primer

<400> SEQUENCE: 427
ggtaccggat catgaggatc tg                                             22

<210> SEQ ID NO 428
<211> LENGTH: 21
<212> TYPE: DNA
<213> ORGANISM: Artificial Sequence
<220> FEATURE:
<223> OTHER INFORMATION: probe

<400> SEQUENCE: 428
ctgggcagca ccaagtccgg a                                              21
```

```
<210> SEQ ID NO 429
<211> LENGTH: 22
<212> TYPE: DNA
<213> ORGANISM: Artificial Sequence
<220> FEATURE:
<223> OTHER INFORMATION: forward primer

<400> SEQUENCE: 429
agaggcatcc atgaacttca ca                                              22

<210> SEQ ID NO 430
<211> LENGTH: 24
<212> TYPE: DNA
<213> ORGANISM: Artificial Sequence
<220> FEATURE:
<223> OTHER INFORMATION: reverse primer

<400> SEQUENCE: 430
caaactccac agtacttggg ttga                                            24

<210> SEQ ID NO 431
<211> LENGTH: 20
<212> TYPE: DNA
<213> ORGANISM: Artificial Sequence
<220> FEATURE:
<223> OTHER INFORMATION: probe

<400> SEQUENCE: 431
cgggctgcat cagcacacgc                                                 20

<210> SEQ ID NO 432
<211> LENGTH: 23
<212> TYPE: DNA
<213> ORGANISM: Artificial Sequence
<220> FEATURE:
<223> OTHER INFORMATION: forward primer

<400> SEQUENCE: 432
gcagttggaa gacacaggaa agt                                             23

<210> SEQ ID NO 433
<211> LENGTH: 27
<212> TYPE: DNA
<213> ORGANISM: Artificial Sequence
<220> FEATURE:
<223> OTHER INFORMATION: probe

<400> SEQUENCE: 433
tccccaaatt gcagatttat caacggc                                         27

<210> SEQ ID NO 434
<211> LENGTH: 21
<212> TYPE: DNA
<213> ORGANISM: Artificial Sequence
<220> FEATURE:
<223> OTHER INFORMATION: reverse primer

<400> SEQUENCE: 434
tgcgtggcac tattttcaag a                                               21

<210> SEQ ID NO 435
<211> LENGTH: 25
<212> TYPE: DNA
<213> ORGANISM: Artificial Sequence
<220> FEATURE:
<223> OTHER INFORMATION: forward primer
```

```
<400> SEQUENCE: 435
agactgtgga gtttgatgtt gttga                                        25

<210> SEQ ID NO 436
<211> LENGTH: 22
<212> TYPE: DNA
<213> ORGANISM: Artificial Sequence
<220> FEATURE:
<223> OTHER INFORMATION: reverse primer

<400> SEQUENCE: 436
ggaacaccac caggacctgt aa                                           22

<210> SEQ ID NO 437
<211> LENGTH: 23
<212> TYPE: DNA
<213> ORGANISM: Artificial Sequence
<220> FEATURE:
<223> OTHER INFORMATION: probe

<400> SEQUENCE: 437
ttgctgcctc cgcacccttt tct                                          23

<210> SEQ ID NO 438
<211> LENGTH: 20
<212> TYPE: DNA
<213> ORGANISM: Artificial Sequence
<220> FEATURE:
<223> OTHER INFORMATION: forward primer

<400> SEQUENCE: 438
acccagtagc aaggagaagc                                              20

<210> SEQ ID NO 439
<211> LENGTH: 20
<212> TYPE: DNA
<213> ORGANISM: Artificial Sequence
<220> FEATURE:
<223> OTHER INFORMATION: reverse primer

<400> SEQUENCE: 439
cagctggtgg taggttctga                                              20

<210> SEQ ID NO 440
<211> LENGTH: 21
<212> TYPE: DNA
<213> ORGANISM: Artificial Sequence
<220> FEATURE:
<223> OTHER INFORMATION: probe

<400> SEQUENCE: 440
cactcactgc tccgagtgcg g                                            21
```

GENE EXPRESSION MARKERS FOR BREAST CANCER PROGNOSIS

This application claims priority under 35 U.S.C. § 119(e) to provisional application Ser. No. 60/440,861 filed on Jan. 15, 2003, the entire disclosure of which is hereby expressly incorporated by reference.

BACKGROUND OF THE INVENTION

1. Field of the Invention

The present invention provides genes and gene sets the expression of which is important in the diagnosis and/or prognosis of breast cancer.

2. Description of the Related Art

Oncologists have a number of treatment options available to them, including different combinations of chemotherapeutic drugs that are characterized as "standard of care," and a number of drugs that do not carry a label claim for particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286: 531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001)). Certain classifications of human breast cancers based on gene expression patterns have also been reported (Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed hundreds of genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as ErbB2$^+$ subgroup, and subgroups characterized by low to absent gene expression of the estrogen receptor (ER) and a few additional transcriptional factors (Perou et al., *Nature* 406:747-752 (2000)) does not reflect the cellular and molecular heterogeneity of breast cancer, and does not allow the design of treatment strategies maximizing patient response.

SUMMARY OF THE INVENTION

The present invention provides a set of genes, the expression of which has prognostic value, specifically with respect to disease-free survival.

The present invention accommodates the use of archived paraffin-embedded biopsy material for assay of all markers in the set, and therefore is compatible with the most widely available type of biopsy material. It is also compatible with several different methods of tumor tissue harvest, for example, via core biopsy or fine needle aspiration. Further, for each member of the gene set, the invention specifies oligonucleotide sequences that can be used in the test.

In one aspect, the invention concerns a method of predicting the likelihood of long-term survival of a breast cancer patient without the recurrence of breast cancer, comprising determining the expression level of one or more prognostic RNA transcripts or their expression products in a breast cancer tissue sample obtained from the patient, normalized against the expression level of all RNA transcripts or their products in the breast cancer tissue sample, or of a reference set of RNA transcripts or their expression products, wherein the prognostic RNA transcript is the transcript of one or more genes selected from the group consisting of: TP53BP2, GRB7, PR, CD68, Bcl2, KRT14, IRS1, CTSL, EstR1, Chk1, IGFBP2, BAG1, CEGP1, STK15, GSTM1, FHIT, RIZ1, AIB1, SURV, BBC3, IGF1R, p27, GATA3, ZNF217, EGFR, CD9, MYBL2, HIF1α, pS2, ErbB3, TOP2B, MDM2, RAD51C, KRT19, TS, Her2, KLK10, β-Catenin, γ-Catenin, MCM2, PI3KC2A, IGF1, TBP, CCNB1, FBXO5, and DR5, wherein expression of one or more of GRB7, CD68, CTSL, Chk1, AIB1, CCNB1, MCM2, FBXO5, Her2, STK15, SURV, EGFR, MYBL2, HIF1α, and TS indicates a decreased likelihood of long-term survival without breast cancer recurrence, and the expression of one or more of TP53BP2, PR, Bcl2, KRT14, EstR1, IGFBP2, BAG1, CEGP1, KLK10, β-Catenin, γ-Catenin, DR5, PI3KCA2, RAD51C, GSTM1, FHIT, RIZ1, BBC3, TBP, p27, IRS1, IGF1R, GATA3, ZNF217, CD9, pS2, ErbB3, TOP2B, MDM2, IGF1, and KRT19 indicates an increased likelihood of long-term survival without breast cancer recurrence.

In a particular embodiment, the expression levels of at least two, or at least 5, or at least 10, or at least 15 of the prognostic RNA transcripts or their expression products are determined. In another embodiment, the method comprises the determination of the expression levels of all prognostic RNA transcripts or their expression products.

In another particular embodiment, the breast cancer is invasive breast carcinoma.

In a further embodiment, RNA is isolated from a fixed, wax-embedded breast cancer tissue specimen of the patient. Isolation may be performed by any technique known in the art, for example from core biopsy tissue or fine needle aspirate cells.

In another aspect, the invention concerns an array comprising polynucleotides hybridizing to two or more of the following genes: α-Catenin, AIB1, AKT1, AKT2, β-actin, BAG1, BBC3, Bcl2, CCNB1, CCND1, CD68, CD9, CDH1, CEGP1, Chk1, CIAP1, cMet.2, Contig 27882, CTSL, DR5, EGFR, EIF4E, EPHX1, ErbB3, EstR1, FBXO5, FHIT1 FRP1, GAPDH, GATA3, G-Catenin, GRB7, GRO1, GSTM1, GUS, HER2, HIF1A, HNF3A, IGF1R, IGFBP2, KLK10, KRT14, KRT17, KRT18, KRT19, KRT5, Maspin, MCM2, MCM3, MDM2, MMP9, MTA1, MYBL2, P14ARF, p27, P53, PI3KC2A, PR, PRAME, pS2, RAD51C, 3RB1, RIZ1, STK15, STMY3, SURV, TGFA, TOP2B, TP53BP2, TRAIL, TS, upa, VDR, VEGF, and ZNF217.

In particular embodiments, the array comprises polynucleotides hybridizing to at least 3, or at least 5, or at least 10, or at least 15, or at least 20, or all of the genes listed above.

In another specific embodiment, the array comprises polynucleotides hybridizing to the following genes: TP53BP2, GRB7, PR, CD68, Bcl2, KRT14, IRS1, CTSL, EstR1, Chk1, IGFBP2, BAG1, CEGP1, STK15, GSTM1, FHIT, RIZ1, AIB1, SURV, BBC3, IGF1R, p27, GATA3, ZNF217, EGFR, CD9, MYBL2, HIF1α, pS2, RIZ1, ErbB3, TOP2B, MDM2, RAD51C, KRT19, TS, Her2, KLK10, β-Catenin, γ-Catenin, MCM2, PI3KC2A, IGF1, TBP, CCNB1, FBXO5 and DR5.

The polynucleotides can be cDNAs, or oligonucleotides, and the solid surface on which they are displayed may, for example, be glass.

In another aspect, the invention concerns a method of predicting the likelihood of long-term survival of a patient diagnosed with invasive breast cancer, without the recurrence of breast cancer, comprising the steps of:
  (1) determining the expression levels of the RNA transcripts or the expression products of genes or a gene set selected from the group consisting of
  (a) TP53BP2, Bcl2, BAD, EPHX1, PDGFRβ, DIABLO, XIAP, YB1, CA9, and KRT8;
  (b) GRB7, CD68, TOP2A, Bcl2, DIABLO, CD3, ID1, PPM1D, MCM6, and WISP1;
  (c) PR, TP53BP2, PRAME, DIABLO, CTSL, IGFBP2, TIMP1, CA9, MMP9, and COX2;
  (d) CD68, GRB7, TOP2A, Bcl2, DIABLO, CD3, ID1, PPM1D, MCM6, and WISP1;
  (e) Bcl2, TP53BP2, BAD, EPHX1, PDGFRβ, DIABLO, XIAP, YB1, CA9, and KRT8;
  (f) KRT14, KRT5, PRAME, TP53BP2, GUS1, AIB1, MCM3, CCNE1, MCM6, and ID1;
  (g) PRAME, TP53BP2, EstR1, DIABLO, CTSL, PPM1D, GRB7, DAPK1, BBC3, and VEGFB;
  (h) CTSL2, GRB7, TOP2A, CCNB1, Bcl2, DIABLO, PRAME, EMS1, CA9, and EpCAM;
  (i) EstR1, TP53BP2, PRAME, DIABLO, CTSL, PPM1D, GRB7, DAPK1, BBC3, and VEGFB;
  (k) Chk1, PRAME, TP53BP2, GRB7, CA9, CTSL, CCNB1, TOP2A, tumor size, and IGFBP2;
  (l) IGFBP2, GRB7, PRAME, DIABLO, CTSL, β-Catenin, PPM1D, Chk1, WISP1, and LOT1;
  (m) HER2, TP53BP2, Bcl2, DIABLO, TIMP1, EPHX1, TOP2A, TRAIL, CA9, and AREG;
  (n) BAG1, TP53BP2, PRAME, IL6, CCNB1, PAI1, AREG, tumor size, CA9, and Ki67;
  (o) CEGP1, TP53BP2, PRAME, DIABLO, Bcl2, COX2, CCNE1, STK15, and AKT2, and FGF18;
  (p) STK15, TP53BP2, PRAME, IL6, CCNE1, AKT2, DIABLO, cMet, CCNE2, and COX2;
  (q) KLK10, EstR1, TP53BP2, PRAME, DIABLO, CTSL, PPM1D, GRB7, DAPK1, and BBC3;
  (r) AIB1, TP53BP2, Bcl2, DIABLO, TIMP1, CD3, p53, CA9, GRB7, and EPHX1
  (s) BBC3, GRB7, CD68, PRAME, TOP2A, CCNB1, EPHX1, CTSL GSTM1, and APC;
  (t) CD9, GRB7, CD68, TOP2A, Bcl2, CCNB1, CD3, DIABLO, ID1, and PPM1D;
  (w) EGFR, KRT14, GRB7, TOP2A, CCNB1, CTSL, Bcl2, TP, KLK10, and CA9;
  (x) HIF1α, PR, DIABLO, PRAME, Chk1, AKT2, GRB7, CCNE1, TOP2A, and CCNB1;
  (y) MDM2, TP53BP2, DIABLO, Bcl2, AIB1, TIMP1, CD3, p53, CA9, and HER2;
  (z) MYBL2, TP53BP2, PRAME, IL6, Bcl2, DIABLO, CCNE1, EPHX1, TIMP1, and CA9;
  (aa) p27, TP53BP2, PRAME, DIABLO, Bcl2, COX2, CCNE1, STK15, AKT2, and ID1;
  (ab) RAD51, GRB7, CD68, TOP2A, CIAP2, CCNB1, BAG1, IL6, FGFR1, and TP53BP2;
  (ac) SURV, GRB7, TOP2A, PRAME, CTSL, GSTM1, CCNB1, VDR, CA9; and CCNE2;
  (ad) TOP2B, TP53BP2, DIABLO, Bcl2, TIMP1, AIB1, CA9, p53, KRT8, and BAD;
  (ae) ZNF217, GRB7, TP53BP2, PRAME, DIABLO, Bcl2, COX2, CCNE1, APC4, and β-Catenin, in a breast cancer tissue sample obtained from the patient, normalized against the expression levels of all RNA transcripts or their expression products in said breast cancer tissue sample, or of a reference set of RNA transcripts or their products;
  (2) subjecting the data obtained in step (1) to statistical analysis; and
  (3) determining whether the likelihood of said long-term survival has increased or decreased.

In a further aspect, the invention concerns a method of predicting the likelihood of long-term survival of a patient diagnosed with estrogen receptor (ER)-positive invasive breast cancer, without the recurrence of breast cancer, comprising the steps of:
  (1) determining the expression levels of the RNA transcripts or the expression products of genes of a gene set selected from the group consisting of CD68; CTSL; FBXO5; SURV; CCNB1; MCM2; Chk1; MYBL2; HIF1A; cMET; EGFR; TS; STK15, IGFR1; BC12; HNF3A; TP53BP2; GATA3; BBC3; RAD51C; BAG1; IGFBP2; PR; CD9; RB1; EPHX1; CEGP1; TRAIL; DR5; p27; p53; MTA; RIZ1; ErbB3; TOP2B; EIF4E, wherein expression of the following genes in ER-positive cancer is indicative of a reduced likelihood of survival without cancer recurrence following surgery: CD68; CTSL; FBXO5; SURV; CCNB1; MCM2; Chk1; MYBL2; HIF1A; cMET; EGFR; TS; STK15, and wherein expression of the following genes is indicative of a better prognosis for survival without cancer recurrence following surgery: IGFR1; BC12; HNF3A; TP53BP2; GATA3; BBC3; RAD51C; BAG1; IGFBP2;

PR; CD9; RB1; EPHX1; CEGP1; TRAIL; DR5; p27; p53; MTA; RIZ1; ErbB3; TOP2B; EIF4E.
(2) subjecting the data obtained in step (1) to statistical analysis; and
(3) determining whether the likelihood of said long-term survival has increased or decreased.

In yet another aspect, the invention concerns a method of predicting the likelihood of long-term survival of a patient diagnosed with estrogen receptor (ER)-negative invasive breast cancer, without the recurrence of breast cancer, comprising determining the expression levels of the RNA transcripts or the expression products of genes of the gene set CCND1; UPA; HNF3A; CDH1; Her2; GRB7; AKT1; STMY3; α-Catenin; VDR; GRO1; KT14; KLK10; Maspin, TGFα, and FRP1, wherein expression of the following genes is indicative of a reduced likelihood of survival without cancer recurrence: CCND1; UPA; HNF3A; CDH1; Her2; GRB7; AKT1; STMY3; α-Catenin; VDR; GRO1, and wherein expression of the following genes is indicative of a better prognosis for survival without cancer recurrence: KT14; KLK10; Maspin, TGFα, and FRP1.

In a different aspect, the invention concerns a method of preparing a personalized genomics profile for a patient, comprising the steps of:
(a) subjecting RNA extracted from a breast tissue obtained from the patient to gene expression analysis;
(b) determining the expression level of one or more genes selected from the breast cancer gene set listed in any one of Tables 1-5, wherein the expression level is normalized against a control gene or genes and optionally is compared to the amount found in a breast cancer reference tissue set; and
(c) creating a report summarizing the data obtained by the gene expression analysis.

The report may, for example, include prediction of the likelihood of long term survival of the patient and/or recommendation for a treatment modality of said patient.

In a further aspect, the invention concerns a method for amplification of a gene listed in Tables 5A and B by polymerase chain reaction (PCR), comprising performing said PCR by using an amplicon listed in Tables 5A and B and a primer-probe set listed in Tables 6A-F.

In a still further aspect, the invention concerns a PCR amplicon listed in Tables 5A and B.

In yet another aspect, the invention concerns a PCR primer-probe set listed in Tables 6A-F.

The invention further concerns a prognostic method comprising:
(a) subjecting a sample comprising breast cancer cells obtained from a patient to quantitative analysis of the expression level of the RNA transcript of at least one gene selected from the group consisting of GRB7, CD68, CTSL, Chk1, AIB1, CCNB1, MCM2, FBXO5, Her2, STK15, SURV, EGFR, MYBL2, HIF1α, and TS, or their product, and
(b) identifying the patient as likely to have a decreased likelihood of long-term survival without breast cancer recurrence if the normalized expression levels of the gene or genes, or their products, are elevated above a defined expression threshold.

In a different aspect, the invention concerns a prognostic method comprising:
(a) subjecting a sample comprising breast cancer cells obtained from a patient to quantitative analysis of the expression level of the RNA transcript of at least one gene selected from the group consisting of TP53BP2, PR, Bcl2, KRT14, EstR1, IGFBP2, BAG1, CEGP1, KLK10, β-Catenin, γ-Catenin, DR5, PI3KCA2, RAD51C, GSTM1, FHIT, RIZ1, BBC3, TBP, p27, IRS1, IGF1R, GATA3, ZNF217, CD9, pS2, ErbB3, TOP2B, MDM2, IGF1, and KRT19, and
(b) identifying the patient as likely to have an increased likelihood of long-term survival without breast cancer recurrence if the normalized expression levels of the gene or genes, or their products, are elevated above a defined expression threshold.

The invention further concerns a kit comprising one or more of (1) extraction buffer/reagents and protocol; (2) reverse transcription buffer/reagents and protocol; and (3) qPCR buffer/reagents and protocol suitable for performing any of the foregoing methods.

BRIEF DESCRIPTION OF THE DRAWINGS

Table 1 is a list of genes, expression of which correlate with breast cancer survival. Results from a retrospective clinical trial. Binary statistical analysis.

Table 2 is a list of genes, expression of which correlates with breast cancer survival in estrogen receptor (ER) positive patients. Results from a retrospective clinical trial. Binary statistical analysis.

Table 3 is a list of genes, expression of which correlates with breast cancer survival in estrogen receptor (ER) negative patients. Results from a retrospective clinical trial. Binary statistical analysis.

Table 4 is a list of genes, expression of which correlates with breast cancer survival. Results from a retrospective clinical trial. Cox proportional hazards statistical analysis.

Tables 5A and B show a list of genes, expression of which correlate with breast cancer survival. Results from a retrospective clinical trial. The table includes accession numbers for the genes, and amplicon sequences used for PCR amplification.

Tables 6A-6F The table includes sequences for the forward and reverse primers (designated by "f" and "r", respectively) and probes (designated by "p") used for PCR amplification of the amplicons listed in Tables 5A-B.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "diagnosis" is used herein to refer to the identification of a molecular or pathological state, disease or condition, such as the identification of a molecular subtype of head and neck cancer, colon cancer, or other type of cancer.

The term "prognosis" is used herein to refer to the prediction of the likelihood of cancer-attributable death or progression, including recurrence, metastatic spread, and drug resistance, of a neoplastic disease, such as breast cancer.

The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following sugery and/or termination of chemotherapy or other treatment modalities is likely.

The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The terms "expression threshold," and "defined expression threshold" are used interchangeably and refer to the level of a gene or gene product in question above which the gene or gene product serves as a predictive marker for patient survival without cancer recurrence. The threshold is defined experimentally from clinical studies such as those described in the Example below. The expression threshold can be selected either for maximum sensitivity, or for maximum selectivity, or for minimum error. The determination of the expression threshold for any situation is well within the knowledge of those skilled in the art.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles {for example: T. E. Godfrey et al, J. Molec. Diagnostics 2: 84-91 [2000]; K. Specht et al., Am. J. Pathol. 158: 419-29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386)

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

5. MassARRAY Technology

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dipensed on a chip array that is pre-loaded with the components needed for MALTI-TOF MS sample preparation. The various cDNAs present in the reaction are quantitated by analyzing the peak areas in the mass spectrum obtained.

6. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

7. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

8. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

9. General Description of the mRNA Isolation, Purification and Amplification

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84-91 [2000]; K. specht et al., Am. J. Pathol.

158: 419-29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined.

10. Breast Cancer Gene Set, Assayed Gene Subsequences, and Clinical Application of Gene Expression Data An important aspect of the present invention is to use the measured expression of certain genes by breast cancer tissue to provide prognostic information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) of tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

Further details of the invention will be described in the following non-limiting Example

EXAMPLE

A Phase II Study of Gene Expression in 79 Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival.

Study Design

Molecular assays were performed on paraffin-embedded, formalin-fixed primary breast tumor tissues obtained from 79 individual patients diagnosed with invasive breast cancer. All patients in the study had 10 or more positive nodes. Mean age was 57 years, and mean clinical tumor size was 4.4 cm. Patients were included in the study only if histopathologic assessment, performed as described in the Materials and Methods section, indicated adequate amounts of tumor tissue and homogeneous pathology.

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, the block most representative of the pathology was used for analysis.

Gene Expression Analysis mRNA was extracted and purified from fixed, paraffin-embedded tissue samples, and prepared for gene expression analysis as described in section 9 above.

Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the median of the 7 reference genes for that particular patient. Clinical outcome data were available for all patients from a review of registry data and selected patient charts.

Outcomes were classified as:
0 died due to breast cancer or to unknown cause or alive with breast cancer recurrence;
1 alive without breast cancer recurrence or died due to a cause other than breast cancer Analysis was performed by:
1. Analysis of the relationship between normalized gene expression and the binary outcomes of 0 or 1.
2. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of Patients with Invasive Breast Carcinoma by Binary Approach

In the first (binary) approach, analysis was performed on all 79 patients with invasive breast carcinoma. A t test was performed on the groups of patients classified as either no recurrence and no breast cancer related death at three years, versus recurrence, or breast cancer-related death at three years, and the p-values for the differences between the groups for each gene were calculated.

Table 1 lists the 47 genes for which the p-value for the differences between the groups was <0.10. The first column of mean expression values pertains to patients who neither had a metastatic recurrence of nor died from breast cancer. The second column of mean expression values pertains to patients who either had a metastatic recurrence of or died from breast cancer.

TABLE 1

|         | Mean      | Mean      | t-value  | df | p        | Valid N | Valid N |
|---------|-----------|-----------|----------|----|----------|---------|---------|
| Bcl2    | -0.15748  | -1.22816  | 4.00034  | 75 | 0.000147 | 35      | 42      |
| PR      | -2.67225  | -5.49747  | 3.61540  | 75 | 0.000541 | 35      | 42      |
| IGF1R   | -0.59390  | -1.71506  | 3.49158  | 75 | 0.000808 | 35      | 42      |
| BAG1    | 0.18844   | -0.68509  | 3.42973  | 75 | 0.000985 | 35      | 42      |
| CD68    | -0.52275  | 0.10983   | -3.41186 | 75 | 0.001043 | 35      | 42      |
| EstR1   | -0.35581  | -3.00699  | 3.32190  | 75 | 0.001384 | 35      | 42      |
| CTSL    | -0.64894  | -0.09204  | -3.26781 | 75 | 0.001637 | 35      | 42      |
| IGFBP2  | -0.81181  | -1.78398  | 3.24158  | 75 | 0.001774 | 35      | 42      |
| GATA3   | 1.80525   | 0.57428   | 3.15608  | 75 | 0.002303 | 35      | 42      |
| TP53BP2 | -4.71118  | -6.09289  | 3.02888  | 75 | 0.003365 | 35      | 42      |
| EstR1   | 3.67801   | 1.64693   | 3.01073  | 75 | 0.003550 | 35      | 42      |
| CEGP1   | -2.02566  | -4.25537  | 2.85620  | 75 | 0.005544 | 35      | 42      |
| SURV    | -3.67493  | -2.96982  | -2.70544 | 75 | 0.008439 | 35      | 42      |
| p27     | 0.80789   | 0.28807   | 2.55401  | 75 | 0.012678 | 35      | 42      |
| Chk1    | -3.37981  | -2.80389  | -2.46979 | 75 | 0.015793 | 35      | 42      |
| BBC3    | -4.71789  | -5.62957  | 2.46019  | 75 | 0.016189 | 35      | 42      |
| ZNF217  | 1.10038   | 0.62730   | 2.42282  | 75 | 0.017814 | 35      | 42      |
| EGFR    | -2.88172  | -2.20556  | -2.34774 | 75 | 0.021527 | 35      | 42      |
| CD9     | 1.29955   | 0.91025   | 2.31439  | 75 | 0.023386 | 35      | 42      |
| MYBL2   | -3.77489  | -3.02193  | -2.29042 | 75 | 0.024809 | 35      | 42      |
| HIF1A   | -0.44248  | 0.03740   | -2.25950 | 75 | 0.026757 | 35      | 42      |
| GRB7    | -1.96063  | -1.05007  | -2.25801 | 75 | 0.026854 | 35      | 42      |
| pS2     | -1.00691  | -3.13749  | 2.24070  | 75 | 0.028006 | 35      | 42      |
| RIZ1    | -7.62149  | -8.38750  | 2.20226  | 75 | 0.030720 | 35      | 42      |
| ErbB3   | -6.89508  | -7.44326  | 2.16127  | 75 | 0.033866 | 35      | 42      |
| TOP2B   | 0.45122   | 0.12665   | 2.14616  | 75 | 0.035095 | 35      | 42      |
| MDM2    | 1.09049   | 0.69001   | 2.10967  | 75 | 0.038223 | 35      | 42      |
| PRAME   | -6.40074  | -7.70424  | 2.08126  | 75 | 0.040823 | 35      | 42      |
| GUS     | -1.51683  | -1.89280  | 2.05200  | 75 | 0.043661 | 35      | 42      |
| RAD51C  | -5.85618  | -6.71334  | 2.04575  | 75 | 0.044288 | 35      | 42      |
| AIB1    | -3.08217  | -2.28784  | -2.00600 | 75 | 0.048462 | 35      | 42      |
| STK15   | -3.11307  | -2.59454  | -2.00321 | 75 | 0.048768 | 35      | 42      |
| GAPDH   | -0.35829  | -0.02292  | -1.94326 | 75 | 0.055737 | 35      | 42      |
| FHIT    | -3.00431  | -3.67175  | 1.86927  | 75 | 0.065489 | 35      | 42      |
| KRT19   | 2.52397   | 2.01694   | 1.85741  | 75 | 0.067179 | 35      | 42      |
| TS      | -2.83607  | -2.29048  | -1.83712 | 75 | 0.070153 | 35      | 42      |
| GSTM1   | -3.69140  | -4.38623  | 1.83397  | 75 | 0.070625 | 35      | 42      |
| G-Catenin | 0.31875 | -0.15524  | 1.80823  | 75 | 0.074580 | 35      | 42      |
| AKT2    | 0.78858   | 0.46703   | 1.79276  | 75 | 0.077043 | 35      | 42      |
| CCNB1   | -4.26197  | -3.51628  | -1.78803 | 75 | 0.077810 | 35      | 42      |
| PI3KC2A | -2.27401  | -2.70265  | 1.76748  | 75 | 0.081215 | 35      | 42      |
| FBXO5   | -4.72107  | -4.24411  | -1.75935 | 75 | 0.082596 | 35      | 42      |
| DR5     | -5.80850  | -6.55501  | 1.74345  | 75 | 0.085353 | 35      | 42      |
| CIAP1   | -2.81825  | -3.09921  | 1.72480  | 75 | 0.088683 | 35      | 42      |
| MCM2    | -2.87541  | -2.50683  | -1.72061 | 75 | 0.089445 | 35      | 42      |
| CCND1   | 1.30995   | 0.80905   | 1.68794  | 75 | 0.095578 | 35      | 42      |
| EIF4E   | -5.37657  | -6.47156  | 1.68169  | 75 | 0.096788 | 35      | 42      |

In the foregoing Table 1, negative t-values indicate higher expression, associated with worse outcomes, and, inversely, higher (positive) t-values indicate higher expression associated with better outcomes. Thus, for example, elevated expression of the CD68 gene (t-value=-3.41, CT mean alive<CT mean deceased) indicates a reduced likelihood of disease free survival. Similarly, elevated expression of the BC12 gene (t-value=4.00; CT mean alive>CT mean deceased) indicates an increased likelihood of disease free survival.

Based on the data set forth in Table 1, the expression of any of the following genes in breast cancer above a defined expression threshold indicates a reduced likelihood of survival without cancer recurrence following surgery: Grb7, CD68, CTSL, Chk1, Her2, STK15, AIB1, SURV, EGFR, MYBL2, HIF1α.

Based on the data set forth in Table 1, the expression of any of the following genes in breast cancer above a defined expression threshold indicates a better prognosis for survival without cancer recurrence following surgery: TP53BP2, PR, Bc12, KRT14, EstR1, IGFBP2, BAG1, CEGP1, KLK10, β Catenin, GSTM1, FHIT, Riz1, IGF1, BBC3, IGFR1, TBP, p27, IRS1, IGF1R, GATA3, CEGP1, ZNF217, CD9, pS2, ErbB3, TOP2B, MDM2, RAD51, and KRT19.

Analysis of ER Positive Patients by Binary Approach 57 patients with normalized CT for estrogen receptor (ER) >0 (i.e., ER positive patients) were subjected to separate analysis. A t test was performed on the two groups of patients classified as either no recurrence and no breast cancer related death at three years, or recurrence or breast cancer-related death at three years, and the p-values for the differences between the groups for each gene were calculated. Table 2, below, lists the genes where the p-value for the differences between the groups was <0.105. The first column of mean expression values pertains to patients who neither had a metastatic recurrence nor died from breast cancer. The second column of mean expression values pertains to patients who either had a metastatic recurrence of or died from breast cancer.

TABLE 2

|        | Mean     | Mean     | t-value  | df | p        | Valid N | Valid N |
|--------|----------|----------|----------|----|----------|---------|---------|
| IGF1R  | -0.13975 | -1.00435 | 3.65063  | 55 | 0.000584 | 30      | 27      |
| Bcl2   | 0.15345  | -0.70480 | 3.55488  | 55 | 0.000786 | 30      | 27      |
| CD68   | -0.54779 | 0.19427  | -3.41818 | 55 | 0.001193 | 30      | 27      |
| HNF3A  | 0.39617  | -0.63802 | 3.20750  | 55 | 0.002233 | 30      | 27      |
| CTSL   | -0.66726 | 0.00354  | -3.20692 | 55 | 0.002237 | 30      | 27      |
| TP53BP2| -4.81858 | -6.44425 | 3.13698  | 55 | 0.002741 | 30      | 27      |
| GATA3  | 2.33386  | 1.40803  | 3.02958  | 55 | 0.003727 | 30      | 27      |
| BBC3   | -4.54979 | -5.72333 | 2.91943  | 55 | 0.005074 | 30      | 27      |
| RAD51C | -5.63363 | -6.94841 | 2.85475  | 55 | 0.006063 | 30      | 27      |
| BAG1   | 0.31087  | -0.50669 | 2.61524  | 55 | 0.011485 | 30      | 27      |
| IGFBP2 | -0.49300 | -1.30983 | 2.59121  | 55 | 0.012222 | 30      | 27      |
| FBXO5  | -4.86333 | -4.05564 | -2.56325 | 55 | 0.013135 | 30      | 27      |
| EstR1  | 0.68368  | -0.66555 | 2.56090  | 55 | 0.013214 | 30      | 27      |
| PR     | -1.89094 | -3.86602 | 2.52803  | 55 | 0.014372 | 30      | 27      |
| SURV   | -3.87857 | -3.10970 | -2.49622 | 55 | 0.015579 | 30      | 27      |
| CD9    | 1.41691  | 0.91725  | 2.43043  | 55 | 0.018370 | 30      | 27      |
| RB1    | -2.51662 | -2.97419 | 2.41221  | 55 | 0.019219 | 30      | 27      |
| EPHX1  | -3.91703 | -5.85097 | 2.29491  | 55 | 0.025578 | 30      | 27      |
| CEGP1  | -1.18600 | -2.95139 | 2.26608  | 55 | 0.027403 | 30      | 27      |
| CCNB1  | -4.44522 | -3.35763 | -2.25148 | 55 | 0.028370 | 30      | 27      |
| TRAIL  | 0.34893  | -0.56574 | 2.20372  | 55 | 0.031749 | 30      | 27      |
| EstR1  | 4.60346  | 3.60340  | 2.20223  | 55 | 0.031860 | 30      | 27      |
| DR5    | -5.71827 | -6.79088 | 2.14548  | 55 | 0.036345 | 30      | 27      |
| MCM2   | -2.96800 | -2.48458 | -2.10518 | 55 | 0.039857 | 30      | 27      |
| Chk1   | -3.46968 | -2.85708 | -2.08597 | 55 | 0.041633 | 30      | 27      |
| p27    | 0.94714  | 0.49656  | 2.04313  | 55 | 0.045843 | 30      | 27      |
| MYBL2  | -3.97810 | -3.14837 | -2.02921 | 55 | 0.047288 | 30      | 27      |
| GUS    | -1.42486 | -1.82900 | 1.99758  | 55 | 0.050718 | 30      | 27      |
| P53    | -1.08810 | -1.47193 | 1.92087  | 55 | 0.059938 | 30      | 27      |
| HIF1A  | -0.40925 | 0.11688  | -1.91278 | 55 | 0.060989 | 30      | 27      |
| cMet   | -6.36835 | -5.58479 | -1.88318 | 55 | 0.064969 | 30      | 27      |
| EGFR   | -2.95785 | -2.28105 | -1.86840 | 55 | 0.067036 | 30      | 27      |
| MTA1   | -7.55365 | -8.13656 | 1.81479  | 55 | 0.075011 | 30      | 27      |
| RIZ1   | -7.52785 | -8.25903 | 1.79518  | 55 | 0.078119 | 30      | 27      |
| ErbB3  | -6.62488 | -7.10826 | 1.79255  | 55 | 0.078545 | 30      | 27      |
| TOP2B  | 0.54974  | 0.27531  | 1.74888  | 55 | 0.085891 | 30      | 27      |
| EIF4E  | -5.06603 | -6.31426 | 1.68030  | 55 | 0.098571 | 30      | 27      |
| TS     | -2.95042 | -2.36167 | -1.67324 | 55 | 0.099959 | 30      | 27      |
| STK15  | -3.25010 | -2.72118 | -1.64822 | 55 | 0.105010 | 30      | 27      |

For each gene, a classification algorithm was utilized to identify the best threshold value (CT) for using each gene alone in predicting clinical outcome.

Based on the data set forth in Table 2, expression of the following genes in ER-positive cancer above a defined expression level is indicative of a reduced likelihood of survival without cancer recurrence following surgery: CD68; CTSL; FBXO5; SURV; CCNB1; MCM2; Chk1; MYBL2; HIF1A; cMET; EGFR; TS; STK15. Many of these genes (CD68, CTSL, SURV, CCNB1, MCM2, Chk1, MYBL2, EGFR, and STK15) were also identified as indicators of poor prognosis in the previous analysis, not limited to ER-positive breast cancer. Based on the data set forth in Table 2, expression of the following genes in ER-positive cancer above a defined expression level is indicative of a better prognosis for survival without cancer recurrence following surgery: IGFR1; BC12; HNF3A; TP53BP2; GATA3; BBC3; RAD51C; BAG1; IGFBP2; PR; CD9; RB1; EPHX1; CEGP1; TRAIL; DR5; p27; p53; MTA; RIZ1; ErbB3; TOP2B; EIF4E. Of the latter genes, IGFR1; BC12; TP53BP2; GATA3; BBC3; RAD51C; BAG1; IGFBP2; PR; CD9; CEGP1; DR5; p27; RIZ1; ErbB3; TOP2B; EIF4E have also been identified as indicators of good prognosis in the previous analysis, not limited to ER-positive breast cancer.

Analysis of ER Negative Patients by Binary Approach

Twenty patients with normalized CT for estrogen receptor (ER) <0 (i.e., ER negative patients) were subjected to separate analysis. A t test was performed on the two groups of patients classified as either no recurrence and no breast cancer related to death at three years, or recurrence or breast cancer-related death at three years, and the p-values for the differences between the groups for each gene were calculated. Table 3 lists the genes where the p-value for the differences between the groups was <.118. The first column of mean expression values pertains to patients who neither had a metastatic recurrence nor died from breast cancer. The second column of mean expression values pertains to patients who either had a metastatic recurrence of or died from breast cancer.

TABLE 3

|        | Mean     | Mean     | t-value  | df | p        | Valid N | Valid N |
|--------|----------|----------|----------|----|----------|---------|---------|
| KRT14  | -1.95323 | -6.69231 | 4.03303  | 18 | 0.000780 | 5       | 15      |
| KLK10  | -2.68043 | -7.11288 | 3.10321  | 18 | 0.006136 | 5       | 15      |
| CCND1  | -1.02285 | 0.03732  | -2.77992 | 18 | 0.012357 | 5       | 15      |
| Upa    | -0.91272 | -0.04773 | -2.49460 | 18 | 0.022560 | 5       | 15      |
| HNF3A  | -6.04780 | -2.36469 | -2.43148 | 18 | 0.025707 | 5       | 15      |
| Maspin | -3.56145 | -6.18678 | 2.40169  | 18 | 0.027332 | 5       | 15      |

TABLE 3-continued

|  | Mean | Mean | t-value | df | p | Valid N | Valid N |
|---|---|---|---|---|---|---|---|
| CDH1 | -3.54450 | -2.34984 | -2.38755 | 18 | 0.028136 | 5 | 15 |
| HER2 | -1.48973 | 1.53108 | -2.35826 | 18 | 0.029873 | 5 | 15 |
| GRB7 | -2.55289 | 0.00036 | -2.32890 | 18 | 0.031714 | 5 | 15 |
| AKT1 | -0.36849 | 0.46222 | -2.29737 | 18 | 0.033807 | 5 | 15 |
| TGFA | -4.03137 | -5.67225 | 2.28546 | 18 | 0.034632 | 5 | 15 |
| FRP1 | 1.45776 | -1.39459 | 2.27884 | 18 | 0.035097 | 5 | 15 |
| STMY3 | -1.59610 | -0.26305 | -2.23191 | 18 | 0.038570 | 5 | 15 |
| Contig 27882 | -4.27585 | -7.34338 | 2.18700 | 18 | 0.042187 | 5 | 15 |
| A-Catenin | -1.19790 | -0.39085 | -2.15624 | 18 | 0.044840 | 5 | 15 |
| VDR | -4.37823 | -2.37167 | -2.15620 | 18 | 0.044844 | 5 | 15 |
| GRO1 | -3.65034 | -5.97002 | 2.12286 | 18 | 0.047893 | 5 | 15 |
| MCM3 | -3.86041 | -5.55078 | 2.10030 | 18 | 0.050061 | 5 | 15 |
| B-actin | 4.69672 | 5.19190 | -2.04951 | 18 | 0.055273 | 5 | 15 |
| HIF1A | -0.64183 | -0.10566 | -2.02301 | 18 | 0.058183 | 5 | 15 |
| MMP9 | -8.90613 | -7.35163 | -1.88747 | 18 | 0.075329 | 5 | 15 |
| VEGF | 0.37904 | 1.10778 | -1.87451 | 18 | 0.077183 | 5 | 15 |
| PRAME | -4.95855 | -7.41973 | 1.86668 | 18 | 0.078322 | 5 | 15 |
| AIB1 | -3.12245 | -1.92934 | -1.86324 | 18 | 0.078829 | 5 | 15 |
| KRT5 | -1.32418 | -3.62027 | 1.85919 | 18 | 0.079428 | 5 | 15 |
| KRT18 | 1.08383 | 2.25369 | -1.83831 | 18 | 0.082577 | 5 | 15 |
| KRT17 | -0.69073 | -3.56536 | 1.78449 | 18 | 0.091209 | 5 | 15 |
| P14ARF | -1.87104 | -3.36534 | 1.63923 | 18 | 0.118525 | 5 | 15 |

Based on the data set forth in Table 3, expression of the following genes in ER-negative cancer above a defined expression level is indicative of a reduced likelihood of survival without cancer recurrence (p<0.05): CCND1; UPA; HNF3A; CDH1; Her2; GRB7; AKT1; STMY3; α-Catenin; VDR; GRO1. Only 2 of these genes (Her2 and Grb7) were also identified as indicators of poor prognosis in the previous analysis, not limited to ER-negative breast cancer. Based on the data set forth in Table 3, expression of the following genes in ER-negative cancer above a defined expression level is indicative of a better prognosis for survival without cancer recurrence (KT14; KLK10; Maspin, TGFα, and FRP1. Of the latter genes, only KLK10 has been identified as an indicator of good prognosis in the previous analysis, not limited to ER-negative breast cancer.

Analysis of Multiple Genes and Indicators of Outcome

Two approaches were taken in order to determine whether using multiple genes would provide better discrimination between outcomes.

First, a discrimination analysis was performed using a forward stepwise approach. Models were generated that classified outcome with greater discrimination than was obtained with any single gene alone.

According to a second approach (time-to-event approach), for each gene a Cox Proportional Hazards model (see, e.g. Cox, D. R., and Oakes, D. (1984), *Analysis of Survival Data*, Chapman and Hall, London, New York) was defined with time to recurrence or death as the dependent variable, and the expression level of the gene as the independent variable. The genes that have a p-value <0.10 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending on whether the gene is an indicator of bad (RR>1.01) or good (RR<1.01) prognosis. Thus, any threshold value will define subgroups of patients with respectively increased or decreased risk. The results are summarized in Table 4. The third column, with the heading: exp(coef), shows RR values.

TABLE 4

| Gene | coef | exp(coef) | se(coef) | z | p |
|---|---|---|---|---|---|
| TP53BP2 | -0.21892 | 0.803386 | 0.068279 | -3.20625 | 0.00134 |
| GRB7 | 0.235697 | 1.265791 | 0.073541 | 3.204992 | 0.00135 |
| PR | -0.10258 | 0.90251 | 0.035864 | -2.86018 | 0.00423 |
| CD68 | 0.465623 | 1.593006 | 0.167785 | 2.775115 | 0.00552 |
| Bcl2 | -0.26769 | 0.765146 | 0.100785 | -2.65603 | 0.00791 |
| KRT14 | -0.11892 | 0.887877 | 0.046938 | -2.53359 | 0.0113 |
| PRAME | -0.13707 | 0.871912 | 0.054904 | -2.49649 | 0.0125 |
| CTSL | 0.431499 | 1.539564 | 0.185237 | 2.329444 | 0.0198 |
| EstR1 | -0.07686 | 0.926018 | 0.034848 | -2.20561 | 0.0274 |
| Chk1 | 0.284466 | 1.329053 | 0.130823 | 2.174441 | 0.0297 |
| IGFBP2 | -0.2152 | 0.806376 | 0.099324 | -2.16669 | 0.0303 |
| HER2 | 0.155303 | 1.168011 | 0.072633 | 2.13818 | 0.0325 |
| BAG1 | -0.22695 | 0.796959 | 0.106377 | -2.13346 | 0.0329 |
| CEGP1 | -0.07879 | 0.924236 | 0.036959 | -2.13177 | 0.033 |
| STK15 | 0.27947 | 1.322428 | 0.132762 | 2.105039 | 0.0353 |
| KLK10 | -0.11028 | 0.895588 | 0.05245 | -2.10248 | 0.0355 |
| B.Catenin | -0.16536 | 0.847586 | 0.084796 | -1.95013 | 0.0512 |
| EstR1 | -0.0803 | 0.922842 | 0.042212 | -1.90226 | 0.0571 |
| GSTM1 | -0.13209 | 0.876266 | 0.072211 | -1.82915 | 0.0674 |
| TOP2A | -0.11148 | 0.894512 | 0.061855 | -1.80222 | 0.0715 |
| AlB1 | 0.152968 | 1.165288 | 0.086332 | 1.771861 | 0.0764 |
| FHIT | -0.15572 | 0.855802 | 0.088205 | -1.7654 | 0.0775 |
| RIZ1 | -0.17467 | 0.839736 | 0.099464 | -1.75609 | 0.0791 |
| SURV | 0.185784 | 1.204162 | 0.106625 | 1.742399 | 0.0814 |
| IGF1 | -0.10499 | 0.900338 | 0.060482 | -1.73581 | 0.0826 |
| BBC3 | -0.1344 | 0.874243 | 0.077613 | -1.73163 | 0.0833 |
| IGF1R | -0.13484 | 0.87358 | 0.077889 | -1.73115 | 0.0834 |
| DIABLO | 0.284336 | 1.32888 | 0.166556 | 1.707148 | 0.0878 |
| TBP | -0.34404 | 0.7089 | 0.20564 | -1.67303 | 0.0943 |
| p27 | -0.26002 | 0.771033 | 0.1564 | -1.66256 | 0.0964 |
| IRS1 | -0.07585 | 0.926957 | 0.046096 | -1.64542 | 0.0999 |

The binary and time-to-event analyses, with few exceptions, identified the same genes as prognostic markers. For example, comparison of Tables 1 and 4 shows that 10 genes were represented in the top 15 genes in both lists. Furthermore, when both analyses identified the same gene at [p<0.10], which happened for 21 genes, they were always concordant with respect to the direction (positive or negative sign) of the correlation with survival/recurrence. Overall, these results strengthen the conclusion that the identified markers have significant prognostic value.

For Cox models comprising more than two genes (multivariate models), stepwise entry of each individual gene into the model is performed, where the first gene entered is pre-selected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis is performed using the following equation:

$$RR = \exp[\mathrm{coef}(geneA) \times Ct(geneA) + \mathrm{coef}(geneB) \times Ct(geneB) + \mathrm{coef}(geneC) \times Ct(geneC) + \ldots].$$

In this equation, coefficients for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

Multivariate Gene Analysis of 79 Patients with Invasive Breast Carcinoma

A multivariate stepwise analysis, using the Cox Proportional Hazards Model, was performed on the gene expression data obtained for all 79 patients with invasive breast carcinoma. The following ten-gene sets have been identified by this analysis as having particularly strong predictive value of patient survival:

(a) TP53BP2, Bcl2, BAD, EPHX1, PDGFRβ, DIABLO, XIAP, YB1, CA9, and KRT8.
(b) GRB7, CD68, TOP2A, Bcl2, DIABLO, CD3, ID1, PPM1D, MCM6, and WISP1.
(c) PR, TP53BP2, PRAME, DIABLO, CTSL, IGFBP2, TIMP1, CA9, MMP9, and COX2.
(d) CD68, GRB7, TOP2A, Bcl2, DIABLO, CD3, ID1, PPM1D, MCM6, and WISP1.
(e) Bcl2, TP53BP2, BAD, EPHX1, PDGFRβ, DIABLO, XIAP, YB1, CA9, and KRT8.
(f) KRT14, KRT5, PRAME, TP53BP2, GUS1, AIB1, MCM3, CCNE1, MCM6, and ID1.
(g) PRAME, TP53BP2, EstR1, DIABLO, CTSL, PPM1D, GRB7, DAPK1, BBC3, and VEGFB.
(h) CTSL2, GRB7, TOP2A, CCNB1, Bcl2, DIABLO, PRAME, EMS1, CA9, and EpCAM.
(i) EstR1, TP53BP2, PRAME, DIABLO, CTSL, PPM1D, GRB7, DAPK1, BBC3, and VEGFB.
(k) Chk1, PRAME, p53BP2, GRB7, CA9, CTSL, CCNB1, TOP2A, tumor size, and IGFBP2.
(l) IGFBP2, GRB7, PRAME, DIABLO, CTSL, β-Catenin, PPM1D, Chk1, WISP1, and LOT1.
(m) HER2, TP53BP2, Bcl2, DIABLO, TIMP1, EPHX1, TOP2A, TRAIL, CA9, and AREG.
(n) BAG1, TP53BP2, PRAME, IL6, CCNB1, PAIL, AREG, tumor size, CA9, and Ki67.
(o) CEGP1, TP53BP2, PRAME, DIABLO, Bcl2, COX2, CCNE1, STK15, and AKT2, and FGF18.
(p) STK15, TP53BP2, PRAME, IL6, CCNE1, AKT2, DIABLO, cMet, CCNE2, and COX2.
(q) KLK10, EstR1, TP53BP2, PRAME, DIABLO, CTSL, PPM1D, GRB7, DAPK1, and BBC3.
(r) AIB1, TP53BP2, Bcl2, DIABLO, TIMP1, CD3, p53, CA9, GRB7, and EPHX1
(s) BBC3, GRB7, CD68, PRAME, TOP2A, CCNB1, EPHX1, CTSL GSTM1, and APC.
(t) CD9, GRB7, CD68, TOP2A, Bcl2, CCNB1, CD3, DIABLO, ID1, and PPM1D.
(w) EGFR, KRT14, GRB7, TOP2A, CCNB1, CTSL, Bcl2, TP, KLK10, and CA9.
(x) HIF1α, PR, DIABLO, PRAME, Chk1, AKT2, GRB7, CCNE1, TOP2A, and CCNB1.
(y) MDM2, TP53BP2, DIABLO, Bcl2, AIB1, TIMP1, CD3, p53, CA9, and HER2.
(z) MYBL2, TP53BP2, PRAME, IL6, Bcl2, DIABLO, CCNE1, EPHX1, TIMP1, and CA9.
(aa) p27, TP53BP2, PRAME, DIABLO, Bcl2, COX2, CCNE1, STK15, AKT2, and ID1.
(ab) RAD51, GRB7, CD68, TOP2A, CIAP2, CCNB1, BAG1, IL6, FGFR1, and TP53BP2.
(ac) SURV, GRB7, TOP2A, PRAME, CTSL, GSTM1, CCNB1, VDR, CA9, and CCNE2.
(ad) TOP2B, TP53BP2, DIABLO, Bcl2, TIMP1, AIB1, CA9, p53, KRT8, and BAD.
(ae) ZNF217, GRB7, p53BP2, PRAME, DIABLO, Bcl2, COX2, CCNE1, APC4, and β-Catenin.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the personalized prognosis of breast cancer, similar genes, gene sets and methods concerning other types of cancer are specifically within the scope herein.

All references cited throughout the disclosure are hereby expressly incorporated by reference.

TABLE 5A

| Gene | Accession | Seq | SEQ ID NO: |
|---|---|---|---|
| AIB1 | NM_006534 | GCGGCGAGTTTCCGATTTAAAGCTGAGCTGCGAGGAAAATGGCGGCGGGAGGATCAAAATACTTGCTGGATGGTGGACTCA | 1 |
| AKT1 | NM_005163 | CGCTTCTATGGCGCTGAGATTGTGTCAGCCCTGGACTACCTGCACTCGGAGAAGAACGTGGTGTACCGGGA | 2 |
| AKT2 | NM_001626 | TCCTGCCACCCTTCAAACCTCAGGTCACGTCCGAGGTCGACACAAGGTACTTCGATGATGAATTTACCGCC | 3 |
| APC | NM_000038 | GGACAGCAGGAATGTGTTTCTCCATACAGGTCACGGGGAGCCAATGGTTCAGAAACAAATCGAGTGGGT | 4 |

TABLE 5A-continued

| Gene | Accession | Seq | SEQ ID NO: |
|---|---|---|---|
| AREG | NM_001657 | TGTGAGTGAAATGCCTTCTAGTAGTGAACCGTCCTCGGGAGCCGACTATGACTACTCAGAAGAGTATGATPACGAACCACAA | 5 |
| B-actin | NM_001101 | CAGCAGATGTGGATCAGCAAGCAGGAGTATGACGAGTCCGGCCCCTCCATCGTCCACCGCAAATGC | 6 |
| B-Catenin | NM_001904 | GGCTCTTGTGCGTACTGTCCTTCGGGCTGGTGACAGGGAAGACATCACTGAGCCTGCCATCTGTGCTCTTCGTCATCTGA | 7 |
| BAD | NM_032989 | GGGTCAGGTGCCTCGAGATCGGGCTTGGGCCCAGAGCATGTTCCAGATCCCAGAGTTTGAGCCGAGTGAGCAG | 8 |
| BAG1 | NM_004323 | CGTTGTCAGCACTTGGAATACAAGATGGTTGCCGGGTCATGTTAATTGGGAAAAAGAACAGTCCACAGGAAGAGGTTGAAC | 9 |
| BBC3 | NM_014417 | CCTGGAGGGTCCTGTACAATCTCATCATGGGAGTCCTGCCCTTACCCAGGGGCCACAGAGCCCCCGAGATGGAGCCCAATTAG | 10 |
| Bcl2 | NM_000633 | CAGATGGACCTAGTACCCACTGAGATTTCCACGGCGAAGGACAGCGATGGGAAAAATGCCCTTAAATCATAGG | 11 |
| CA9 | NM_001216 | ATCCTAGCCCTGGTTTTTGGCCTCCTTTTTGCTGTCACCAGCGTCGCGTTCCTTGTGCAGAAAGGCAG | 12 |
| CCNB1 | NM_031966 | TTCAGGTTGTTGCAGGAGACCATGTACATGACTGTCTCCATTATTGATCGGTTCATGCAGAATAATTGTGTGCCCAAGAAGATG | 13 |
| CCND1 | NM_001758 | GCATGTTCGTGGCCTCTAAGATGAAGGAGACCATCCCCCTGACGGCCGAGAAGCTGTGCATCTACACCG | 14 |
| CCNE1 | NM_001238 | AAAGAAGATGATGACCGGGTTTACCCAAACTCAACGTGCAAGCCTCGGATTATTGCACCATCCAGAGGCTC | 15 |
| CCNE2 | NM_057749 | ATGCTGTGGCTCCTTCCTAACTGGGGCTTTCTTGACATGTAGGTTGCTTGGTAATAACCTTTTTGTATATCACAATTTGGGT | 16 |
| CD3z | NM_000734 | AGATGAAGTGGAAGGCGCTTTTCACCGCGGCCATCCTGCAGGCACAGTTGCCGATTACAGAGGCA | 17 |
| CD68 | NM_001251 | TGGTTCCCAGCCCTGTGTCCACCTCCAAGCCCAGATTCAGATTCGAGTCATGTACACAACCCAGGGTGGAGGAG | 18 |
| CD9 | NM_001769 | GGGCGTGGAACAGTTTATCTCAGACATCTGCCCCAAGAAGGACGTACTCGAAACCTTCACGTG | 19 |
| CDH1 | NM_004360 | TGAGTGTCCCCCGGTATCTTCCCCGCCCTGCCAATCCCGATGAAATTGGAAATTTTATTGATGAAAATCTGAAAGCGGCTG | 20 |
| CEGP1 | NM_020974 | TGACAATCAGCACACCTGCATTCACCGCTCGGAAGAGGGCCTGAGCTGCATGAATAAGGATCACGGCTGTAGTCACA | 21 |
| Chk1 | NM_001274 | GATAAATTGGTACAAGGGATCAGCTTTTCCCAGCCCACATGTCCTGATCATATGCTTTTGAATAGTCAGTTACTTGGCACCC | 22 |
| CIAP1 | NM_001166 | TGCCTGTGGTGGGAAGCTCAGTAACTGGGAACCAAAGGATGATGCTATGTCAGAACACCGGAGGCATTTTCC | 23 |
| cIAP2 | NM_001165 | GGATATTTCCGTGGCTCTTATTCAAACTCTCCATCAAATCCTGTAAACTCCAGAGCAAATCAAGATTTTTCTGCCTTGATGAGAAG | 24 |
| cMet | NM_000245 | GACATTTCCAGTCCTGCAGTCAATGCCTCTCTGCCCCACCCTTTGTTCAGTGTGGCTGGTGCCACGACAAATGTGTGCGATCGGAG | 25 |
| Contig 27882 | AK000618 | GGCATCCTGGCCCAAAGTTTCCCAAATCCAGGCGGCTAGAGGCCCACTGCTTCCCAACTACCAGCGAGGGGGTC | 26 |
| COX2 | NM_000963 | TCTGCAGAGTTGGAAGCACTCTATGGTGACATCGATGCTGTGGAGCTGTATCCTGCCCTTCTGGTAGAAAAGCCTCGGC | 27 |
| CTSL | NM_001912 | GGGAGGCTTATCTCACTGAGTGAGCAGAATCTGGTAGACTGCTCTGGGCCTCAAGGCAATGAAGGCTGCAATGG | 28 |
| CTSL2 | NM_001333 | TGTCTCACTGAGCGAGCAGAATCTGGTGGACTGTTCGCGTCCTCAAGGCAATCAGGGCTGCAATGGT | 29 |
| DAPK1 | NM_004938 | CGCTGACATCATGAATGTTCCTCGACCGGCTGGAGGCGAGTTTGGATATGACAAAGACACATCGTTGCTGAAAGAGA | 30 |
| DIABLO | NM_019887 | CACAATGGCGGCTCTGAAGAGTTGGCTGTCGCGCAGCGTAACTTCATTCTTCAGGTACAGACAGTGTTTGTGT | 31 |

TABLE 5B

| Gene | Accession | Seq | SEQ ID NO: |
|---|---|---|---|
| DR5 | NM_003842 | CTCTGAGACAGTGCTTCGATGACTTTGCAGACTTGGTGCCCTTTGACTCCTGGGAGCCGCTCATGAGGAAGTTGGGCCTCATGG | 32 |
| EGFR | NM_005228 | TGTCGATGGACTTCCAGAACCACCTGGGCAGCTGCCAAAAGTGTGATCCAAGCTGTCCCAAT | 33 |
| EIF4E | NM_001968 | GATCTAAGATGGCGACTGTCGAACCGGAAACCACCCCTACTCCTAATCCCCCGACTACAGAAGAGGAGAAAACGGAATCTAA | 34 |
| EMS1 | NM_005231 | GGCAGTGTCACTGAGTCCTTGAAATCCTCCCCTGCCCCGCGGGTCTCTGGATTGGGACGCACAGTGCA | 35 |
| EpCAM | NM_002354 | GGGCCCTCCAGAACAATGATGGGCTTTATGATCCTGACTGCGATGAGAGCGGGCTCTTTAAGGCCAAGCAGTGCA | 36 |
| EPHX1 | NM_000120 | ACCGTAGGCTCTGCTCTGAATGACTCTCCTGTGGGTCTGGCTGCCTATATTCTAGAGAAGTTTTCCACCTGGACCA | 37 |
| ErbB3 | NM_001982 | CGGTTATGTCATGCCAGATACACACCTCAAAGGTACTCCCTCCTCCCGGGAGGCACCCTTTCTTCAGTGGGTCTCAGTTC | 38 |
| EstR1 | NM_000125 | CGTGGTGCCCCTCTATGACCTGCTGCTGGAGATGCTGGACGCCCACCGCCTACATGCGCCCACTAGCC | 39 |
| FBXO5 | NM_012177 | GGCTATTCCTCATTTTCTCTACAAAGTGGCCTCAGTGAACATGAAGAAGGTAGCCTCCTGGAGGAGAATTTCGGTGACAGTCTAGAATCC | 40 |
| FGF18 | NM_003862 | CGGTAGTCAAGTCCGGATCAAGGGCAAGGAGACGGAATTCTACCTGTGCATGAACCGCAAAGGCAAGC | 41 |
| FGFR1 | NM_023109 | CACGGGACATTCACCACATCGACTACTATAAAAAGACAACCAACGGCCGACTGCCTGTGAAGTGGATGGCACCC | 42 |

TABLE 5B-continued

| Gene | Accession | Seq | SEQ ID NO: |
|---|---|---|---|
| FHIT | NM_002012 | CCAGTGGAGCGCTTCCATGACCTGCGTCCTGATGAAGTGGCCGATTTGTTTCAGACGACCCAGAGAG | 43 |
| FRP1 | NM_003012 | TTGGTACCTGTGGGTTAGCATCAAGTTCTCCCCAGGGTAGAATTCAATCAGAGCTCCAGTTTGCATTTG-GATGTG | 44 |
| G-Catenin | NM_002230 | TCAGCAGCAAGGGCATCATGGAGGAGGATGAGGCCTGCGGGCGCCAGTACACGCTCAAGAAAACCACC | 45 |
| GAPDH | NM_002046 | ATTCCACCCATGGCAAATTCCATGGCACCGTCAAGGCTGAGAACGGGAAGCTTGTCATCAATGGAAAT-CCCATC | 46 |
| GATA3 | NM_002051 | CAAAGGAGCTCACTGTGGTGTCTGTGTTCCAACCACTGAATCTGGACCCCATCTGTGAATAAGCCATTC-TGACTC | 47 |
| GRB7 | NM_005310 | CCATCTGCATCCATCTTGTTTGGGCTCCCCACCCTTGAGAAGTGCCTCAGATAATACCCTGGTGGCC | 48 |
| GRO1 | NM_001511 | CGAAAAGATGCTGAACAGTGACAAATCCAACTGACCAGAAGGGAGGAGGAAGCTCACTGGTGGCTGT-TCCTGA | 49 |
| GSTM1 | NM_000561 | AAGCTATGAGGAAAAGAAGTACACGATGGGGGACGCTCCTGATTATGACAGAAGCCAGTGGCTGAAT-GAAAAATTCAAGCTGGGCC | 50 |
| GUS | NM_000181 | CCCACTCAGTAGCCAAGTCACAATGTTTGGAAAACAGCCCGTTTACTTGAGCAAGACTGATACCACCT-GCGTG | 51 |
| HER2 | NM_004448 | CGGTGTGAGAAGTGCAGCAAGCCCTGTGCCCGAGTGTGCTATGGTCTGGGCATGGAGCACTTGCGAGA-GG | 52 |
| HIF1A | NM_001530 | TGAACATAAAGTCTGCAACATGGAAGGTATTGCACTGCACAGGCCACATTCACGTATATGATACCAAC-AGTAACCACCTCA | 53 |
| HNF3A | NM_004496 | TCCAGGATGTTAGGAACTGTGAAGATGGAAGGGCATGAAACCAGCGACTGGAACAGCTACTACGCAG-ACACGC | 54 |
| ID1 | NM_002165 | AGAACCGCAAGGTGAGCAAGGTGGAGATTCTCCAGCACGTCATCGACTACATCAGGGACCTTCAGTTG-GA | 55 |
| IGF1 | NM_000618 | TCCGGAGCTGTGATCTAAGGAGGCTGGAGATGTATTGCGCAGCCCTCAAGCCTGCCAAGTCAGCTCGC-TCTGTCCG | 56 |
| IGF1R | NM_000875 | GCATGGTAGCCGAAGATTTCACAGTCAAAATCGGAGATTTTGGTATGACGCGAGATATCTATGAGACA-GACTATTACCGGAAA | 57 |
| IGFBP2 | NM_000597 | GTGGACAGCACCATGAACATGTTGGGCGGGGGAGGCAGTGCTGGCCGGAAGCCCCTCAAGTCGGGTAT-GAAGG | 58 |
| IL6 | NM_000600 | CCTGAACCTTCCAAAGATGGCTGAAAAAGATGGATGCTTCCAATCTGGATTCAATGAGGAGACTTGCC-TGGT | 59 |
| IRS1 | NM_005544 | CCACAGCTCACCTTCTGTCAGGTGTCCATCCCAGCTCCAGCCAGCTCCCAGAGAGGAAGAGACTGGCA-CTGAGG | 60 |
| Ki-67 | NM_002417 | CGGACTTTGGGGTGCGACTTGACGAGCGGTGGTTCGACAAGTGGCCTTGCGGGCCGGATCGTCCCAGTG-GAAGAGTTGTAA | 61 |
| KLK10 | NM_002776 | GCCCAGAGGCTCCATCGTCCATCCTCTTCCTCCCCAGTCGGCTGAACTCTCCCCTTGTCTGCACTGTTCA-AACCTCTG | 62 |

TABLE 5C

| Gene | Accession | Seq | SEQ ID NO: |
|---|---|---|---|
| KRT14 | NM_000526 | GGCCTGCTGAGATCAAAGACTACAGTCCCTACTTCAAGACCATTGAGGACCTGAGGAACAAGATTCTC-ACAGCCACAGTGGAC | 63 |
| KRT17 | NM_000422 | CGAGGATTGGTTCTTGAGCAAGACAGAGGAACTGAACCGCGAGGTGGCCACCAACAGTGAGCTGGTGC-AGAGT | 64 |
| KRT18 | NM_000224 | AGAGATCGAGGCTCTCAAGGAGGAGCTGCTCTTCATGAAGAAGAACCACGAAGAGGAAGTAAAAGGCC | 65 |
| KRT19 | NM_002276 | TGAGCGGCAGAATCAGGAGTACCAGCGGCTCATGGACATCAAGTCGCGGCTGGAGCAGGAGATTGCC-ACCTACCGCA | 66 |
| KRT5 | NM_000424 | TCAGTGGAGAAGGAGTTGGACCAGTCAACATCTCTGTTGTCACAAGCAGTGTTTCCTCTGGATATGGCA | 67 |
| KRT8 | NM_002273 | GGATGAAGCTTACATGAACAAGGTAGAGCTGGAGTCTCGCCTGGAAGGGCTGACCGACGAGATCAACT-TCCTCAGGCAGCTATATG | 68 |
| LOT1 variant 1 | NM_002656 | GGAAAGACCACCTGAAAAACCACCTCCAGACCCACGACCCCAACAAAATGGCCTTTGGGTGTGAGGAG-TGTGGGAAGAAGTAG | 69 |
| Maspin | NM_002639 | CAGATGGCCACTTTGAGAACATTTGAGAACATTTTAGCTGACAACAGTGTGAACGACCAGACCAAAAT-CCTTGTGGTTAATGCTGCC | 70 |
| MCM2 | NM_004526 | GACTTTTGCCCGCTACCTTTCATTCCGGCGTGACAACAATGAGCTGTTGCTCTTCATACTGAAGCAGTT-ACTGGC | 71 |
| MCM3 | NM_002388 | GGAGAACAATCCCCTTGAGACAGAATATGGCCTTTCTGTCTACAAGGATCACCAGACCATCACCATCC-AGGAGAT | 72 |
| MCM6 | NM_005915 | TGATGGTCCTATGTGTCACATTCATCACAGGTTTCATACCAACACAGGCTTCAGCACTTCCTTTGGTGTG-TTTCCTGTCCCA | 73 |
| MDM2 | NM_002392 | CTACAGGGACAGCCATCAGAATCCGGATCTTGATGCTGGTGTAAGTGAACATTCAGGTGATTGGTTGG-AT | 74 |
| MMP9 | NM_004994 | GAGAACCAATCTCACCGACAGGCAGCTGGCAGAGGAATACCTGTACCGCTATGGTTACACTCGGGTG | 75 |
| MTA1 | NM_004689 | CCGCCCTCACCTGAAGAGAAACGCGCTCCTTGGCGGACACTGGGGAGGAGAGGAAGAAGCGCGGCT-AACTTATTCC | 76 |
| MYBL2 | NM_002466 | GCCGAGATCGCCAAGATGTTGCCAAGATGTTGCCAGGGAGGACAGACAATGCTGTGAAGAATCACTGG-AACTCTACCATCAAAAG | 77 |
| P14ARF | S78535 | CCCTCGTGCTGATGCTACTGAGGAGCCAGCGTCTAGGGCAGCAGCCGCTTCCTAGAAGACCAGGTCAT-GATG | 78 |

TABLE 5C-continued

| Gene | Accession | Seq | SEQ ID NO: |
|---|---|---|---|
| p27 | NM_004064 | CGGTGGACCACGAAGAGTTAACCCGGGACTTGGAGAAGCACTGCAGAGACATGGAAGAGGCGAGCC | 79 |
| P53 | NM_000546 | CTTTGAACCCTTGCTTGCAATAGGTGTGCGTCAGAAGCACCCAGGACTTCCATTTGCTTTGTCCCGGG | 80 |
| PAI1 | NM_000602 | CCGCAACGTGGTTTTCTCACCCTATGGGGTGGCCTCGGTGTTGGCCATGCTCCAGCTGACAACAGGAGG-AGAAACCCAGCA | 81 |
| PDGFRb | NM_002609 | CCAGCTCTCCTTCCAGCTACAGATCAATGTCCCTGTCCGAGTGCTGGAGCTAAGTGAGAGCCACCC | 82 |
| PI3KC2A | NM_002645 | ATACCAATCACCGCACAAACCCAGGCTATTTGTTAAGTCCAGTCACAGCGCAAAGAAACATATGCGGA-GAAAATGCTAGTGTG | 83 |
| PPM1D | NM_003620 | GCCATCCGCAAAGGCTTTCTCGCTTGTCACCTTGCCATGTGGAAGAAACTGGCGGAATGGCC | 84 |
| PR | NM_000926 | GCATCAGGCTGTCATTATGGTGTCCTTACCTGTGGGAGCTGTAAGGTCTTCTTTAAGAGGGCAATGGAA-GGGCAGCACAACTACT | 85 |
| PRAME | NM_006115 | TCTCCATATCTGCCTTGCAGAGTCTCCTGCAGCACCTCATCGGGCTGAGCAATCTGACCCACGTGC | 86 |
| pS2 | NM_003225 | GCCCTCCCAGTGTGCAAATAAGGGCTGCTGTTTCGACGACACCGTTCGTGGGGTCCCCTGGTGCTTCTA-TCCTAATACCATCGACG | 87 |
| RAD51C | NM_058216 | GAACTTCTTGAGCAGGAGCATACCCAGGCTTCATAATCACCTTCTGTTCAGCACTAGAGTGATATTCTT-GGGGGTGGA | 88 |
| RB1 | NM_000321 | CGAAGCCCTTACAAGTTTCCTAGTTCACCCTTACGGATTCCTGGAGGGAACATCTATATTTCACCCCTG-AAGAGTCC | 89 |
| RIZ1 | NM_012231 | CCAGACGAGCGATTAGAAGCGGCAGCTTGTGAGGTGAATGATTTGGGGGAAGAGGAGGAGGAGGAAG-AGGAGGA | 90 |
| STK15 | NM_003600 | CATCTTCCAGGAGGACCACTCTCTGTGGCACCCTGGACTACCTGCCCCCTGAAATGATTGAAGGTCGGA | 91 |
| STMY3 | NM_005940 | CCTGGAGGCTGCAACATACCTCAATCCTGTCCCAGGCCGGATCCTCCTGAAGCCCTTTTCGCAGCACTG-CTATCCTCCAAAGCCATTGTA | 92 |
| SURV | NM_001168 | TGTTTTGATTCCCGGGCTTACCAGGTGAGAAGTGAGGGAGGAAGAAGGCAGTGTCCCTTTTGCTAGAG-CTGACAGCTTTG | 93 |

TABLE 5D

| Gene | Accession | Seq | SEQ ID NO: |
|---|---|---|---|
| TBP | NM_003194 | GCCCGAAACGCCGAATATAATCCCAAGCGGTTTGCTGCGGTAATCATGAGGATAAGAGACCACG | 94 |
| TGFA | NM_003236 | GGTGTGCCACAGACCTTCCTACTTGGCCTGTAATCACCTGTGCAGCCTTTTGTGGGCCTTCAAAACTCT-GTCAAGAACTCCGT | 95 |
| TIMP1 | NM_003254 | TCCCTGCGGTCCCAGATAGCCTGAATCCTGCCCGGAGTGGAACTGAAGCCTGCACAGTGTCCACCCTGT-TCCCAC | 96 |
| TOP2A | NM_001067 | AATCCAAGGGGGAGAGTGATGACTTCCATATGGACTTTGACTCAGCTGTGGCTCCTCGGGCAAAATCT-GTAC | 97 |
| TOP2B | NM_001068 | TGTGGACATCTTCCCCTCAGACTTCCCTACTGAGCCACCTTCTCTGCCACGAACCGGTCGGGCTAG | 98 |
| TP | NM_001953 | CTATATGCAGCCAGAGATGTGACAGCCACCGTGGACAGCCTGCCACTCATCACAGCCTCCATTCTCAGT-AAGAAACTCGTGG | 99 |
| TP53BP2 | NM_005426 | GGGCCAAATATTCAGAAGCTTTTATATCAGAGGACCACCATAGCGGCCATGGAGACCATCTCTGTCCC-ATCATACCCATCC | 100 |
| TRAIL | NM_003810 | CTTCACAGTGCTCCTGCAGTCTCTCTGTGTGGCTGTAACTTACGTGTACTTTACCAACGAGCTGAAGCA-GAGATG | 101 |
| TS | NM_001071 | GCCTCGGTGTGCCTTTCAACATCGCCAGCTACGCCCTGCTCACGTACATGATTGCGCACATCACG | 102 |
| upa | NM_002658 | GTGGATGTGCCCTGAAGGACAAGCCAGGCGTCTACACGAGAGTCTCACACTTCTTACCCTGGATCCGC-AG | 103 |
| VDR | NM_000376 | GCCCTGGATTTCAGAAAGAGCCAAGTCTGGATCTGGGACCCTTTCCTTCCTTCCCTGGCTTGTAACT | 104 |
| VEGF | NM_003376 | CTGCTGTCTTGGGTGCATTGGAGCCTTGCCTTGCTGCTCTACCTCCACCATGCCAAGTGGTCCCAGGCT-GC | 105 |
| VEGFB | NM_003377 | TGACGATGGCCTGGAGTGTGTGCCCACTGGGCAGCACCAAGTCCGGATGCAGATCCTCATGATCCGGT-ACC | 106 |
| WISP1 | NM_003882 | AGAGGCATCCATGAACTTCACACTTGCGGGCTGCATCAGCACACGCTCCTATCAACCCAAGTACTGTGG-AGTTTG | 107 |
| XIAP | NM_001167 | GCAGTTGGAAGACACAGGAAAGTATCCCCAAATTGCAGATTTATCAACGGCTTTTATCTTGAAAATAGT-GCCACGCA | 108 |
| YB-1 | NM_004559 | AGACTGTGGAGTTTGATGTTGTTGAAGGAGAAAAGGGTGCGGAGGCAGCAAATGTTACAGGTCCTGGT-GGTGTTCC | 109 |
| ZNF217 | NM_006526 | ACCCAGTAGCAAGGAGAAGCCCACTCACTGCTCCGAGTGCGGCAAAGCTTCAGAACCTACCACCAGC-TG | 110 |

TABLE 6A

| Gene | Accession | Probe Name | Seq | Length | SEQ ID NO: |
|---|---|---|---|---|---|
| AIB1 | NM_005534 | S1994/A1B1.f3 | GCGGCGAGTTTCCGATTTA | 19 | 111 |
| AIB1 | NM_006534 | S1995/AIB1.r3 | TGAGTCCACCATCCAGCAAGT | 21 | 112 |
| AIB1 | NM_006534 | S5055/AIB1.p3 | ATGGCGGCGGGAGGATCAAAA | 21 | 113 |
| AKT1 | NM_005163 | S0010/AKT1.f3 | CGCTTCTATGGCGCTGAGAT | 20 | 114 |
| AKT1 | NM_005163 | S0012/AKT1.r3 | TCCCGGTACACCACGTTCTT | 20 | 115 |

TABLE 6A-continued

| Gene | Accession | Probe Name | Seq | Length | SEQ ID NO: |
|---|---|---|---|---|---|
| AKT1 | NM_005163 | S4776/AKT1.p3 | CAGCCCTGGACTACCTGCACTCGG | 24 | 116 |
| AKT2 | NM_001626 | S0828/AKT2.f3 | TCCTGCCACCCTTCAAACC | 19 | 117 |
| AKT2 | NM_001626 | S0829/AKT2.r3 | GGCGGTAAATTCATCATCGAA | 21 | 118 |
| AKT2 | NM_001626 | S4727/AKT2.p3 | CAGGTCACGTCCGAGGTCGACACA | 24 | 119 |
| APC | NM_000038 | S0022/APC.f4 | GGACAGCAGGAATGTGTTTC | 20 | 120 |
| APC | NM_000038 | S0024/APC.r4 | ACCCACTCGATTTGTTTCTG | 20 | 121 |
| APC | NM_000038 | S4888/APC.p4 | CATTGGCTCCCCGTGACCTGTA | 22 | 122 |
| AREG | NM_001657 | S0025/AREG.f2 | TGTGAGTGAAATGCCTTCTAGTAGTGA | 27 | 123 |
| AREG | NM_001657 | S0027/AREG.r2 | TTGTGGTTCGTTATCATACTCTTCTGA | 27 | 125 |
| AREG | NM_001657 | S4889/AREG.p2 | CCGTCCTCGGGAGCCGACTATGA | 23 | 124 |
| B-actin | NM_001101 | S0034/B-acti.f2 | CAGCAGATGTGGATCAGCAAG | 21 | 126 |
| B-actin | NM_001101 | S0036/B-acti.r2 | GCATTTGCGGTGGACGAT | 18 | 127 |
| B-actin | NM_001101 | S4730/B-acti.p2 | AGGAGTATGACAGTCCGGCCCC | 23 | 128 |
| B-Catenin | NM_001904 | S2150/B-Cate.f3 | GGCTCTTGTGCGTACTGTCCTT | 22 | 129 |
| B-Catenin | NM_001904 | S2151/B-Cate.r3 | TCAGATGACGAAGAGCACAGATG | 23 | 130 |
| B-Catenin | NM_001904 | S5046/B-Cate.p3 | AGGCTCAGTGATGTCTTCCCTGTCACCAG | 29 | 131 |
| BAD | NM_032989 | S2011/BAD.f1 | GGGTCAGGTGCCTCGAGAT | 19 | 132 |
| BAD | NM_032989 | S2012/BAD.r1 | CTGCTCACTCGGCTCAAACTC | 21 | 133 |
| BAD | NM_032989 | S5058/BAD.p1 | TGGGCCCAGAGCATGTTCCCAGATC | 24 | 134 |
| BAG1 | NM_004323 | S1386/BAG1.f2 | CGTTGTCAGCACTTGGAATACAA | 23 | 135 |
| BAG1 | NM_004323 | S1387/BAG1.r2 | GTTCAACCTCTTCCTGTGGACTGT | 24 | 135 |
| BAG1 | NM_004323 | S4731/BAG1.p2 | CCCAATTAACATGACCCGGCAACCAT | 26 | 137 |
| BBC3 | NM_014417 | S1584/BBC3.f2 | CCTGGAGGGTCCTGTACAAT | 20 | 138 |
| BBC3 | NM_014417 | S1585/BBC3.r2 | CTAATTGGGCTCCATCTCG | 19 | 139 |
| BBC3 | NM_014417 | S4890/BBC3.p2 | CATCATGGGACTCCTGCCCTTACC | 24 | 140 |
| Bcl2 | NM_000633 | S0043/Bcl2.f2 | CAGATGGACCTAGTACCCACTGAGA | 25 | 141 |
| Bcl2 | NM_000633 | S0045/Bcl2.r2 | CCTATGATTTAAGGGCATTTTTCC | 24 | 143 |
| Bcl2 | NM_000633 | S4732/Bcl2.p2 | TTCCACGCCGAAGGACAGCGAT | 22 | 142 |
| CA9 | NM_001216 | S1398/CA9.f3 | ATCCTAGCCCTGGTTTTTGG | 20 | 144 |
| CA9 | NM_001216 | S1399/CA9.r3 | CTGCCTTCTCATCTGCACAA | 20 | 145 |
| CA9 | NM_001216 | S4938/CA9.p3 | TTTGCTGTCACCAGCGTCGC | 20 | 146 |
| CCNB1 | NM_031966 | S1720/CCNB1.f2 | TTCAGGTTGTTGCAGGAGAC | 20 | 147 |
| CCNB1 | NM_031966 | S1721/CCNB1.r2 | CATCTTCTTGGGCACACAAT | 20 | 148 |
| CCNB1 | NM_031966 | S4733/CCNB1.p2 | TGTCTCCATTATTGATCGGTTCATGCA | 27 | 149 |
| CCND1 | NM_001758 | S0058/CCND1.f3 | GCATGTTCGTGGCCTTAAGA | 21 | 150 |
| CCND1 | NM_001758 | S0060/CCND1.r3 | CGGTGTAGATGCACAGCTTCTC | 22 | 151 |
| CCND1 | NM_001758 | S4986/CCND1.p3 | AAGGAGACCATCCCCCTGACGGC | 23 | 152 |
| CCNE1 | NM_001238 | S1446/CCNE1.f1 | AAAGAAGATGATGACCGGGTTTAC | 24 | 153 |
| CCNE1 | NM_001238 | S1447/CCNE1.r1 | GAGCCTCTGGATGGTGCAAT | 20 | 154 |
| CCNE1 | NM_001238 | S4944/CCNE1.p1 | CAACTCAACGTGCAAGCCTCGGA | 24 | 155 |

TABLE 6B

| Gene | Accession | Probe Name | Seq | Length | SEQ ID NO: |
|---|---|---|---|---|---|
| CCNE2 | NM_057749 | S1458/CCNE2.f2 | ATGCTGTGGCTCCTTCCTAACT | 22 | 156 |
| CCNE2 | NM_057749 | S1459/CCNE2.r2 | ACCCAAATTGTGATATACAAAAAGGTT | 27 | 157 |
| CCNE2 | NM_057749 | S4945/CCNE2.p2 | TACCAAGCAACCTACATGTCAAGAAAGCCC | 30 | 158 |
| CD3z | NM_000734 | S0064/CD3z.f1 | AGATGAAGTGGAAGGCGCTT | 20 | 159 |
| CD3z | NM_000734 | S0066/CD3z.r1 | TGCCTCTGTAATCGGCAACTG | 21 | 161 |
| CD3z | NM_000734 | S4988/CD3z.p1 | CACCGCGGCCATCCTGCA | 18 | 160 |
| CD68 | NM_001251 | S0067/CD68.f2 | TGGTTCCCAGCCCTGTGT | 18 | 162 |
| CD68 | NM_001251 | S0069/CD68.r2 | CTCCTCCACCCTGGGTTGT | 19 | 164 |
| CD68 | NM_001251 | S4734/CD68.p2 | CTCCAAGCCCAGATTCAGATTCGAGTCA | 28 | 163 |
| CD9 | NM_001769 | S0686/CD9.f1 | GGGCGTGGAACAGTTTATCT | 20 | 165 |
| CD9 | NM_001769 | S0687/CD9.r1 | CACGGTGAAGGTTTCGAGT | 19 | 166 |
| CD9 | NM_001769 | S4792/CD9.p1 | AGACATCTGCCCCAAGAAGGACGT | 24 | 167 |
| CDH1 | NM_004360 | S0073/CDH1.f3 | TGAGTGTCCCCCGGTATCTTC | 21 | 168 |
| CDH1 | NM_004360 | S0075/CDH1.r3 | CAGCCGCTTTCAGATTTTCAT | 21 | 169 |
| CDH1 | NM_004360 | S4990/CDH1.p3 | TGCCAATCCCGATGAAATTGGAAATTT | 27 | 170 |
| CEGP1 | NM_020974 | S1494/CEGP1.f2 | TGACAATCAGCACACCTGCAT | 21 | 171 |
| CEGP1 | NM_020974 | S1495/CEGP1.r2 | TGTGACTACAGCCGTGATCCTTA | 23 | 172 |
| CEGP1 | NM_020974 | S4735/CEGP1.p2 | CAGGCCCTCTTCCGAGCGGT | 20 | 173 |
| Chk1 | NM_001274 | S1422/Chk1.f2 | GATAAATTGGTACAAGGGATCAGCTT | 26 | 174 |
| Chk1 | NM_001274 | S1423/Chk1.r2 | GGGTGCCAAGTAACTGACTATTCA | 24 | 175 |
| Chk1 | NM_001274 | S4941/Chk1.p2 | CCAGCCCACATGTCCTGATCATATGC | 26 | 176 |
| CIAP1 | NM_001166 | S0764/CIAP1.f2 | TGCCTGTGGTGGGAAGCT | 18 | 177 |
| CIAP1 | NM_001166 | S0765/CIAP1.r2 | GGAAAATGCCTCCGGTGTT | 19 | 178 |
| CIAP1 | NM_001166 | S4802/CIAP1.p2 | TGACATAGCATCATCCTTTGGTTCCCAGTT | 30 | 179 |
| cIAP2 | NM_001165 | S0076/cIAP2.f2 | GGATATTTCCGTGGCTCTTATTCA | 24 | 180 |
| cIAP2 | NM_001165 | S0078/cIAP2.r2 | CTTCTCATCAAGGCAGAAAAATCTT | 25 | 182 |
| cIAP2 | NM_001165 | S4991/cIAP2.p2 | TCTCCATCAAATCCTGTAAACTCCAGCA | 30 | 181 |

TABLE 6B-continued

| Gene | Accession | Probe Name | Seq | Length | SEQ ID NO: |
|---|---|---|---|---|---|
| cMet | NM_000245 | S0082/cMet.f2 | GACATTTCCAGTCCTGCAGTCA | 22 | 183 |
| cMet | NM_000245 | S0084/cMet.r2 | CTCCGATCGCACACATTTGT | 20 | 185 |
| cMet | NM_000245 | S4993/cMet.p2 | TGCCTCTCTGCCCCACCCTTTGT | 23 | 184 |
| Contig 27882 | AK000618 | S2633/Contig.f3 | GGCATCCTGGCCCAAAGT | 18 | 186 |
| Contig 27882 | AK000618 | S2634/Contig.r3 | GACCCCCTCAGCTGGTAGTTG | 21 | 187 |
| Contig 27882 | AK000618 | S4977/Contig.p3 | CCCAAATCCAGGCGGCTAGAGGC | 23 | 188 |
| COX2 | NM_000963 | S0088/COX2.f1 | TCTGCAGAGTTGGAAGCACTCTA | 23 | 189 |
| COX2 | NM_000963 | S0090/COX2.r1 | GCCGAGGCTTTTCTACCAGAA | 21 | 191 |
| COX2 | NM_000963 | S4995/COX2.p1 | CAGGATACAGCTCCACAGCATCGATGTC | 28 | 190 |
| CTSL | NM_001912 | S1303/CTSL.f2 | GGGAGGCTTATCTCACTGAGTGA | 23 | 192 |
| CTSL | NM_001912 | S1304/CTSL.r2 | CCATTGCAGCCTTCATTGC | 19 | 193 |
| CTSL | NM_001912 | S4899/CTSL.p2 | TTGAGGCCCAGAGCAGTCTACCAGATTCT | 29 | 194 |
| CTSL2 | NM_001333 | S4354/CTSL2.f1 | TGTCTCACTGAGCGAGCAGAA | 21 | 195 |
| CTSL2 | NM_001333 | S4355/CTSL2.r1 | ACCATTGCAGCCCTGATTG | 19 | 196 |
| CTSL2 | NM_001333 | S4356/CTSL2.p1 | CTTGAGGACGCGAACAGTCCACCA | 24 | 197 |

TABLE 6O

| Gene | Accession | Probe Name | Seq | Length | SEQ ID NO: |
|---|---|---|---|---|---|
| DAPK1 | NM_004938 | S1768/DAPK1.f3 | CGCTGACATCATGAATGTTCCT | 22 | 198 |
| DAPK1 | NM_004938 | S1769/DAPK1.r3 | TCTCTTTCAGCAACGATCTCTCTT | 24 | 199 |
| DAPK1 | NM_004938 | S4927/DAPK1.p3 | TCATATCCAAACTGCCTCCAGCCG | 25 | 200 |
| DIABLO | NM_019887 | S0808/DIABLO.f1 | CACAATGGCGGCTCTGAAG | 19 | 201 |
| DIABLO | NM_019887 | S0809/DIABLO.r1 | ACACAAACACTGTCTGTACCTGAAGA | 26 | 202 |
| DIABLO | NM_019887 | S4813/DIABLO.p1 | AAGTTACGCTGCGCGACAGCCAA | 23 | 203 |
| DR5 | NM_003842 | S2551/DR5.f2 | CTCTGAGACAGTGCTTCGATGACT | 24 | 204 |
| DR5 | NM_003842 | S2552/DR5.r2 | CCATGAGGCCCAACTTCCT | 19 | 205 |
| DR5 | NM_003842 | S4979/DR5.p2 | CAGACTTGGTGCCCTTTGACTCC | 23 | 208 |
| EGFR | NM_005228 | S0103/EGFR.f2 | TGTCGATGGACTTCCAGAAC | 20 | 207 |
| EGFR | NM_005228 | S0105/EGFR.r2 | ATTGGGACAGCTTGGATCA | 19 | 209 |
| EGFR | NM_005228 | S4999/EGFR.p2 | CACCTGGGCAGCTGCCAA | 18 | 208 |
| EIF4E | NM_001968 | S0106/EIF4E.f1 | GATCTAAGATGGCGACTGTCGAA | 23 | 210 |
| EIF4E | NM_001968 | S0108/EIF4E.r1 | TTAGATTCCGTTTTCTCCTCTTCTG | 25 | 211 |
| EIF4E | NM_001968 | S5000/EIF4E.p1 | ACCACCCCTACTCCTAATCCCCCGACT | 27 | 212 |
| EMS1 | NM_005231 | S2663/EMS1.f1 | GGCAGTGTCACTGAGTCCTTGA | 22 | 213 |
| EMS1 | NM_005231 | S2664/EMS1.r1 | TGCACTGTGCGTCCCAAT | 18 | 214 |
| EMS1 | NM_005231 | S4956/EMS1.p1 | ATCCTCCCCTGCCCCGCG | 18 | 215 |
| EpCAM | NM_002354 | S1807/EpCAM.f1 | GGGCCCTCCAGAACAATGAT | 20 | 216 |
| EpCAM | NM_002354 | S1808/EpCAM.r1 | TGCACTGCTTGGCCTTAAAGA | 21 | 217 |
| EpCAM | NM_002354 | S4984/EpCAM.p1 | CCGCTCTCATCGCAGTCAGGATCAT | 25 | 218 |
| EPHX1 | NM_000120 | S1865/EPHX1.f2 | ACCGTAGGCTCTGCTCTGAA | 20 | 219 |
| EPHX1 | NM_000120 | S1866/EPHX1.r2 | TCCTGGAGGTGGAAAACTTC | 20 | 220 |
| EPHX1 | NM_000120 | S4754/EPHX1.p2 | AGGCAGCCAGACCCACAGGA | 20 | 221 |
| ErbB3 | NM_001982 | S0112/ErbB3.f1 | CGGTTATGTCATGCCAGATACAC | 23 | 222 |
| ErbB3 | NM_001982 | S0114/ErbB3.r1 | GAACTGAGACCCACTGAAGAAAGG | 24 | 224 |
| ErbB3 | NM_001982 | S5002/ErbB3.p1 | CCTCAAAGGTACTCCCTCCTCCCGG | 25 | 223 |
| EstR1 | NM_000125 | S0115/EstR1.f1 | CGTGGTGCCCCTCTATGAC | 19 | 225 |
| EstR1 | NM_000125 | S0117/EstR1.r1 | GGCTAGTGGGCGCATGTAG | 19 | 227 |
| EstR1 | NM_000125 | S4737/EstR1.p1 | CTGGAGATGCTGGACGCC | 19 | 226 |
| FBXO5 | NM_012177 | S2017/FBXO5.r1 | GGATTGTAGACTGTCACCGAAATTC | 25 | 228 |
| FBXO5 | NM_012177 | S2018/FBXO5.f1 | GGCTATTCCTCATTTTCTCTACAAAGTG | 28 | 229 |
| FBXO5 | NM_012177 | S5061/FBXO5.p1 | CCTCCAGGAGGCTACCTTCTTCATGTTCAC | 30 | 230 |
| FGF18 | NM_003862 | S1665/FGF18.f2 | CGGTAGTCAAGTCCGGATCAA | 21 | 231 |
| FGF18 | NM_003862 | S1666/FGF18.r2 | GCTTGCCTTTGCGGTTCA | 18 | 232 |
| FGF18 | NM_003862 | S4914/FGF18.p2 | CAAGGAGACGGAATTCTACCTGTGC | 25 | 233 |
| FGFR1 | NM_023109 | S0818/FGFR1.f3 | CACGGGACATTCACCACATC | 20 | 234 |
| FGFR1 | NM_023109 | S0819/FGFR1.r3 | GGGTGCCATCCACTTCACA | 19 | 235 |
| FGFR1 | NM_023109 | S4816/FGFR1.p3 | ATAAAAAGACAACCAACGGCCGACTGC | 27 | 236 |
| FHIT | NM_002012 | S2443/FHIT.f1 | CCAGTGGAGCGCTTCCAT | 18 | 237 |
| FHIT | NM_002012 | S2444/FHIT.r1 | CTCTCTGGGTCGTCTGAAACAA | 22 | 238 |
| FHIT | NM_002012 | S2445/FHIT.p1 | TCGGCCACTTCATCAGGACGCAG | 23 | 239 |
| FHIT | NM_002012 | S4921/FHIT.p1 | TCGGCCACTTCATCAGGACGCAG | 23 | 239 |
| FRP1 | NM_003012 | S1804/FRP1.f3 | TTGGTACCTGTGGGTTAGCA | 20 | 240 |
| FRP1 | NM_003012 | S1805/FRP1.r3 | CACATCCAAATGCAAACTGG | 20 | 241 |

TABLE 6D

| Gene | Accession | Probe Name | Seq | Length | SEQ ID NO: |
|---|---|---|---|---|---|
| FRP1 | NM_003012 | S4983/FRP1.p3 | TCCCCAGGGTAGAATTCAATCAGAGC | 26 | 242 |
| G-Catenin | NM_002230 | S2153/G-Cate.f1 | TCAGCAGCAAGGGCATCAT | 19 | 243 |
| G-Catenin | NM_002230 | S2154/G-Cate.r1 | GGTGGTTTTCTTGAGCGTGTACT | 23 | 244 |
| G-Catenin | NM_002230 | S5044/G-Cate.p1 | CGCCCGCAGGCCTCATCCT | 19 | 245 |
| GAPDH | NM_002046 | S0374/GAPDH.f1 | ATTCCACCCATGGCAAATTC | 20 | 246 |
| GAPDH | NM_002046 | S0375/GAPDH.r1 | GATGGGATTTCCATTGATGACA | 22 | 247 |
| GAPDH | NM_002046 | s4738/GAPDH.p1 | CCGTTCTCAGCCTTGACGGTGC | 22 | 248 |
| GATA3 | NM_002051 | S0127/GATA3.f3 | CAAAGGAGCTCACTGTGGTGTCT | 23 | 249 |
| GATA3 | NM_002051 | S0129/GATA3.r3 | GAGTCAGAATGGCTTATTCACAGATG | 26 | 251 |
| GATA3 | NM_002051 | S5005/GATA3.p3 | TGTTCCAACCACTGAATCTGGACC | 24 | 250 |
| GRB7 | NM_005310 | S0130/GRB7.f2 | CCATCTGCATCCATCTTGTT | 20 | 252 |
| GRB7 | NM_005310 | S0132/GR87.r2 | GGCCACCAGGGTATTATCTG | 20 | 254 |
| GRB7 | NM_005310 | S4726/GRB7.p2 | CTCCCCACCCTTGAGAAGTGCCT | 23 | 253 |
| GR01 | NM_001511 | S0133/GRO1.f2 | CGAAAAGATGCTGAACAGTGACA | 23 | 255 |
| GRO1 | NM_001511 | S0135/GRO1.r2 | TCAGGAACAGCCACCAGTGA | 20 | 256 |
| GRO1 | NM_001511 | S5006/GRO1.p2 | CTTCCTCCTCCCTTCTGGTCAGTTGGAT | 28 | 257 |
| GSTM1 | NM_000561 | S2026/GSTM1.r1 | GGCCCAGCTTGAATTTTTCA | 20 | 258 |
| GSTM1 | NM_000561 | S2027/GSTM1.f1 | AAGCTATGAGGAAAAGAAGTACACGAT | 27 | 259 |
| GSTM1 | NM_000561 | S4739/GSTM1.p1 | TCAGCCACTGGCTTCTGTCATAATCAGGAG | 30 | 260 |
| Gus | NM_000181 | S0139/GUS.f1 | CCCACTCAGTAGCCAACTCA | 20 | 261 |
| GUS | NM_000181 | S0141/GUS.r1 | CACGCAGGTGGTATCAGTCT | 20 | 263 |
| GUS | NM_000181 | S4740/GUS.p1 | TCAAGTAAACGGGCTGTTTTCCAAACA | 27 | 262 |
| HER2 | NM_004448 | S0142/HER2.f3 | CGGTGTGAGAAGTGCAGCAA | 20 | 264 |
| HER2 | NM_004448 | S0144/HER2.r3 | CCTCTCGCAAGTGCTCCAT | 19 | 266 |
| HER2 | NM_004448 | S4729/HER2.p3 | CCAGACCATAGCACACTCGGGCAC | 24 | 265 |
| HIF1A | NM_001530 | S1207/HIF1A.f3 | TGAACATAAAGTCTGCAACATGGA | 24 | 267 |
| HIF1A | NM_001530 | S1208/HIF1A.r3 | TGAGGTTGGTTACTGTTGGTATCATATA | 28 | 268 |
| HIF1A | NM_001530 | S4753/HIF1A.p3 | TTGCACTGCACAGGCCACATTCAC | 24 | 269 |
| HNF3A | NM_004496 | S0148/HNF3A.f1 | TCCAGGATGTTAGGAACTGTGAAG | 24 | 270 |
| HNF3A | NM_004496 | S0150/HNF3A.r1 | GCGTGTCTGCTAGTAGCTGTT | 22 | 271 |
| HNF3A | NM_004496 | S5008/HNF3A.p1 | AGTCGCTGGTTTCATGCCCTTCCA | 24 | 272 |
| ID1 | NM_002165 | S0820/ID1.f1 | AGAACCGCAAGGTGAGCAA | 19 | 273 |
| ID1 | NM_002165 | S0821/ID1.r1 | TCCAACTGAAGGTCCCTGATG | 21 | 274 |
| ID1 | NM_002165 | S4832/ID1.p1 | TGGAGATTCTCCAGCACGTCATCGAC | 26 | 275 |
| IGF1 | NM_000618 | S0154/IGF1.f2 | TCCGGAGCTGTGATCTAAGGA | 21 | 276 |
| IGF1 | NM_000618 | S0156/IGF1.r2 | CGGACAGAGCGAGCTGACTT | 20 | 278 |
| IGF1 | NM_000618 | S5010/IGF1.p2 | TGTATTGCGCACCCCTCAAGCCTG | 24 | 277 |
| IGF1R | NM_000875 | S1249/IGF1R.f3 | GCATGGTAGCCGAAGATTTCA | 21 | 279 |
| IGF1R | NM_000875 | S1250/IGF1R.r3 | TTTCCGGTAATAGTCTGTCTCATAGATATC | 30 | 280 |
| IGF1R | NM_000875 | S4895/IGF1R.p3 | CGCGTCATACCAAAATCTCCGATTTTGA | 28 | 281 |
| IGFBP2 | NM_000597 | S1128/IGFBP2.f1 | GTGGACAGCACCATGAACA | 19 | 282 |
| IGFBP2 | NM_000597 | S1129/IGFBP2.r1 | CCTTCATACCCGACTTGAGG | 20 | 283 |
| IGFBP2 | NM_000597 | S4837/IGFBP2.p1 | CTTCCGGCCAGCACTGCCTC | 20 | 284 |
| IL6 | NM_000600 | S0760/IL6.f3 | CCTGAACCTTCCAAAGATGG | 20 | 285 |

TABLE 6E

| Gene | Accession | Probe Name | Seq | Length | SEQ ID NO: |
|---|---|---|---|---|---|
| IL6 | NM_000600 | S0761/IL6.r3 | ACCAGGCAAGTCTCCTCATT | 20 | 286 |
| IL6 | NM_000600 | S4800/IL6.p3 | CCAGATTGGAAGCATCCATCTTTTTCA | 27 | 287 |
| IRS1 | NM_005544 | S1943/IRS1.f3 | CCACAGCTCACCTTCTGTCA | 20 | 288 |
| IRS1 | NM_005544 | S1944/IRS1.r3 | CCTCAGTGCCAGTCTCTTCC | 20 | 289 |
| IRS1 | NM_005544 | S5050/IRS1.p3 | TCCATCCCAGCTCCAGCCAG | 20 | 290 |
| Ki-67 | NM_002417 | S0436/Ki-67.f2 | CGGACTTTGGGTGCGACTT | 19 | 292 |
| Ki-67 | NM_002417 | S0437/Ki-67.r2 | TTACAACTCTTCCACTGGGACGAT | 24 | 293 |
| Ki-67 | NM_002417 | S4741/Ki-67.p2 | CCACTTGTCGAACCACCGCTCGT | 23 | 291 |
| KLK10 | NM_002776 | S2624/KLK10.f3 | GCCCAGAGGCTCCATCGT | 18 | 294 |
| KLK10 | NM_002776 | S2625/KLK10.r3 | CAGAGGTTTGAACAGTGCAGACA | 23 | 295 |
| KLK10 | NM_002776 | S4978/KLK10.p3 | CCTCTTCCTCCCCAGTCGGCTGA | 23 | 296 |
| KRT14 | NM_000526 | S1853/KRT14.f1 | GGCCTGCTGAGATCAAAGAC | 20 | 297 |
| KRT14 | NM_000526 | S1854/KRT14.r1 | GTCCACTGTGGCTGTGAGAA | 20 | 298 |
| KRT14 | NM_000526 | S5037/KRT14.p1 | TGTTCCTCAGGTCCTCAATGGTCTTG | 26 | 299 |
| KRT17 | NM_000422 | S0172/KRT17.f2 | CGAGGATTGGTTCTTCAGCAA | 21 | 300 |
| KRT17 | NM_000422 | S0174/KRT17.r2 | ACTCTGCACCAGCTCACTGTTG | 22 | 301 |
| KRT17 | NM_000422 | S5013/KRT17.p2 | CACCTCGCGGTTCAGTTCCTCTGT | 24 | 302 |
| KRT18 | NM_000224 | S1710/KRT18.f2 | AGAGATCGAGGCTCTCAAGG | 20 | 303 |
| KRT18 | NM_000224 | S1711/KRT18.r2 | GAGCCTTTTACTTCCTCTTCG | 20 | 304 |
| KRT18 | NM_000224 | S4762/KRT18.p2 | TGGTTCTTCTTCATGAAGAGCAGCTCC | 27 | 305 |
| KRT19 | NM_002276 | S1515/KRT19.f3 | TGAGCGGCAGAATCAGGAGTA | 21 | 306 |
| KRT19 | NM_002276 | S1516/KRT19.r3 | TGCGGTAGGTGGCAATCTC | 19 | 307 |
| KRT19 | NM_002276 | S4866/KRT19.p3 | CTCATGGACATCAAGTCGCGGCTG | 24 | 308 |

TABLE 6E-continued

| Gene | Accession | Probe Name | Seq | Length | SEQ ID NO: |
|---|---|---|---|---|---|
| KRT5 | NM_000424 | S0175/KRT5.f3 | TCAGTGGAGAAGGAGTTGGA | 20 | 309 |
| KRT5 | NM_000424 | S0177/KRT5.r3 | TGCCATATCCAGAGGAAACA | 20 | 311 |
| KRT5 | NM_000424 | S5015/KRT5.p3 | CCAGTCAACATCTCTGTTGTCACAAGCA | 28 | 310 |
| KRT8 | NM_002273 | S2588/KRT8.f3 | GGATGAAGCTTACATGAACAAGGTAGA | 27 | 312 |
| KRT8 | NM_002273 | S2589/KRT8.r3 | CATATAGCTGCCTGAGGAAGTTGAT | 25 | 313 |
| KRT8 | NM_002273 | S4952/KRT8.p3 | CGTCGGTCAGCCCTTCCAGGC | 21 | 314 |
| LOT1 variant 1 | NM_002656 | S0692/LOT1 v.f2 | GGAAAGACCACCTGAAAAACCA | 22 | 315 |
| LOT1 variant 1 | NM_002656 | S0693/LOT1 v.r2 | GTACTTCTTCCCACACTCCTCACA | 24 | 316 |
| LOT1 variant 1 | NM_002656 | S4793/LOT1 v.p2 | ACCCACGACCCCAACAAAATGGC | 23 | 317 |
| Maspin | NM_002639 | S0836/Maspin.f2 | CAGATGGCCACTTTGAGAACATT | 23 | 318 |
| Maspin | NM_002639 | S0837/Maspin.r2 | GGCAGCATTAACCACAAGGATT | 22 | 319 |
| Maspin | NM_002639 | S4835/Maspin.p2 | AGCTGACAACAGTGTGAACGACCAGACC | 28 | 320 |
| MCM2 | NM_004526 | S1602/MCM2.f2 | GACTTTTGCCCGCTACCTTTC | 21 | 321 |
| MCM2 | NM_004526 | S1603/MCM2.r2 | GCCACTAACTGCTTCAGTATGAAGAG | 26 | 322 |
| MCM2 | NM_004526 | S4900/MCM2.p2 | ACAGCTCATTGTTGTCACGCCGGA | 24 | 323 |
| MCM3 | NM_002388 | S1524/MCM3.f3 | GGAGAACAATCCCCTTGAGA | 20 | 324 |
| MCM3 | NM_002388 | S1525/MCM3.r3 | ATCTCCTGGATGGTGATGGT | 20 | 325 |
| MCM3 | NM_002388 | S4870/MCM3.p3 | TGGCCTTTCTGTCTACAAGGATCACCA | 27 | 326 |
| MCM6 | NM_005915 | S1704/MCM6.f3 | TGATGGTCCTATGTGTCACATTCA | 24 | 327 |
| MCM6 | NM_005915 | S1705/MCM6.r3 | TGGGACAGGAAACACACCAA | 20 | 328 |

TABLE 6F

| Gene | Accession | Probe Name | Seq | Length | SEQ ID NO: |
|---|---|---|---|---|---|
| MCM6 | NM_005915 | S4919/MCM6.p3 | CAGGTTTCATACCAACACAGGCTTCAGCAC | 30 | 329 |
| MDM2 | NM_002392 | S0830/MDM2.f1 | CTACAGGGACGCCATCGAA | 19 | 330 |
| MDM2 | NM_002392 | S0831/MDM2.r1 | ATCCAACCAATCACCTGAATGTT | 23 | 331 |
| MDM2 | NM_002392 | S4834/MDM2.p1 | CTTACACCAGCATCAAGATCCGG | 23 | 332 |
| MMP9 | NM_004994 | S0656/MMP9.f1 | GAGAACCATCTCACCGACA | 20 | 333 |
| MMP9 | NM_004994 | S0657/MMP9.r1 | CACCCGAGTGTAACCATAGC | 20 | 334 |
| MMP9 | NM_004994 | S4760/MMP9.p1 | ACAGGTATTCCTCTGCCAGCTGCC | 24 | 335 |
| MTA1 | NM_004689 | S2369/MTA1.f1 | CCGCCCTCACCTGAAGAGA | 19 | 336 |
| MTA1 | NM_004689 | S2370/MTA1.r1 | GGAATAAGTTAGCCGCGCTTCT | 22 | 337 |
| MTA1 | NM_004689 | S4855/MTA1.p1 | CCCAGTGTCCGCCAAGGAGCG | 21 | 338 |
| MYBL2 | NM_002466 | S3270/MYBL2.f1 | GCCGAGATCGCCAAGATG | 18 | 339 |
| MYBL2 | NM_002466 | S3271/MYBL2.r1 | CTTTTGATGGTAGAGTTCCAGTGATTC | 27 | 340 |
| MYBL2 | NM_002466 | S4742/MYBL2.p1 | CAGCATTGTCTGTCCTCCCTGGCA | 24 | 341 |
| P14ARF | S78535 | S2842/P14ARF.f1 | CCCTCGTGCTGATGCTACT | 19 | 342 |
| P14ARF | S78535 | S2843/P14ARF.r1 | CATCATGACCTGGTCTTCTAGG | 22 | 343 |
| P14ARF | S78535 | S4971/P14ARF.p1 | CTGCCCTAGACGCTGGCTCCTC | 22 | 344 |
| p27 | NM_004064 | S0205/p27.f3 | CGGTGGACCACGAAGAGTTAA | 21 | 345 |
| p27 | NM_004064 | S0207/p27.r3 | GGCTCGCCTCTTCCATGTC | 19 | 347 |
| p27 | NM_004064 | S4750/p27.p3 | CCGGGACTTGGAGAAGCACTGCA | 23 | 346 |
| P53 | NM_000546 | S0208/P53.f2 | CTTTGAACCCTTGCTTGCAA | 20 | 348 |
| P53 | NM_000546 | S0210/P53.r2 | CCCGGGACAAAGCAAATG | 18 | 350 |
| P53 | NM_000546 | S5065/P53.p2 | AAGTCCTGGGTGCTTCTGACGCACA | 25 | 349 |
| PAI1 | NM_000602 | S0211/PAI1.f3 | CCGCAACGTGGTTTTCTCA | 19 | 351 |
| PAI1 | NM_000602 | S0213/PAI1.r3 | TGCTGGGTTTCTCCTCCTGTT | 21 | 353 |
| PAI1 | NM_000602 | S5066/PAI1.p3 | CTCGGTGTTGGCCATGCTCCAG | 22 | 352 |
| PDGFRb | NM_002609 | S1346/PDGFRb.f3 | CCAGCTCTCCTTCCAGCTAC | 20 | 354 |
| PDGFRb | NM_002609 | S1347/PDGFRb.r3 | GGGTGGCTCTCACTTAGCTC | 20 | 355 |
| PDGFRb | NM_002609 | S4931/PDGFRb.p3 | ATCAATGCTCCGTCCGAGTGCTG | 24 | 356 |
| PI3KC2A | NM_002645 | S2020/PI3KC2.r1 | CACACTAGCATTTTCTCCGCATA | 23 | 357 |
| PI3KC2A | NM_002645 | S2021/PI3KC2.f1 | ATACCAATCACCGCACAAACC | 21 | 358 |
| PI3KC2A | NM_002645 | S5062/PI3KC2.p1 | TGCGCTGTGACTGGACTTAACAAATAGCCT | 30 | 359 |
| PPM1D | NM_003620 | S3159/PPM1D.f1 | GCCATCCGCAAAGGCTTT | 18 | 360 |
| PPM1D | NM_003620 | S3160/PPM1D.r1 | GGCCATTCCGCCAGTTTC | 18 | 361 |
| PPM1D | NM_003620 | S4856/PPM1D.p1 | TCGCTTGTCACCTTGCCATGTGG | 23 | 362 |
| PR | NM_000926 | S1336/PR.f6 | GCATCAGGCTGTCATTATGG | 20 | 363 |
| PR | NM_000926 | S1337/PR.r6 | AGTAGTTGTGCTGCCCTTCC | 20 | 364 |
| PR | NM_000926 | S4743/PR.p6 | TGTCCTTACCTGTGGGAGCTGTAAGGTC | 28 | 365 |
| PRAME | NM_006115 | S1985/PRAME.f3 | TCTCCATATCTGCCTTGCAGAGT | 23 | 366 |
| PRAME | NM_006115 | S1986/PRAME.r3 | GCACGTGGGTCAGATTGCT | 19 | 367 |
| PRAME | NM_006115 | S4756/PRAME.p3 | TCCTGCAGCACCTCATCGGGCT | 22 | 368 |
| pS2 | NM_003225 | S0241/pS2.f2 | GCCCTCCCAGTGTGCAAAT | 19 | 369 |
| pS2 | NM_003225 | S0243/pS2.r2 | CGTCGATGGTATTAGGATAGAAGCA | 25 | 371 |
| pS2 | NM_003225 | S5026/pS2.p2 | TGCTGTTTCGACGACACCGTTCG | 23 | 370 |
| RAD51C | NM_058216 | S2606/RAD51C.f3 | GAACTTCTTGAGCAGGAGCATACC | 24 | 372 |

TABLE 6G

| Gene | Accession | Probe Name | Seq | Length | SEQ ID NO: |
|---|---|---|---|---|---|
| RAD51C | NM_058216 | S2607/RAD51C.r3 | TCCACCCCCAAGAATATCATCTAGT | 25 | 373 |
| RAD51C | NM_058216 | S4764/RAD51C.p3 | AGGGCTTCATAATCACCTTCTGTTC | 25 | 374 |
| RB1 | NM_000321 | S2700/RB1.f1 | CGAAGCCCTTACAAGTTTCC | 20 | 375 |
| RB1 | NM_000321 | S2701/RB1.r1 | GGACTCTTCAGGGGTGAAAT | 20 | 376 |
| RB1 | NM_000321 | S4765/RB1.p1 | CCCTTACGGATTCCTGGAGGGAAC | 24 | 377 |
| RIZ1 | NM_012231 | S1320/RIZ1.f2 | CCAGACGAGCGATTAGAAGC | 20 | 378 |
| RIZ1 | NM_012231 | S1321/RIZ1.r2 | TCCTCCTCTTCCTCCTCCTC | 20 | 379 |
| RIZ1 | NM_012231 | S4761/RIZ1.p2 | TGTGAGGTGAATGATTTGGGGGA | 23 | 380 |
| STK15 | NM_003600 | S0794/STK15.f2 | CATCTTCCAGGAGGACCACT | 20 | 381 |
| STK15 | NM_003600 | S0795/STK15.r2 | TCCGACCTTCAATCATTTCA | 20 | 382 |
| STK15 | NM_003600 | S4745/STK15.p2 | CTCTGTGGCACCCTGGACTACCTG | 24 | 383 |
| STMY3 | NM_005940 | S2067/STMY3.f3 | CCTGGAGGCTGCAACATACC | 20 | 384 |
| STMY3 | NM_005940 | S2068/STMY3.r3 | TACAATGGCTTTGGAGGATAGCA | 23 | 385 |
| STMY3 | NM_005940 | S4746/STMY3.p3 | ATCCTCCTGAAGCCCTTTTCGCAGC | 25 | 386 |
| SURV | NM_001168 | S0259/SURV.f2 | TGTTTTGATTCCCGGGCTTA | 20 | 387 |
| SURV | NM_001168 | S0261/SURV.r2 | CAAAGCTGTCAGCTCTAGCAAAG | 24 | 389 |
| SURV | NM_001168 | S4747/SURV.p2 | TGCCTTCTTCCTCCCTCACTTCTCACCT | 28 | 388 |
| TBP | NM_003194 | S0262/TBP.f1 | GCCCGAAACGCCGAATATA | 19 | 390 |
| TBP | NM_003194 | S0264/TBP.r1 | CGTGGCTCTCTTATCCTCATGAT | 23 | 392 |
| TBP | NM_003194 | S4751/T8P.p1 | TACCGCAGCAAACCGCTTGGG | 21 | 391 |
| TGFA | NM_003236 | S0489/TGFA.f2 | GGTGTGCCACAGACCTTCCT | 20 | 393 |
| TGFA | NM_003236 | S0490/TGFA.r2 | ACGGAGTTCTTGACAGAGTTTTGA | 24 | 394 |
| TGFA | NM_003236 | S4768/TGFA.p2 | TTGGCCTGTAATCACCTGTGCAGCCTT | 27 | 395 |
| TIMP1 | NM_003254 | S1695/TIMP1.f3 | TCCCTGCGGTCCCAGATAG | 19 | 396 |
| TIMP1 | NM_003254 | S1696/TIMP1.r3 | GTGGGAACAGGGTGGACACT | 20 | 397 |
| TIMP1 | NM_003254 | S4918/TIMP1.p3 | ATCCTGCCCGGAGTGGAACTGAAGC | 25 | 398 |
| TOP2A | NM_001067 | S0271/TOP2A.f4 | AATCCAAGGGGGAGAGTGAT | 20 | 399 |
| TOP2A | NM_001067 | S0273/TOP2A.r4 | GTACAGATTTTGCCCGAGGA | 20 | 401 |
| TOP2A | NM_001067 | S4777/TOP2A.p4 | CATATGGACTTTGACTCAGCTGTGGC | 26 | 400 |
| TOP2B | NM_001068 | S0274/TOP2B.f2 | TGTGGACATCTTCCCCTCAGA | 21 | 402 |
| TOP2B | NM_001068 | S0276/TOP2B.r2 | CTAGCCCGACCGGTTCGT | 18 | 404 |
| TOP2B | NM_001068 | S4778/TOP2B.p2 | TTCCCTACTGAGCCACCTTCTCTG | 24 | 403 |
| TP | NM_001953 | S0277/TP.f3 | CTATATGCAGCCAGAGATGTGACA | 24 | 405 |
| TP | NM_001953 | S0279/TP.r3 | CCACGAGTTTCTTACTGAGAATGG | 24 | 407 |
| TP | NM_001953 | S4779/TP.p3 | ACAGCCTGCCACTCATCACAGCC | 23 | 406 |
| TP53BP2 | NM_005426 | S1931/TP53BP.f2 | GGGCCAAATATTCAGAAGC | 19 | 408 |
| TP53BP2 | NM_005426 | S1932/TP53BP.r2 | GGATGGGTATGATGGGACAG | 20 | 409 |
| TP53BP2 | NM_005426 | S5049/TP53BP.p2 | CCACCATAGCGGCCATGGAG | 20 | 410 |
| TRAIL | NM_003810 | S2539/TRAIL.f1 | CTTCACAGTGCTCCTGCAGTCT | 22 | 411 |
| TRAIL | NM_003810 | S2540/TRAIL.r1 | CATCTGCTTCAGCTCGTTGGT | 21 | 412 |
| TRAIL | NM_003810 | S4980/TRAIL.p1 | AAGTACACGTAAGTTACAGCCACACA | 26 | 413 |
| TS | NM_001071 | S0280/TS.f1 | GCCTCGGTGTGCCTTTCA | 18 | 414 |
| TS | NM_001071 | S0282/TS.r1 | CGTGATGTGCGCAATCATG | 19 | 416 |
| TS | NM_001071 | S4780/TS.p1 | CATCGCCAGCTACGCCCTGCTC | 22 | 415 |
| upa | NM_002658 | S0283/upa.f3 | GTGGATGTGCCCTGAAGGA | 19 | 417 |

TABLE 6H

| Gene | Accession | Probe Name | Seq | Length | SEQ ID NO: |
|---|---|---|---|---|---|
| upa | NM_002658 | S0285/upa.r3 | CTGCGGATCCAGGGTAAGAA | 20 | 418 |
| upa | NM_002658 | S4769/upa.p3 | AAGCCAGGCGTCTACACGAGAGTCTCAC | 28 | 419 |
| VDR | NM_000376 | S2745/VDR.f2 | GCCCTGGATTTCAGAAAGAG | 20 | 420 |
| VDR | NM_000376 | S2746/VDR.r2 | AGTTACAAGCCAGGGAAGGA | 20 | 421 |
| VDR | NM_000376 | S4S62/VDR.p2 | CAAGTCTGGATCTGGGACCCTTTCC | 25 | 422 |
| VEGF | NM_003376 | S0286/VEGF.f1 | CTGCTGTCTTGGGTGCATTG | 20 | 423 |
| VEGF | NM_003376 | S0288/VEGF.r1 | GCAGCCTGGGACCACTTG | 18 | 424 |
| VEGF | NM_003376 | S4782/VEGF.p1 | TTGCCTTGCTGCTCTACCTCCACCA | 25 | 425 |
| VEGFB | NM_003377 | S2724/VEGFB.f1 | TGACGATGGCCTGGAGTGT | 19 | 426 |
| VEGFB | NM_003377 | S2725/VEGFB.r1 | GGTACCGGATCATGAGGATCTG | 22 | 427 |
| VEGFB | NM_003377 | S4960/VEGFB.p1 | CTGGGCAGCACCAAGTCCGGA | 21 | 428 |
| WISP1 | NM_003882 | S1671/WISP1.f1 | AGAGGCATCCATGAACTTCACA | 22 | 429 |
| WISP1 | NM_003882 | S1672/WISP1.r1 | CAAACTCCACAGTACTTGGGTTGA | 24 | 430 |
| WISP1 | NM_003882 | S4915/WISP1.p1 | CGGGCTGCATCAGCACACGC | 20 | 431 |
| XIAP | NM_001167 | S0289/XIAP.f1 | GCAGTTGGAAGACACAGGAAAGT | 23 | 432 |
| XIAP | NM_001167 | S0291/XIAP.r1 | TGCGTGGCACTATTTTCAAGA | 21 | 434 |
| XIAP | NM_001167 | S4752/XIAP.p1 | TCCCAAATTGCAGATTTATCAACGGC | 27 | 433 |
| YB-1 | NM_004559 | S1194/YB-1.f2 | AGACTGTGGAGTTTGATGTTGTTGA | 25 | 435 |
| YB-1 | NM_004559 | S1195/YB-1.r2 | GGAACACCACCAGGACCTGTAA | 22 | 436 |
| YB-1 | NM_004559 | S4843/YB-1.p2 | TTGCTGCCTCCGCACCCTTTCT | 23 | 437 |
| ZNF217 | NM_006526 | S2739/ZNF217.f3 | ACCCAGTAGCAAGGAGAAGC | 20 | 438 |

TABLE 6H-continued

| Gene | Accession | Probe Name | Seq | Length | SEQ ID NO: |
|------|-----------|------------|-----|--------|------------|
| ZNF217 | NM_006526 | S2740/ZNF217.r3 | CAGCTGGTGGTAGGTTCTGA | 20 | 439 |
| ZNF217 | NM_006526 | S4961/ZNF217.p3 | CACTCACTGCTCCGAGTGCGG | 21 | 440 |

What is claimed is:

1. A method of predicting the likelihood of long-term survival without recurrence of breast cancer for a patient having estrogen receptor (ER)-positive breast cancer, the method comprising:
    (a) assaying an expression level of an RNA transcript or its expression product in a biological sample comprising a breast cancer cell obtained from the patient, wherein the RNA transcript is a MYBL2 transcript:
    (b) determining a normalized expression level of the MYBL2 transcript or its expression product, wherein the normalized expression level of the MYBL2 transcript or its expression product positively correlates with an increased likelihood of breast cancer recurrence in the patient; and
    (c) providing information regarding the likelihood of breast cancer recurrence for the patient, wherein the information comprises the normalized expression level of the MYBL2 transcript or its expression product.

2. The method of claim 1 wherein breast cancer is invasive breast carcinoma.

3. The method of claim 1 wherein said the biological sample is a fixed, wax-embedded breast cancer tissue specimen.

4. The method of claim 1 wherein the biological sample is isolated from core biopsy tissue or fine needle aspirated cells.

5. A method of preparing a personalized genomics profile for a patient with estrogen receptor (ER)-positive breast cancer, comprising the steps of:
    (a) assaying an expression level of an RNA transcript or its expression product in a biological sample comprising a breast cancer cell obtained from the patient, wherein the RNA transcript is a MYBL2 transcript;
    (b) determining a normalized expression level of the MYBL2 transcript or its expression product, wherein the normalized expression level of the MYBL2 transcript or its expression product positively correlates with an increased likelihood of breast cancer recurrence in the patient; and
    (c) creating a report summarizing data obtained from the normalized expression level and containing an estimate of likelihood of long-term survival without breast cancer recurrence in said patient.

6. The method of claim 5, wherein the biological sample is a fixed, paraffin-embedded biopsy sample.

7. The method of claim 5, wherein the RNA transcript is fragmented.

8. The method of claim 5 further comprising identifying a treatment option for the patient based on the normalized expression level.

9. The method of claim 1 wherein the expression level of the MYLB2 transcript, or its expression product, is normalized against a reference set comprising RNA transcripts of two or more housekeeping genes, or their expression products.

10. The method of claim 9 wherein the two or more housekeeping genes are selected from the group consisting of glyceraldehyde-3-phosphate dehydrogenase (GAPDH), Cyp1, albumin, actins, tubulins, cyclophilin, hypoxantine phosphoribosyltransferase (HRPT), L32, 28S, and 18S.

11. The method of claim 1, further comprising
    (a) assaying an expression level of at least one RNA transcript or its expression product in a biological sample comprising at least one breast cancer cell obtained from the patient, wherein the at least one RNA transcript is the transcript of a gene selected from the group consisting of: GRB7, CTSL, CD68, Chk1, AIB1, CCNB1, MCM2, FBXO5, STK15, SURV, EGFR, HIF1α, and TS:
    (b) determining a normalized expression level of the RNA transcript or its expression product wherein the normalized expression level of the RNA transcript or its expression product positively correlates with an increased likelihood of breast cancer recurrence; and
    (c) providing information comprising the likelihood of long-term survival without breast cancer recurrence for the patient, wherein the information comprises the normalized expression level of the RNA transcript or its expression product.

12. The method of claim 1, further comprising
    (a) assaying an expression level of at least one RNA transcript or its expression product in a biological sample comprising at least one breast cancer cell obtained from the patient, wherein the at least one RNA transcript is the transcript of a gene selected from the group consisting of: TP53BP2, Bcl2, KRT14, EstR1, IGFBP2, BAG1, CEGP1, KLK10, β-Catenin, γ-Catenin, DR5, P13KCA2, RAD51C, GSTM1, FHIT, RIZ1, BBC3, TBP, p27, IRS1, IGF1R, GATA3, ZNF217, CD9, pS2, ErbB3, TOP2B, MDM2, IGF1, and KRT19;
    (b) determining a normalized expression level of the at least one RNA transcript or its expression product, wherein the normalized expression level of the at least one RNA transcript or its expression product negatively correlates with a an increased likelihood of breast cancer recurrence.

13. The method of claim 1 further comprising determining the normalized expression level of a PR RNA transcript or its expression product, wherein the the normalized expression level of PR negatively correlates with an increased likelihood of breast cancer recurrence.

14. The method of claim 1 further comprising determining a normalized expression level of Her2 RNA transcript or its expression product, wherein the normalized expression level of Her2negatively correlates with an increased likelihood of long-term survival without breast cancer recurrence.

15. The method of claim 1 further comprising in step (a) determining the expression level of the PR RNA transcript or its expression product in a breast cancer tissue sample obtained from said patient, normalized against the expression levels of all RNA transcripts or their expression products in said breast cancer tissue sample, or of a reference set of RNA transcripts or their products.

16. The method of claim 1 or claim 15 further comprising in step (a) determining the expression level of the Her2 RNA transcript or its expression product in a breast cancer tissue sample obtained from said patient, normalized against the expression levels of all RNA transcripts or their expression products in said breast cancer tissue sample, or of a reference set of RNA transcripts or their products.

17. The method of claim 5 further comprising in step (b) determining the expression level of PR, wherein the expression level is normalized against a control gene or genes and optionally is compared to the amount found in a breast cancer reference tissue set.

18. The method of claim 5 or claim 17 further comprising in step (b) determining the expression level of Her2 wherein the expression level is normalized against a control gene or genes and optionally is compared to the amount found in a breast cancer reference tissue set.

19. The method of claim 1, wherein the information is provided in the form of a report.

20. The method of claim 11, wherein the information is provided in the form of a report.

* * * * *

UNITED STATES PATENT AND TRADEMARK OFFICE
CERTIFICATE OF CORRECTION

| | | |
|---|---|---|
| PATENT NO. | : 7,569,345 B2 | Page 1 of 1 |
| APPLICATION NO. | : 10/758307 | |
| DATED | : August 4, 2009 | |
| INVENTOR(S) | : Melody A. Cobleigh | |

It is certified that error appears in the above-identified patent and that said Letters Patent is hereby corrected as shown below:

Please insert the paragraph below as a separate paragraph at column 1, line 8, immediately following the first paragraph of the application:

--The subject matter claimed in this patent was made as a result of activities undertaken within the scope of a joint research agreement between Genomic Health, Inc. and Rush-Presbyterian-St. Luke's Medical Center.--

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,569,345 B2 Page 1 of 1
APPLICATION NO. : 10/758307
DATED : August 4, 2009
INVENTOR(S) : Melody A. Cobleigh It is certified that error appears in the above-identified patent and that said Letters Patent is hereby corrected as shown below:

In the Claims:

- Claim 3, column 181, line 22: Following "wherein" delete "said".
- Claim 14, column 182, line 34: Following "level of" insert --a--.
- Claim 14, column 182, line 36: Replace "Her2negatively" with --Her2 negatively--.

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,569,345 B2 | Page 1 of 1 |
| APPLICATION NO. | : 10/758307 | |
| DATED | : August 4, 2009 | |
| INVENTOR(S) | : Cobleigh et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 463 days.

Delete the phrase "by 463 days" and insert -- by 835 days --

Signed and Sealed this

Thirteenth Day of April, 2010

David J. Kappos
*Director of the United States Patent and Trademark Office*